United States Patent
Tsai et al.

(10) Patent No.: US 11,753,400 B2
(45) Date of Patent: Sep. 12, 2023

(54) D-AMINO ACID OXIDASE INHIBITORS AND THERAPEUTIC USES THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Yuan-Ting Hsieh, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 37 days.

(21) Appl. No.: 16/757,327

(22) PCT Filed: Oct. 18, 2018

(86) PCT No.: PCT/CN2018/110763
§ 371 (c)(1),
(2) Date: Apr. 17, 2020

(87) PCT Pub. No.: WO2019/076329
PCT Pub. Date: Apr. 25, 2019

(65) Prior Publication Data
US 2020/0331894 A1 Oct. 22, 2020

Related U.S. Application Data

(63) Continuation-in-part of application No. 15/787,557, filed on Oct. 18, 2017, now Pat. No. 10,336,724.

(51) Int. Cl.
| | | |
|---|---|---|
| *C07D 403/12* | (2006.01) | |
| *A23L 29/00* | (2016.01) | |
| *C07D 401/12* | (2006.01) | |
| *A61K 45/06* | (2006.01) | |

(52) U.S. Cl.
CPC .......... *C07D 403/12* (2013.01); *A23L 29/045* (2016.08); *C07D 401/12* (2013.01); *A61K 45/06* (2013.01)

(58) Field of Classification Search
CPC .................................................. C07D 403/12
See application file for complete search history.

(56) References Cited

U.S. PATENT DOCUMENTS

| | | |
|---|---|---|
| 2010/0216873 A1 | 8/2010 | Wempe et al. |
| 2014/0005181 A1 | 1/2014 | Smith et al. |

FOREIGN PATENT DOCUMENTS

| | | |
|---|---|---|
| CN | 103667245 A | 3/2014 |
| CN | 106749045 A | 5/2017 |
| WO | WO 2005/066135 A2 | 7/2005 |
| WO | WO 2010/017418 A1 | 2/2010 |

OTHER PUBLICATIONS

Ali et al., Influence of plasma-activated compounds on melanogenesis and tyrosinase activity. Sci Rep. Mar. 2, 2016;6:21779(1-20).
Eistert et al., Synthesen von N-Hydroxy-carbostyrilen. Justus Liebigs Ann Chem. Aug. 11, 1969;725:37-51.
Xie et al., Development of D-amino acid oxidase inhibitors progress in modem biomedicine. May 31, 2016;16:2582-8.
Katane et al., Identification of novel D-amino acid oxidase inhibitors by in silico screening and their functional characterization in vitro. J Med Chem. Mar. 14, 2013;56(5):1894-907. Epub Feb. 22, 2013.
Shin et al., A novel compound, maltolyl p-coumarate, attenuates cognitive deficits and shows neuroprotective effects in vitro and in vivo dementia models. J Neurosci Res. Aug. 15, 2007;85(11):2500-11.
Sun et al., Synthesis and Biological Evaluation of Quinolinone Compounds as SARS CoV 3CLpro Inhibitors. Chin J Chem. Sep. 2013;31(9):1199-1206, Epub Jul. 19, 2013.

*Primary Examiner* — Brian E McDowell
(74) *Attorney, Agent, or Firm* — McDermott Will & Emery LLP

(57) ABSTRACT

The present invention relates to compounds of Formula (I):

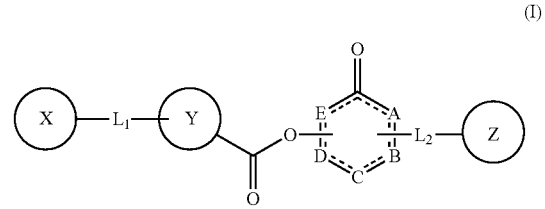

or a pharmaceutically acceptable salt thereof, wherein: each of A, B, C, D, and E, independently, is C, N, N—H, O, S, or absent; ----- is a single bond or a double bond; each of X, Y, and Z, independently, is aryl, heteroaryl, aralkyl, H, or absent; each of $L_1$ and $L_2$, independently, is a moiety selected from O, $CH_2$, C=O, $C_{2-10}$ alkyl, $C_{2-10}$ alkenyl, $C_{2-10}$ alkynyl, —$((CH_2)_n$—W)—, wherein n=0, 1, 2, 3, 4, or 5, and W is O or S, or absent; and when $L_2$ is absent, Z is aryl or heteroaryl fused with B ----- C. Also provided in the present invention is a method for inhibiting, treating and/or reducing the risk of a neuropsychiatric disorder, comprising administering a subject in need a composition comprising a compound of Formula (I).

15 Claims, 7 Drawing Sheets

Experimental design

Behavioral test: locomotion
Route: gavage
Vehicle: 30% PEG400 in PBS

| Groups | Numbers |
|---|---|
| Vehicle control | 6 |
| Example 1_446 mg/kg | 7 |
| Example 1_892 mg/kg | 7 |

C57BL/6 ♂

*Procedure of behavioral testing*

Experimental design

D-AMINO ACID OXIDASE INHIBITORS AND THERAPEUTIC USES THEREOF

RELATED APPLICATIONS

This application is a national stage filing under 35 U.S.C. § 371 of international application number PCT/CN2018/110763, filed on Oct. 18, 2018, which claims the benefit of U.S. Ser. No. 15/787,557, filed Oct. 18, 2017, both of which are incorporated by reference herein in their entities.

BACKGROUND OF THE INVENTION

The central nervous system (CNS) includes the brain and spinal cord. The CNS is vulnerable to various disorders, which may be caused by various factors, including genetic, trauma, infections, degeneration, structural defects and/or damage, tumors, blood flow disruption, and autoimmune disorders. Symptoms of a CNS disorder depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

D-amino acid oxidase (DAAO) is a peroxisomal enzyme that oxidizes D-amino acids to the corresponding imino acids. It has been reported that DAAO is involved in the metabolism of brain D-amino acids, including D-serine, and the regulation of the glutamatergic neurotransmission. As such, DAAO can be a target for treating central nervous system (CNS) disorders that are associated with D-serine and/or glutamatergic neurotransmission.

SUMMARY OF THE INVENTION

The present disclosure is based on, at least in part, the discovery of compounds able to effectively inhibit the activity of DAAO in a subject. Therefore, such compounds would benefit treatments of diseases and disorders associated with DAAO and/or glutamatergic neurotransmission such as CNS disorders.

Accordingly, provided herein are compounds of Formula (I) and uses thereof for inhibiting DAAO activity in a subject and/or treating or reducing the risk of a neuropsychiatric disorder.

In one aspect, the present invention provides a compound of Formula (I):

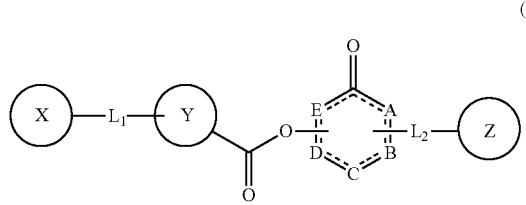

(I)

or a pharmaceutically acceptable salt thereof, wherein: each of A, B, C, D, and E, independently, is C, N, N—H, O, S, or absent; ═══ is a single bond or a double bond; each of X, Y, and Z, independently, is aryl, heteroaryl, aralkyl, H, or absent; each of $L_1$ and $L_2$, independently, is a moiety selected from O, $CH_2$, C═O, $C_{2-10}$ alkyl, $C_{2-10}$ alkenyl, $C_{2-10}$ alkynyl, —$((CH_2)_n$—W)—, wherein n=0, 1, 2, 3, 4, or 5, and W is O or S, or absent; and when $L_2$ is absent, Z is aryl or heteroaryl fused with B ═══ C.

In another aspect, the present disclosure provides compositions (e.g., pharmaceutical compositions, nutraceutical compositions, health foods, or medical foods) comprising an effective amount of a compound of Formula (I) and a carrier.

In yet another aspect, the present disclosure provides methods for inhibiting DAAO in a subject and/or treating or reducing the risk of a neuropsychiatric disorder, comprising administering to a subject in need thereof an effective amount of a compound of Formula (I) or an effective amount of a composition described herein.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E.L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

In a formula, ⁓⁓⁓ is a single bond where the stereochemistry of the moieties immediately attached thereto is not specified, - - - is absent or a single bond, and ═══ or ═══ is a single or double bond.

When a range of values is listed, it is intended to encompass each value and sub-range within the range. For example, "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, npropyl, isopropyl, cyclopropyl, —$CH_2$-cyclopropyl, vinyl, allyl, n-butyl, sec-butyl, isobutyl, tertbutyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl (C4) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl or $C_{1-3}$ alkyl, e.g., —$CH_3$). In certain embodiments, the alkyl group is a substituted $C_{1-10}$ alkyl (such as substituted $C_{1-6}$ alkyl or $C_{1-3}$ alkyl, e.g., —$CF_3$ or $CH_2OH$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —$CH=CHCH_3$ or

)

may be an (F)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-14 membered monocyclic or polycyclic 4n+2 aromatic ring system (e.g., having 6, 10, or 14 pi electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Polycyclic heteroaryl groups wherein two or three rings independently contain a heteroatom (e.g., furopyrrolyl, thienopyrrolyl, and the like) are also included.

In some embodiments, a heteroaryl group is a 5-14 membered aromatic ring system having ring carbon atoms and 1-4 ring heteroatoms provided in the aromatic ring system, wherein each heteroatom is independently selected from nitrogen, oxygen, and sulfur ("5-14 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridyl. Exemplary 6-membered heteroaryl groups containing two heteroatoms include, without limitation, pyridazinyl, pyrimidyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion, or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{cc}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-4}$ alkyl, C$_{1-4}$ perhaloalkyl, C$_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)+X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-4}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —S$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-4}$ alkyl, C$_{1-4}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$c, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O) (OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$$R^{aa}$, —$C(=NR^{bb})OR^{aa}$, —$C(=NR^{bb})N(R^{bb})_2$, —$S(=O)$$R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$ and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "inhibition", "inhibiting", "inhibit," or "inhibitor" refer to the ability of a compound of Formula (I) to reduce, slow, halt or prevent activity of a particular biological process in a cell relative to vehicle.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease.

The terms "administer," "administering," or "administration" refers to implanting, absorbing, ingesting, injecting, inhaling, or otherwise introducing a compound of Formula (I) described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of the compound of Formula (I) described herein refers to an amount sufficient to elicit the desired biological response (i.e., treating the condition). As will be appreciated by those of ordinary skill in this art, the effective amount of the compound of Formula (I) described herein may vary depending on such factors as the desired biological endpoint, the pharmacokinetics of the compound of Formula (I), the condition being treated, the mode of administration, and the age and health of the subject. In certain embodiments, an effective amount is a therapeutically effective amount. In certain embodiments, an effective amount is a prophylactic effective amount. In certain embodiments, an effective amount is the amount of a compound of Formula (I) described herein in a single dose. In certain embodiments, an effective amount is the combined amounts of a compound of Formula (I) described herein in multiple doses.

A "therapeutically effective amount" of a compound of Formula (I) described herein is an amount sufficient to provide a therapeutic benefit in the treatment of a condition or to delay or minimize one or more symptoms associated with the condition. A therapeutically effective amount of a compound of Formula (I) means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound of Formula (I) described herein is an amount sufficient to prevent a condition, or one or more symptoms associated with the condition or prevent its recurrence. A prophylactically effective amount of a compound of Formula (I) means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neuropsychiatric disorder," including either neurological diseases or psychiatric disorders or CNS (central nervous system) disorders, or refers to a disorder that involves either psychiatric symptoms or syndromes caused by organic brain disorders. The main characteristics of neuropsychiatric symptoms include occurrence of the various psychiatric symptoms, cognitive impairment, neurological symptoms or the possibility of early cerebral development symptoms. For example, the neuropsychiatric disorder can include, but is not limited to, schizophrenia, psychotic disorders, Alzheimer's disease, dementia, frontotemporal dementia, mild cognitive impairment, benign forgetfulness, closed head injury, autistic spectrum disorder, Asperger's disorder, attention deficit hyperactivity disorders, obsessive compulsive disorder, tic disorders, childhood learning disorders, premenstrual syndrome, depression, suicidal ideation and/or behavior, bipolar disorder, anxiety disorders, post-traumatic stress disorder, chronic pain, eating disorders, addiction disorders, personality disorders, Parkinson's disorder, Huntington's disorder, multiple sclerosis or amyotrophic lateral sclerosis.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSMIV (APA, 1994, Diagnostic and Statistical Manual of Mental Disorders (Fourth Edition), Washington, D.C.) or DSMV criteria (APA, 2013, Diagnostic and Statistical Manual of Mental Disorders (Fourth Edition), Washington, D.C.).

As used herein, the term "personality disorders" refers to mental disorders characterized by enduring maladaptive patterns of behavior, cognition, and inner experience, exhibited across many contexts and deviating markedly from those accepted by the individual's culture. These patterns develop early, are inflexible, and are associated with significant distress or disability. Personality disorders include, but not limited to, paranoid, schizoid, schizotypal, antisocial, borderline, histrionic, narcissistic, avoidant, dependent, and obsessive-compulsive personality disorder.

The terms "health food" or "health food product" refers to any kind of liquid and solid/semi-solid materials that are used for nourishing humans and animals, for improving basic behavioral functioning, hyperactivity, anxiety, depression, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The terms "medical food" or "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

The details of one or more embodiments of the disclosure are set forth herein. Other features, objects, and advantages of the disclosure will be apparent from the Detailed Description, the Examples, and the Claims.

DETAILED DESCRIPTION

Figure 1:
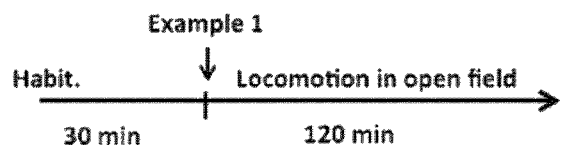
FIG. 1 is a diagram showing an exemplary design of the experiment of investigating locomotion in open field.

The present disclosure provides compounds of Formula (I) able to effectively inhibit D-amino acid oxidase (DAAO) and uses thereof in inhibiting, treating, and/or reducing the risk of a neuropsychiatric disorder.

I. Compounds and Compositions

One aspect of the present disclosure features a compound of Formula (I):

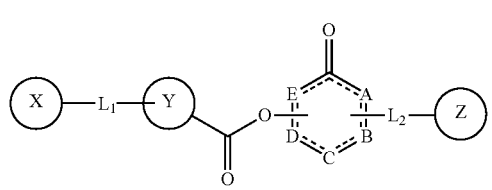

or a pharmaceutically acceptable salt thereof, wherein:
 each of A, B, C, D, and E, independently, is C, N, N—H, O, S, or absent;
 ═══ is a single bond or a double bond;
 each of X, Y, and Z, independently, is aryl, heteroaryl, aralkyl, H, or absent;
 each of $L_1$ and $L_2$, independently, is a moiety selected from O, $CH_2$, C═O, $C_{2-10}$ alkyl, $C_{2-10}$ alkenyl, $C_{2-10}$ alkynyl, —(($CH_2$)$_n$—W)—, wherein n=, 1, 2, 3, 4, or 5, and W is O or S, or absent; and when $L_2$ is absent, Z is aryl or heteroaryl fused with B ═══ C.

In some embodiments of the compound of Formula (I), D and E are independently carbon and connected via a double bond, and each of A, B, and C, is independently C, N, N—H, O, or S.

In some embodiments, the

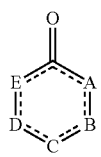

moiety of the compound of Formula (I) is

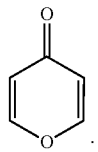

In some embodiments, the

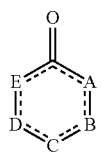

moiety of the compound of Formula (I) is

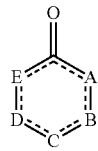

In some embodiments, the

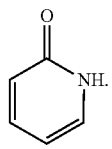

moiety of the compound of Formula (I) is

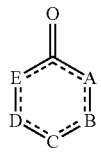

In some embodiments, the

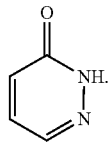

moiety of the compound of Formula (I) is

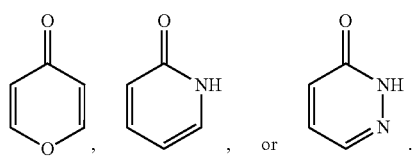

In some embodiments of the compound of Formula (I), $L_1$ and $L_2$ are independently selected from $CH_2$, $C_{2-10}$ alkyl, —(($CH_2$)$_n$—W)—, wherein n=, 1, 2, 3, 4, or 5, and W is O or S, or absent. In some embodiments, $L_1$ is —($CH_2$)— or —($CH_2$)$_2$—. In some embodiments, $L_1$ is —($CH_2$)—. In some embodiments, $L_1$ is —($CH_2$)$_2$—. In some embodiments, $L_2$ is —($CH_2$)—, —($CH_2$)$_2$—, or —($CH_2$)S—. In some embodiments, $L_2$ is —($CH_2$)—. In some embodi ments, $L_2$ is —(CH$_2$)$_2$—. In some embodiments, $L_2$ is —(CH$_2$)S—.

In some embodiments of the compound of Formula (I), $L_2$ is absent, and Z is aryl or heteroaryl fused with B═══C. In some embodiments, $L_2$ is absent, and Z is optionally substituted phenyl fused with B═══C to form a moiety of formula:

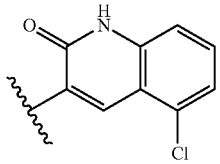

In some embodiments of the compound of Formula (I), each of X, Y, and Z is independently selected from benzyl, pyridyl, pyrimidyl, pyridazinyl, pyrazinyl, pyrrolyl, pyrazolyl, oxazolyl, thiazolyl, naphthyl, furopyrrolyl, thienopyrrolyl, indolyl, or absent. In some embodiments, X is optionally substituted phenyl. In some embodiments, X is phenyl optionally substituted with halogen. In some embodiments, X is phenyl optionally substituted with chloro or fluoro. In some embodiments, X is of the formula:

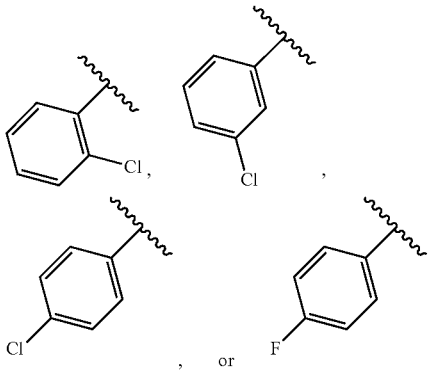

In some embodiments, X is of the formula:

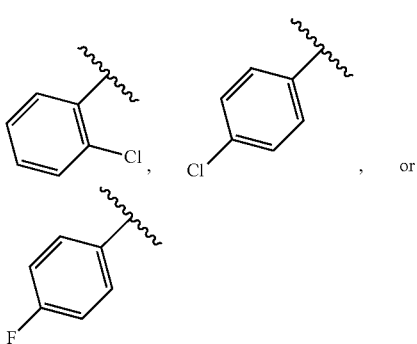

In some embodiments, X is naphthyl. In some embodiments, X is of the formula:

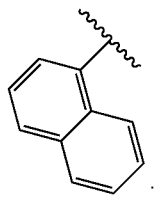 [SMILES: *c1cccc2ccccc12]

In some embodiments, Y is

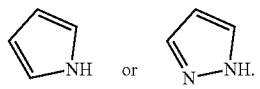

In some embodiments, Y is

In some embodiments, Y is

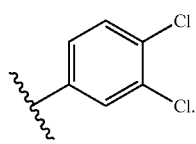 [SMILES: *c1ccc(Cl)c(Cl)c1]

In some embodiments, Z is optionally substituted phenyl or optionally substituted naphthyl. In some embodiments, Z is optionally substituted phenyl. In some embodiments, Z is optionally substituted naphthyl. In some embodiments, Z is unsubstituted naphthyl. In some embodiments, Z is phenyl optionally substituted with halogen. In some embodiments, Z is phenyl optionally substituted with chloro or fluoro. In some embodiments, Z is of the formula:

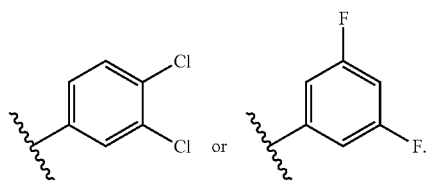 [SMILES: *c1ccc(Cl)c(Cl)c1 ; *c1cc(F)cc(F)c1]

In some embodiments, Z is of the formula:

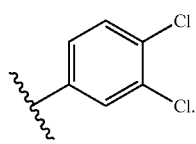 [SMILES: *c1ccc(Cl)c(Cl)c1]

In some embodiments, Z is of the formula:

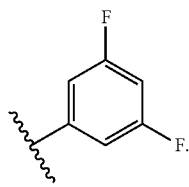 [SMILES: *c1cc(F)cc(F)c1]

In some embodiments, the compound of Formula (I) is a compound of Formula (I-a):

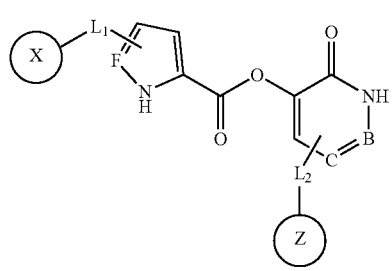
(I-a)

or a pharmaceutically acceptable salt thereof, wherein B and F, independently, is C or N; C is C, X and Z, independently, is aryl or heteroaryl; each of $L_1$ and $L_2$, independently, is a $C_1$-$C_{10}$ moiety, or absent; and when $L_2$ is absent, Z is aryl or heteroaryl fused with B=C. In some embodiments, F is C. In some embodiments, the compound of Formula (I-a) is of the formula:

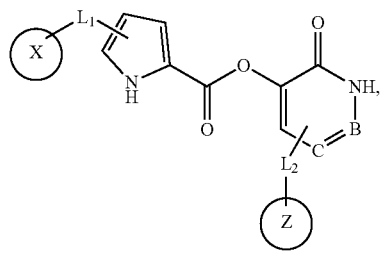

or a pharmaceutically acceptable salt thereof.

In some embodiments, the compound of Formula (I) is a compound of Formula (I-b):

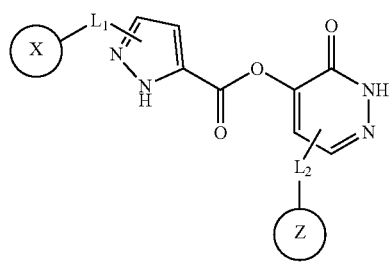
(I-b)

or a pharmaceutically acceptable salt thereof, wherein X and Z, independently, are each aryl; and each of $L_1$ and $L_2$, independently, is a $C_1$-$C_{10}$ moiety.

In some embodiments, the compound of Formula (I) can be one of the following:

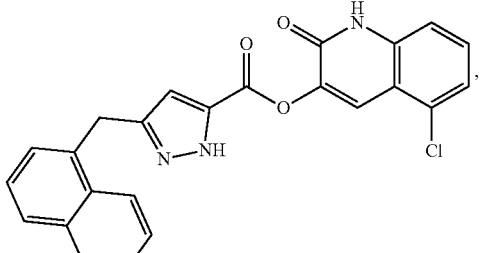
(39)

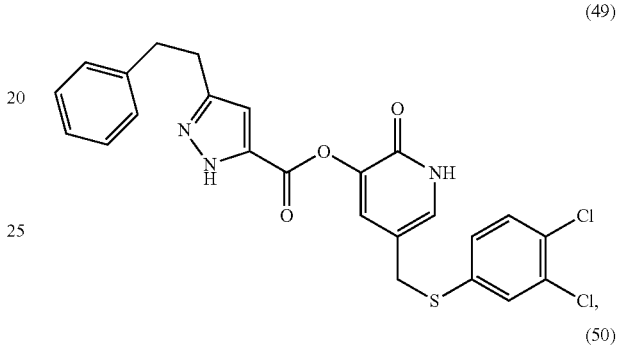
(49)

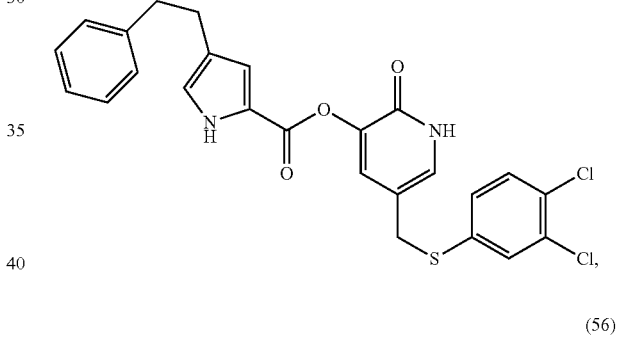
(50)

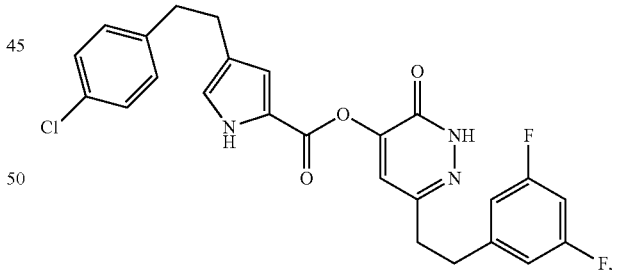
(56)

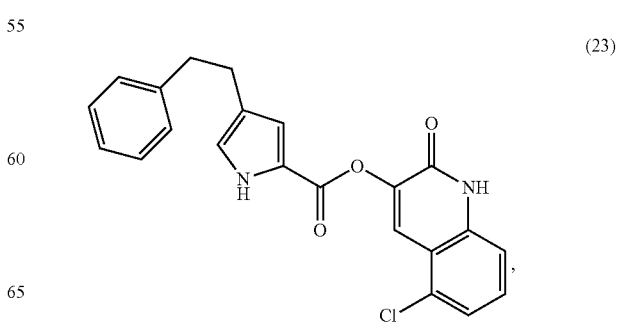
(23)

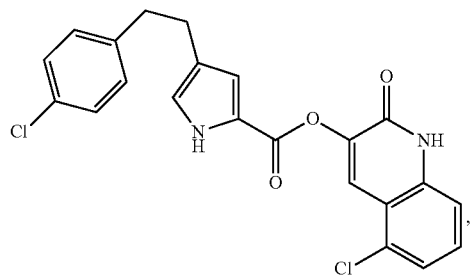
(18)
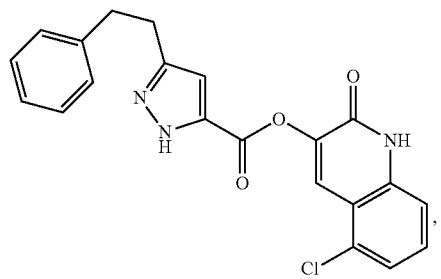
(27)
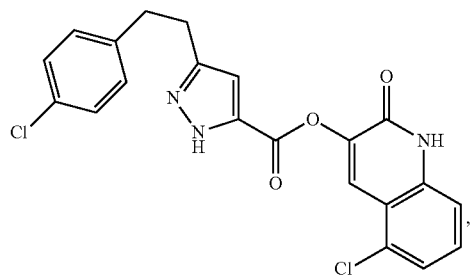
(32)
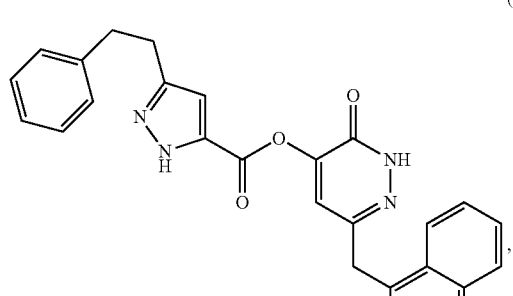
(62)
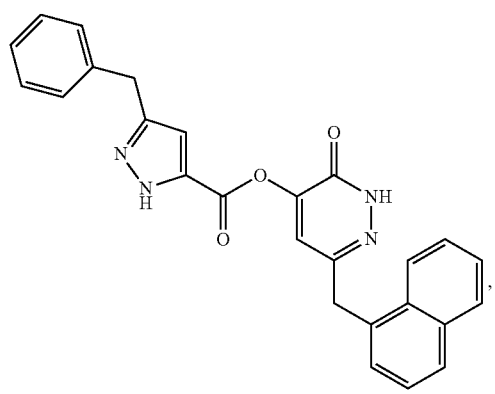
(77)
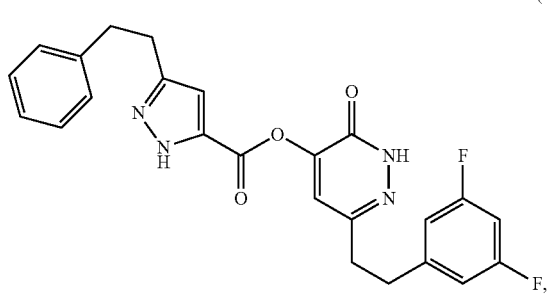
(78)
(67)
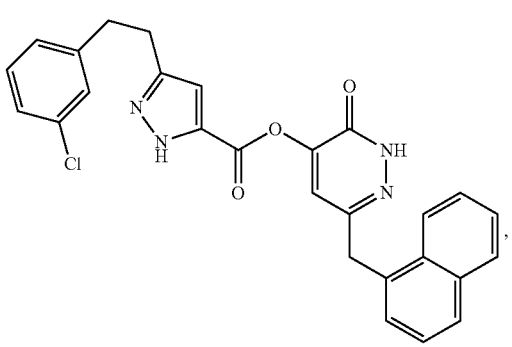
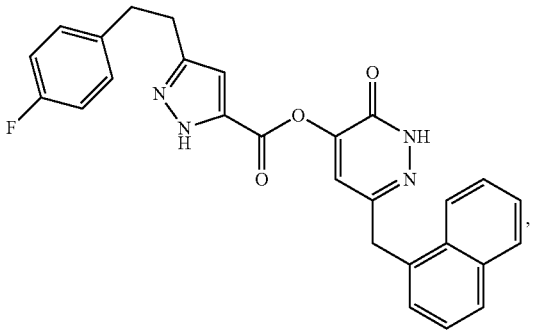
(72)
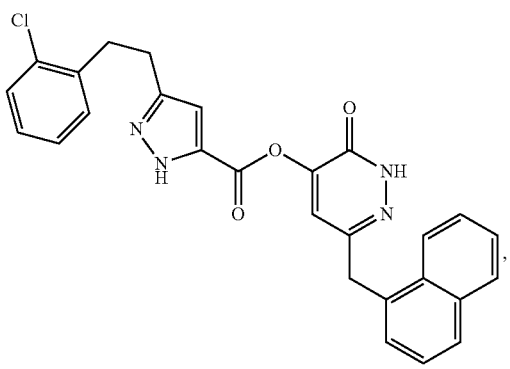

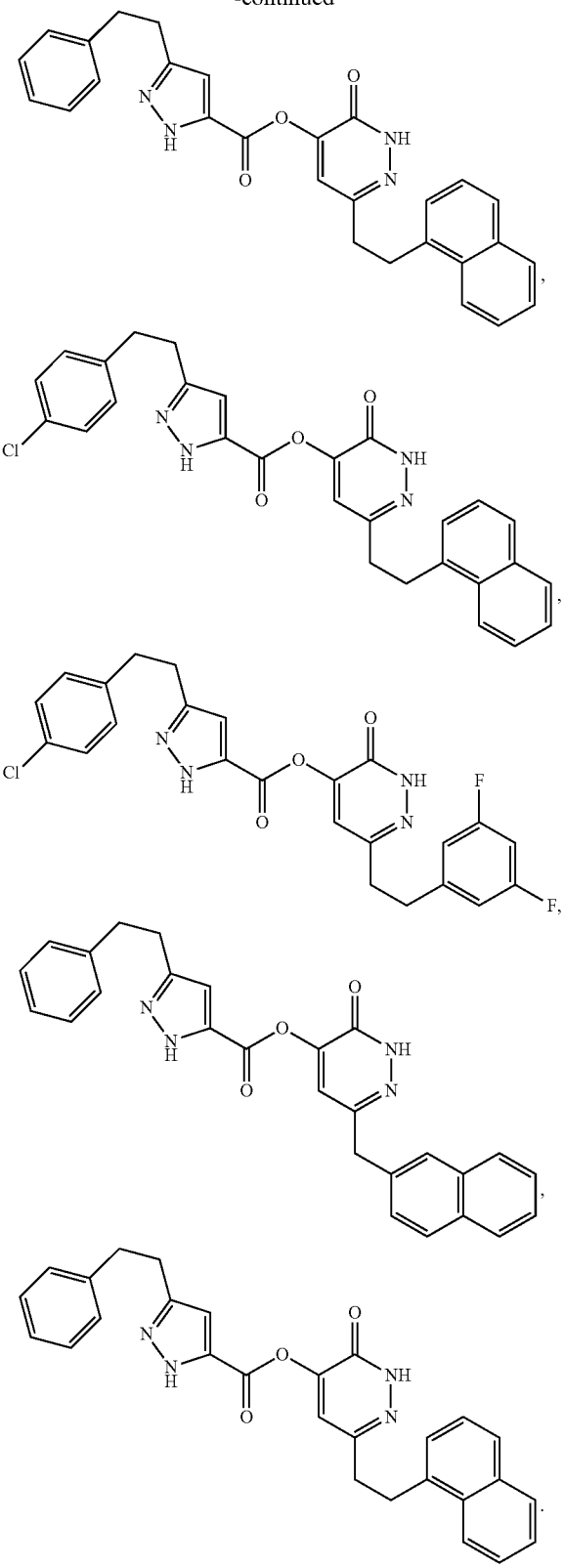

In some embodiments, any one of the compounds in Examples 1-26 or any one of the compounds in Table 1 is a compound of the present disclosure. Any of the compounds of Formula (I) as described herein may be formulated to form a pharmaceutical composition, a nutraceutical composition, a health food, or a medical food.

In some examples, the composition described herein is a pharmaceutical composition, which further comprises a pharmaceutically acceptable carrier, an excipient, or stabilizer. Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In other examples, the pharmaceutical composition described herein can be formulated in sustained-release format. Suitable examples of sustained-release preparations include semipermeable matrices of solid hydrophobic polymers containing tannic acids, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation, or intrathecal or intracerebral routes.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

In some embodiments, the compositions described herein can be a health food or a health food product, which can be any kinds of liquid and solid/semi-solid materials that are used for nourishing humans and animals, for improving basic behavioral functioning, hyperactivity, anxiety, depression, sensorimotor gating, pain threshold, memory and/or cognitive functioning, or for facilitating treatment of any of the target diseases noted herein (e.g., a neuropsychiatric disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, may comprise one or more edible carriers, which confer one or more of the benefits to the product as described herein. Examples of edible carriers include starch, cyclodextrin, maltodextrin, methylcellulose, carboxy methyl cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein comprises the compound of Formula (I) described herein and additional ingredients and supplements that promote good health and/or enhance stability and bioactivity of the compound of Formula (I).

The actions of nutraceutical compositions may be fast or/and short-term or may help achieve long-term health objectives as those described herein, e.g., improving basic behavioral functioning, hyperactivity, anxiety, depression, sensorimotor gating, pain threshold, memory and/or cognitive functioning in, e.g., human subjects who have or are at risk for a neuropsychiatric disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

In certain embodiments, the composition is a medical food, which may be a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising the compound of Formula (I) and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the compound of Formula (I) in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

In certain embodiments, the compound of Formula (I) described herein is provided in an effective amount in the pharmaceutical composition. In certain embodiments, the effective amount is a therapeutically effective amount (e.g., an amount effective for treating and/or reducing the risk for a neuropsychiatric disorder in a subject in need thereof). In certain embodiments, the neuropsychiatric disorder is a neurological disorder, e.g., Alzheimer's disease. In certain embodiments, the neuropsychiatric disorder is schizophrenia. In certain embodiments, the effective amount is a prophylactically effective amount (e.g., amount effective for inhibiting DAAO in a subject in need thereof or amount effective in treating or reducing the risk for a neuropsychiatric disorder in a subject in need thereof).

Pharmaceutical compositions described herein can be prepared by any method known in the art of pharmacology. In general, such preparatory methods include bringing the compound of Formula (I) described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compound of Formula (I) provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

II. Methods of Treatment

Another aspect of the present invention is to provide a method for inhibiting DAAO activity in a subject and/or treating or reducing the risk of a neuropsychiatric disorder, comprising administering to a subject in need an effective amount of the aforementioned a compound of Formula (I) or a composition comprising such.

The compound of Formula (I) described herein are useful in inhibiting DAAO activity in a subject and/or treating or reducing the risk for a neuropsychiatric disorder in a subject (e.g., a human patient having, suspected of having, or at risk for the neuropsychiatric disorder). In some embodiments, the neuropsychiatric disorder includes schizophrenia, psychotic disorders, Alzheimer's disease, frontotemporal dementia, dementia, mild cognitive impairment, benign forgetfulness, closed head injury, autistic spectrum disorder, Asperger's disorder, attention deficit hyperactivity disorders, obsessive compulsive disorder, tic disorders, childhood learning disorders, premenstrual syndrome, depression, suicidal ideation and/or behaviors, bipolar disorder, anxiety disorders, post-traumatic stress disorder, chronic pain, eating disorders, addiction disorders, personality disorders, Parkinson's disorder, Huntington's disorder, multiple sclerosis or amyotrophic lateral sclerosis.

The compound of Formula (I) provided herein, or a composition comprising such, can be administered by a suitable route as known to those skilled in the art, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically contemplated routes include oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of the compound of Formula (I) comprised in the aforementioned composition required to achieve an effective amount will vary from subject to subject, depending, for example, on species, age, and general condition of a subject, severity of the side effects or disorder, identity of the particular compound of Formula (I), mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of the compound of Formula (I) described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of the compound of Formula (I) described herein. In certain embodiments, a dose described herein includes independently between 3 mg and 10 mg, inclusive, of the compound of Formula (I) described herein. In certain embodiments, a dose described herein includes independently between 10 mg and 30 mg, inclusive, of the compound of Formula (I) described herein. In certain embodiments, a dose described herein includes independently between 30 mg and 100 mg, inclusive, of the compound of Formula (I) described herein. In certain embodiments, a dose described herein includes independently between 100 mg and 300 mg, inclusive, of the compound of Formula (I) as described herein. In certain embodiments, a dose described herein includes independently between 300 mg and 1000 mg, inclusive, of the compound of Formula (I) described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

III. Combined Treatment

The compound of Formula (I), as described herein, can be administered in combination with one or more additional pharmaceutical agents (e.g., therapeutically and/or prophylactically active agents) useful in treating and/or reducing the risk for a neuropsychiatric disorder. The additional pharmaceutical agents may improve the activity (e.g., activity (e.g., potency and/or efficacy) of the compound in treating and/or reducing the risk for a neuropsychiatric disorder in a subject in need thereof), improve bioavailability, improve safety, reduce drug resistance, reduce and/or modify metabolism, inhibit excretion, and/or modify distribution of the compound in a subject, biological sample, tissue, or cell. It will also be appreciated that the therapy employed may achieve a desired effect for the same disorder, and/or it may achieve different effects. In certain embodiments, the compound of Formula (I) described herein and the additional pharmaceutical agent show a synergistic effect that is absent in a treatment involving one of the compound of Formula (I) and the additional pharmaceutical agent, but not both.

The compound of Formula (I) can be administered concurrently with, prior to, currently with, or subsequent to one or more additional pharmaceutical agents, which may be useful as, e.g., combination therapies in treating and/or reducing the risk for a neuropsychiatric disorder in a subject. In some examples, the compound and the additional pharmaceutical agent(s) are formulated in one composition. In other examples, the compound and the additional pharmaceutical agent(s) are formulated in separate compositions.

Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric disorder in a subject. In certain embodiments, the additional pharmaceutical agent is a pharmaceutical agent approved by a regulatory agency (e.g., the US FDA) for treating and/or reducing the risk for a neuropsychiatric disorder in a subject. Each additional pharmaceutical agent may be administered at a dose and/or on a time schedule determined for that pharmaceutical agent. The additional pharmaceutical agents may also be administered together with each other and/or with the composition comprising the compound of Formula (I) described herein in a single dose or administered separately in different doses. The particular combination to employ in a regimen will take into account compatibility of the compound of Formula (I) described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is selected from agents for treating and/or reducing the risk for a neuropsychiatric disorder, or combinations thereof. In certain embodiments, the pharmaceutical compositions comprising the compound of Formula (I) described herein can be administered in combination with a therapy for treating and/or reducing the risk for a neuropsychiatric disorder.

In certain embodiments, the additional pharmaceutical agent is an agent for treating and/or reducing the risk for a neuropsychiatric disorder can be an antipsychotic, an antidepressant, a mood stabilizer, an anxiolytic, a psychostimulant and an agent for treating attention deficit hyperactivity disorder (ADHD), or an agent for treating Alzheimer's disease (AD).

The antipsychotic agent includes, but is not limited to, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupentixol, thiothixene, zuclopenthixol, clozapine, olanzapine, risperidone, quetiapine, ziprasidone, amisulpride, asenapine, paliperidone, aripiprazole, asenapine, cariprazine, iloperidone, pimavanserin, luradisone, brexpiprazole, cannabidiol, LY2140023, droperidol, pimozide, butaperazine, carphenazine, remoxipride, piperacetazine, sulpiride, acamprosate, and tetrabenazine. The antidepressant agent includes, but is not limited to, monoamine oxidase inhibitors (MAOIs), tricyclic antidepressants (TCAs), tetracyclic antidepressants (TeCAs), selective serotonin reuptake inhibitors (SSRIs), noradrenergic and specific serotonergic antidepressants (NASSAs), norepinephrine (noradrenaline) reuptake inhibitors, norepinephrine-dopamine reuptake inhibitors, or serotonin-norepinephrine reuptake inhibitors (SNRIs). Examples of the antidepressants include, but not limited to, fluoxetine, paroxetine, escitalopram, citalopram, sertraline, fluvoxamine, venlafaxine, Desvenlafaxine, vortioxetine, Levomilnacipran, Vilazodone, Selegiline, ketamine, milnacipran, duloxetine, mirtazapine, mianserin, reboxetine, bupropion, amitriptyline, nortriptyline, protriptyline, desipramine, trimipramine, amoxapine, bupropion, clomipramine, desipramine, doxepin, isocarboxazid, tranylcypromine, trazodone, nefazodone, phenelzine, lamatrogine, lithium, topiramate, gabapentin, carbamazepine, oxcarbazepine, valproate, maprotiline, brofaromine, gepirone, moclobemide, isoniazid, and iproniazid.

The psychostimulant agent or the agent for treating attention deficit hyperactivity disorder (ADHD) includes, but is not limited to, methylphenidate, dextro-threo-methylphenidate, isopropylphenidate, cocaine, amphetamine, methamphetamine, dextroamphetamine, 3,4-methylenedioxymethamphetamine, pemoline, phenmetrazine, diethylpropion, chlorphentermine, pipradol, p-hydroxymorphedrine, fenfluramine, 1-(2,5-dimethoxy-4-methylphenyl)-2-aminopropane, bupropion, statins, modafinil, arecoline, dexmethylphenidate, lisdexamfetamine dimesylate, mixed salts amphetamine, atomoxetine, clonidine hydrochloride, guanfacine hydrochloride, and arecoline.

The mood stabilizer agent includes, but is not limited to, lithium, lamotrigine, carbamazepine, oxcarbazepine, topiramate, zolpidem, carbamazepine, and valproate.

The anxiolytic agent includes, but is not limited to, diazepam, alprazolam, triazolam, indiplon, zaleplon, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, chlorazepate, calcium N-carboamoylaspartate, captodiamine, capuride, carbcloral, carbromal, chloral betaine, enciprazine, flesinoxan, ipsapiraone, ipsapirone, lesopitron, loxapine, methaqualone, methprylon, propanolol, tandospirone, trazadone, zopiclone, and zolpidem.

The agent for treating Alzheimer's disease (AD) includes, but is not limited to, donepezil, rivastigmine, galantamine, memantine, selfotel, midafotel, tacrine, selegiline, and vitamin E.

IV. Kits for Treatment

Also encompassed by the present disclosure are kits for use in treating any of the target disorders described herein. The kits provided herein may comprise a compound of Formula (I) described herein, or a composition comprising such. Optionally, the kit may further comprise one or more additional pharmaceutical agents as described herein.

Any of the kits described herein may comprise one or more containers (e.g., a vial, ampule, bottle, syringe, and/or dispenser package, or other suitable container), in which the active ingredients noted herein are placed. In some embodiments, provided kits may optionally further include an additional container comprising a pharmaceutical excipient for dilution or suspension of a pharmaceutical composition comprising the compound of Formula (I) described herein, and optionally the additional pharmaceutical agents. In some embodiments, the pharmaceutical composition comprising the compound of Formula (I) described herein provided in the one or more containers are combined to form one unit dosage form.

In certain embodiments, a kit described herein further includes instructions for using the composition comprising a compound of Formula (I) included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or reducing the risk for a neuropsychiatric. A kit described herein may include one or more additional pharmaceutical agents described herein as a separate composition.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

All chemical reagents used were purchased from vendors such as Sigma Aldrich and Alfa Aesar. MK801, an NMDA receptor antagonist, used in the experiments was purchased from Sigma (Sigma-Aldrich, USA). C57BL/6J male mice were purchased from the Laboratory Animal Center in the College of Medicine, National Taiwan University. The mice were group housed (3-5 mice per cage) with food and water available ad libitum in polysulfone ventilated cages (Alternative Design, AR, USA) in the animal rooms of SyneuRx International (Taiwan) Corp. $^1$H NMR spectra were recorded on a Bruker 300 MHz, or BRUKER 400 MHz spectrometer, and the chemical shifts were expressed in δ (ppm) values with trimethylsilane as an internal reference). Mass spectra were recorded on a Shimadzu LCMS-2020 Quadrupole LC/MS.

Example 1: Synthesis of 6-(hydroxymethyl)-4-oxo-4H-pyran-3-yl 1H-pyrrole-2-carboxylate (1)

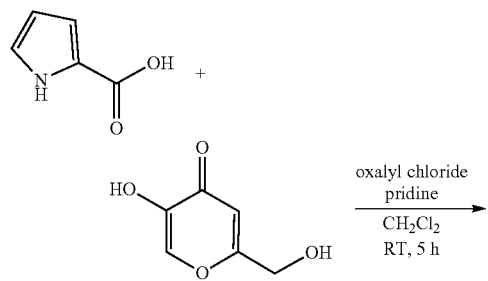

6-(Hydroxymethyl)-4-oxo-4H-pyran-3-yl 1H-pyrrole-2-carboxylate (1)

To a stirred suspension of pyrrole-2-carboxylic acid (3.0 g, 27.1 mmol) in dichloromethane (18 mL) at room temperature (RT) was added oxalyl chloride (8.5 mL, 99.0 mmol) in one portion. After 2-3 h, dichloromethane and oxalyl chloride were removed under reduced pressure. Benzene was added to the residue and removed under reduced pressure. Dichloromethane (20 mL) was added to the residue and the resulting solution was added dropwise into a solution of 5-hydroxy-2-(hydroxymethyl)-4H-pyran-4-one (5.8 g, 40.5 mmol) in pyridine (20 mL) at 0° C. for 2 h. The mixture was allowed to warm to RT and stirred overnight. Dichloromethane was removed by evaporation under reduced pressure and the residue was diluted with equivalent volume of water. The precipitate was filtered off, and the filtrate was poured into 1 L of water then kept at 4° C. overnight. The solid was filtered with suction and washed with ethanol. After drying in vacuum, 6-(hydroxymethyl)-4-oxo-4H-pyran-3-yl 1H-pyrrole-2-carboxylate (1) was obtained as an off-white solid (2.2 g, 34.5%), which is confirmed by $^1$H NMR (DMSO-$d_6$, 300 MHz) δ 12.14 (br s, 1H), 8.53 (s, 1H), 7.14 (m, 1H), 6.98 (m, 1H), 6.45 (s, 1H), 6.26 (s, 1H), 5.89 (t, J=6.0 Hz, 1H), 4.36 (d, J=6.0 Hz, 2H). ESI-MS, m/z=236 [M+H]$^+$.

Example 2: Synthesis of 6-(hydroxymethyl)-4-oxo-4H-pyran-3-yl 4-(4-chlorophenethyl)-1h-pyrrole-2-carboxylate (5)

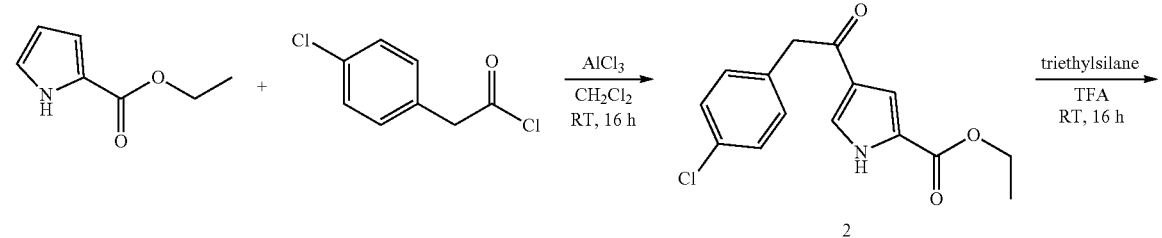

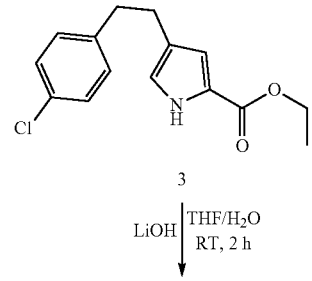

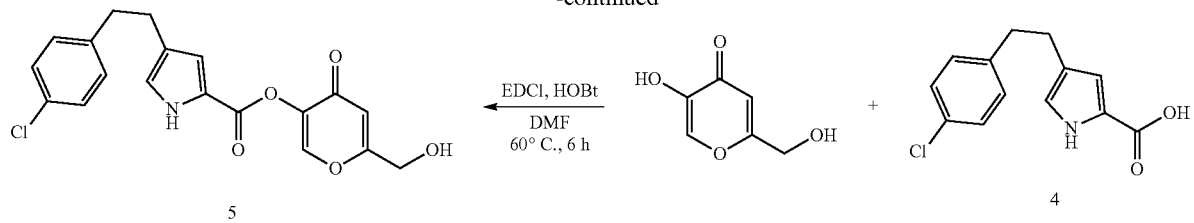

Ethyl 4-(2-(4-Chlorophenyl) Acetyl)-1H-Pyrrole-2-Carboxylate (2)

To a solution of 4-chlorobenzeneacetyl chloride (54.0 g, 300.0 mmol) in dichloromethane (500 mL) was added aluminum chloride (38.0 g, 280.0 mmol) at 0° C. under $N_2$. Then a solution of ethylpyrrole-2-carboxylate (20.0 g, 140.0 mmol) in dichloromethane (200 mL) was added dropwise to the mixture at 0° C. The reaction mixture was stirred at RT for 16 h. After the reaction was completed, the mixture was quenched by saturated $NH_4Cl_{(aq)}$. The mixture was extracted with ethyl acetate, washed with brine, dried over anhydrous sodium sulfate and filtered. The filtrate was evaporated in vacuo. The residue was purified by flash column chromatography with 0-30% ethyl acetate in petroleum ether to afford ethyl 4-(2-(4-chlorophenyl) acetyl)-1H-pyrrole-2-carboxylate (2) as a brown solid (23.0 g, 55%). ESI-MS, m/z=292 [M+H]$^+$.

Ethyl 4-(4-chlorophenyl)-1H-pyrrole-2-carboxylate (3)

To a solution of ethyl 4-(2-(4-chlorophenyl) acetyl)-1H-pyrrole-2-carboxylate (2, 23.0 g, 78.8 mmol) in trifluoroactic acid (200 mL) was added triethylsilane (40 mL, 244.3 mmol). The reaction mixture was stirred at RT for 16 h. After the reaction was completed, the mixture was evaporated in vacuo. The residue was purified by flash column chromatography with 0-30% ethyl acetate in petroleum ether to afford ethyl 4-(4-chlorophenyl)-1H-pyrrole-2-carboxylate (3) as a purple solid (12 g, 55%). ESI-MS, m/z=278 [M+H]$^+$.

4-(4-Chlorophenethyl)-1H-pyrrole-2-carboxylic acid (4)

To a solution of ethyl 4-(4-chlorophenyl)-1H-pyrrole-2-carboxylate (3, 2.0 g, 8.3 mmol) in tetrahydorfuran (50 mL) was added a solution of lithium hydroxide (1.0 g, 41.5 mmol) in water (20 mL) at RT. The reaction mixture was stirred at RT for 2 h. The resulting mixture was concentrated in vacuo. The pH value was adjusted to 5-6 with 1N HCl$_{(aq)}$. The mixture was filtered and the solid was collected and dried to afford 4-(4-chlorophenethyl)-1H-pyrrole-2-carboxylic acid (4) as an off-white solid (0.91 g, 48%). $^1$H NMR (DMSO-d$_6$, 400 MHz) δ 12.08 (s, 1H), 11.4 (s, 1H), 7.33-7.23 (m, 4H), 6.73 (s 1H), 6.58 (s, 1H), 2.84-2.80 (m, 2H), 2.71-2.67 (m, 2H). ESI-MS, m/z=278 [M+H]$^+$.

6-(Hydroxymethyl)-4-oxo-4H-pyran-3-yl 4-(4-chlorophenethyl)-1H-pyrrole-2-carboxylate (5)

To a stirring solution of 4-(4-chlorophenethyl)-1H-pyrrole-2-carboxylic acid (4, 0.5 g, 2.0 mmol) in N, N-dimethylformamide (15 mL) was added 5-hydroxy-2-(hydroxymethyl)-4H-pyran-4-one (0.3 g, 2.0 mmol), 1-ethyl-3-(3-dimethylaminopropyl) carbodiimide (0.4 g, 2.0 mmol) and hydroxybenzotriazole (0.3 mg, 2.0 mmol). The resulting mixture was stirred at 60° C. for 6 h. The reaction mixture was diluted with water, and extracted with ethyl acetate (3×30 mL). The combined organic layers were washed with brine (30 mL), dried over anhydrous sodium sulfate and concentrated under vacuum. The crude product was purified by flash column chromatography with dichloromethane/methanol (95:5) to afford 6-(hydroxymethyl)-4-oxo-4H-pyran-3-yl 4-(4-chlorophenethyl)-1H-pyrrole-2-carboxylate (5) as a white solid (0.4 g, 53%). $^1$H NMR (DMSO-d$_6$, 400 MHz) δ 11.91 (s, 1H), 8.57 (s, 1H), 7.34-7.32 (m, 2H), 7.26-7.24 (m, 2H), 6.92-6.91 (m, 1H), 6.87-6.86 (m, 1H), 6.45 (s, 1H), 5.79-5.76 (m, 1H), 4.38 (d, J=6.1 Hz, 2H), 2.87-2.80 (m, 2H), 2.76-2.72 (m, 2H). ESI-MS, m/z=374 [M+H]$^+$.

Example 3: Synthesis of 6-(hydroxymethyl)-4-oxo-4H-pyran-3-yl 4H-furo[3,2-b] pyrrole-5-carboxylate (9)

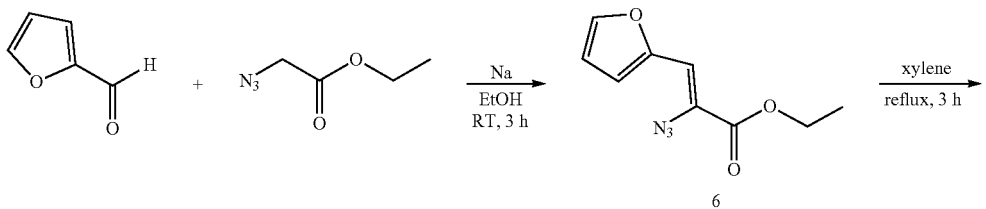

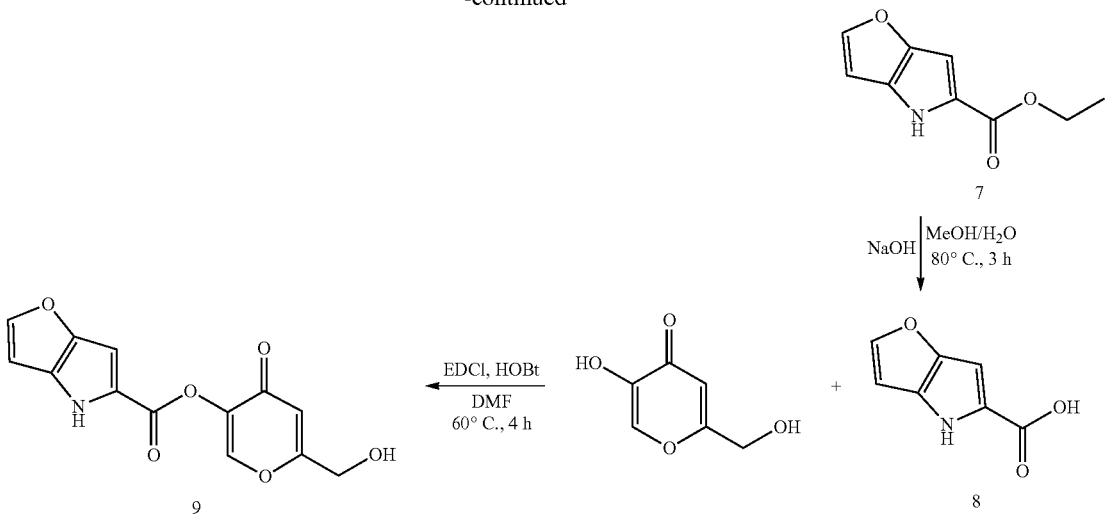

Ethyl (Z)-2-azido-3 (furan-2-yl) acrylate (6)

To a stirring solution of ethanol (200 mL) was added sodium (8.3 g, 360.9 mmol) under the ice-bath, and then ethyl 2-azidoacetate (44.8 g, 347.0 mmol) and furan-2-carbaldehyde (28.8 g, 299.7 mmol) was added slowly. The reaction mixture was stirred at RT for 3 h before quenched by the addition of saturated $NH_4Cl_{(aq)}$ (30 mL). The resulting solution was extracted with ethyl acetate (2×100 mL) and the organic layers combined. Then the organic layer was washed with brine (50 mL). The mixture was dried over anhydrous sodium sulfate and filtered. The residue was purified by flash column chromatography with ethyl acetate/petroleum ether (1:9) to afford ethyl (Z)-2-azido-3 (furan-2-yl) acrylate (6) as a yellow oil (10.0 g, 16%). $^1$H NMR (CDC$_3$, 300 MHz) δ 7.54-7.46 (m, 1H), 7.11 (d, J=3.7 Hz, 1H), 6.88 (s, 1H), 6.54 (m, 1H), 4.36 (q, J=7.1 Hz, 2H), 1.39 (t, J=7.1 Hz, 3H).

Ethyl 4H-furo[3,2-b] pyrrole-5-carboxylate (7)

The solution of ethyl (Z)-2-azido-3 (furan-2-yl) acrylate (6, 10.0 g, 48.3 mmol) in xylene (100 mL) was refluxed for 3 h. The reaction mixture was concentrated under vacuum, and the residue was purified by flash column chromatography with ethyl acetate/petroleum ether (1:9) to afford ethyl 4H-furo[3,2-b] pyrrole-5-carboxylate (7) as a yellow solid (7.2 g, 83%). $^1$H NMR (DMSO-d$_6$, 300 MHz) δ 11.64 (s, 1H), 7.79 (d, J=2.2 Hz, 1H), 6.74 (dd, J=1.8, 0.9 Hz, 1H), 6.61 (dd, J=2.2, 0.9 Hz, 1H), 4.26 (q, J=7.1 Hz, 2H), 1.30 (t, J=7.1 Hz, 3H). ESI-MS, m/z=180 [M+H]$^+$.

4H-Furo[3,2-b] pyrrole-5-carboxylic acid (8)

To a stirring solution of ethyl 4H-furo[3,2-b] pyrrole-5-carboxylate (7, 1.8 g, 10.1 mmol) in methanol (20 mL) was added a solution of sodium hydroxide (1.2 g, 30.0 mmol) in water (10 mL). The resulting mixture was stirred at 80° C. for 3 h before cooled to RT. The pH value of the mixture was adjusted to 1 with 1N HCl$_{(aq)}$. The mixture was filtered. The solid was collected and purified by recrystallization by with acetate/petroleum (1:4) to afford 4H-furo[3,2-b] pyrrole-5-carboxylic acid (8) as a brown solid (1.6 g, 100%). $^1$H NMR (DMSO-d$_6$, 300 MHz) δ 12.36 (s, 1H), 11.51 (s, 1H), 7.76 (d, J=2.1 Hz, 1H), 6.69 (dd, J=1.8, 0.9 Hz, 1H), 6.58 (dd, J=2.1, 0.9 Hz, 1H). ESI-MS, m/z=152 [M+H]$^+$.

6-(Hydroxymethyl)-4-oxo-4H-pyran-3-yl 4H-furo[3,2-b] pyrrole-5-carboxylate (9)

To a stirring solution of 4H-furo[3,2-b] pyrrole-5-carboxylic acid (8, 0.3 g, 2.0 mmol) in N, N-dimethylformamide (15 mL) was added 5-hydroxy-2-(hydroxymethyl)-4H-pyran-4-one (0.3 g, 2.2 mmol), 1-ethyl-3-(3-dimethylaminopropyl) carbodiimide (0.4 g, 2.0 mmol) and hydroxybenzotriazole (0.3 g, 2.0 mmol). The reaction mixture was stirred at 60° C. for 4 h and then diluted with ethyl acetate (50 mL). The mixture was washed with water (20 mL) and brine (20 mL), dried over anhydrous sodium sulfate and concentrated under vacuum. The residue was purified by flash column chromatography with methanol/dichloromethane (5:95) to afford 6-(hydroxymethyl)-4-oxo-4H-pyran-3-yl 4H-furo[3,2-b]-pyrrole-5-carboxylate (9) as a white solid (0.2 g, 28%). $^1$H NMR (DMSO-d$_6$, 300 MHz) δ 8.62 (s, 1H), 7.89 (d, J=2.2 Hz, 1H), 6.97 (d, J=0.9 Hz, 1H), 6.67 (dd, J=2.2, 0.9 Hz, 1H), 6.47 (s, 1H), 5.80 (s, 1H), 4.39 (s, 2H). ESI-MS, m/z=276 [M+H]$^+$.

Example 4: Synthesis of 6-(((4-chlorophenyl) thio)methy)-4-oxo-4H-pyran-3-yl 4-(4-chlorophenethyl)-1H-pyrrole-2-carboxylate (14)

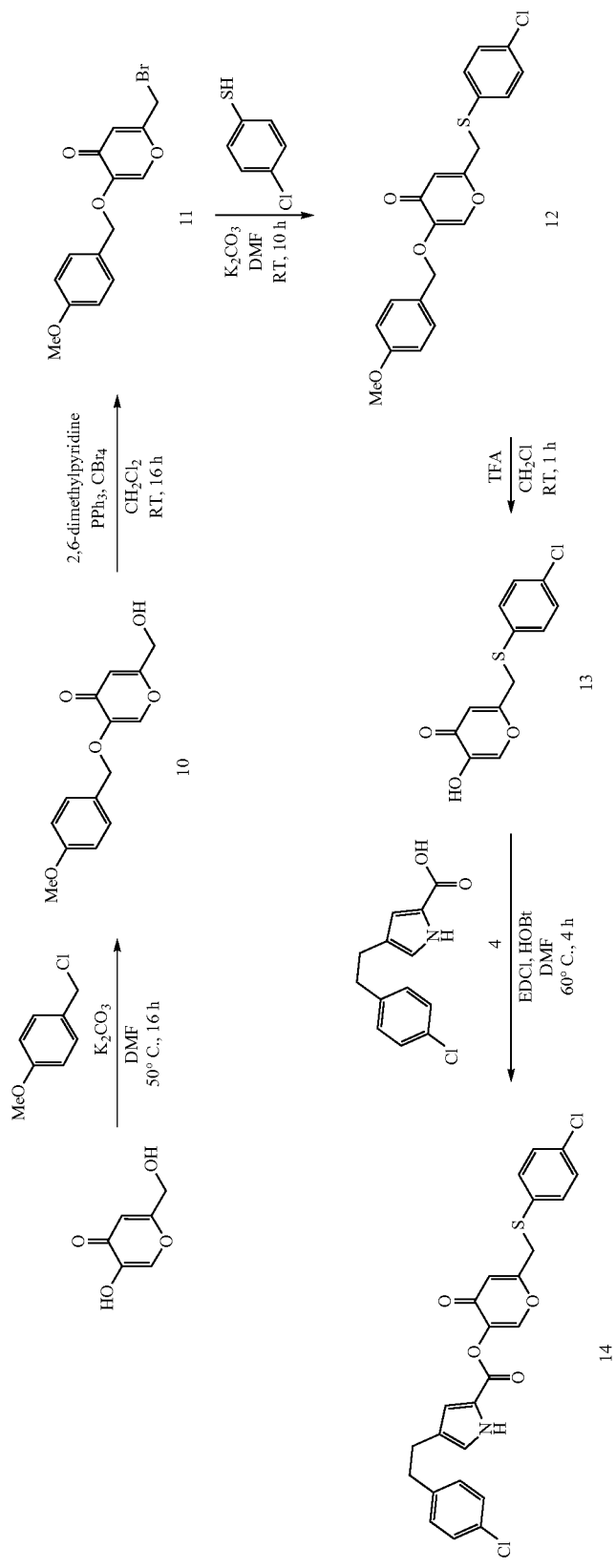

A mixture of 5-hydroxy-2-(hydroxymethyl)-4H-pyran-4-one (90.0 g, 630.0 mmol), 4-methoxybezyl chloride (110.0 g, 700.0 mmol) and potassium carbonate (132.0 g, 1000.0 mmol) in N,N-dimethylforamide (500 mL) was stirred for at 50° C. for 16 h. The reaction mixture was extracted with ethyl acetate, washed with brine, dried over anhydrous sodium sulfate and filtered. The filtrate was evaporated in vacuo. The residue was purified by flash column chromatography with ethyl acetate/petroleum ether (2:8) to afford 2-(hydroxymethyl)-5-((4-methoxybenzyl) oxy)-4H-pyran-4-one (10) as a yellow solid (130.0 g, 78%). $^1$H NMR (DMSO-d$_6$, 400 MHz) δ 8.15 (s, 1H), 7.35 (d, J=6.3 Hz, 2H), 6.95 (d, J=6.3 Hz, 2H), 6.32 (s, 1H), 5.75-5.70 (m, 1H), 4.87 (s, 2H), 4.30 (d, J=4.0 Hz, 2H), 3.77 (s, 3H). ESI-MS, m/z=263 [M+H]$^+$.

2-(Bromomethyl)-5-((4-methoxybenzyl) oxy)-4H-pyran-4-one (11)

To a solution of 2-(hydroxymethyl)-5-((4-methoxybenzyl) oxy)-4H-pyran-4-one (10, 30.0 g, 110.0 mmol) in dichloromethane (500 mL) was added 2,6-dimethylpyridine (26.0 mL, 170.0 mmol), triphenylphosphine (51.0 g, 170.0 mmol) and tetrabromomethane (57.0 g, 170.0 mmol). The mixture was stirred at RT for 16 h. After the reaction was completed, the mixture was evaporated in vacuo. The residue was purified by flash column chromatography with ethyl acetate/petroleum ether (1:4) to afford 2-(bromomethyl)-5-((4-methoxybenzyl) oxy)-4H-pyran-4-one (11) as a yellow solid (20.0 g, 54%). $^1$H NMR (DMSO-d$_6$, 400 MHz) δ 7.57 (s, 1H), 7.35-7.32 (m, 2H), 6.92-6.90 (m, 2H), 6.47 (s, 1H), 5.03 (s, 2H), 4.16 (s, 2H), 3.83 (s, 3H). ESI-MS, m/z=325 [M+H]$^+$.

2-(((4-Chlorophenyl) thio) methyl)-5-((4-methoxybenzyl) oxy)-4H-pyran-4-one (12)

To a mixture of 2-(bromomethyl)-5-((4-methoxybenzyl) oxy)-4H-pyran-4-one (11, 19.5 g, 60.0 mmol), 4-chlorobenzenethiol (11.0 g, 76.0 mmol) in N, N-dimethylformamide (100 mL) was added potassium carbonate (12.0 g, 80.0 mmol). The resulting mixture was stirred at RT for 10 h and then concentrated under vacuum. The residue was purified by flash column chromatography with ethyl acetate/petroleum ether (1:2) to afford 2-(((4-chlorophenyl) thio) methyl)-5-((4-methoxybenzyl) oxy)-4H-pyran-4-one (12) as a yellow solid (20.0 g, 84%). $^1$H NMR (CDC$_3$-d, 400 MHz) δ 7.50 (s, 1H), 7.34-7.32 (m, 6H), 6.93-6.91 (m, 2H), 6.20 (s, 1H), 5.02 (s, 2H), 3.84-3.79 (m, 5H). ESI-MS, m/z=389 [M+H]$^+$.

2-(((4-Chlorophenyl) thio) methyl)-5-hydroxy-4H-pyran-4-one (13)

To a stirring solution of 2-(((4-chlorophenyl) thio) methyl)-5-((4-methoxybenzyl) oxy)-4H-pyran-4-one (12, 1.3 g, 3.0 mmol) in dichloromethane (50 mL) was added trifluoroacetic acid (5.0 mL, 66.0 mmol). The resulting solution was stirred at RT for 1 h and concentrated under vacuum. The residue was triturated with diethyl ether to afford 2-(((4-chlorophenyl) thio) methyl)-5-hydroxy-4H-pyran-4-one (13) as an off-white solid (0.13 g, 16%). $^1$H NMR (DMSO-d$_6$, 400 MHz) δ 9.15 (s, 1H), 8.03 (s, 1H), 7.44-7.39 (m, 4H), 6.28 (s, 1H), 4.18 (s, 2H). ESI-MS, m/z=269 [M+H]$^+$.

6-(((4-Chlorophenyl) thio) methyl)-4-oxo-4H-pyran-3-yl 4-(4-chlorophenethyl)-1H-pyrrole-2-carboxylate (14)

To a stirring solution of 2-(((4-chlorophenyl) thio) methyl)-5-hydroxy-4H-pyran-4-one (13, 280.0 mg, 1.0 mmol) in N, N-dimethylformamide (10 mL) was added 4-(4-chlorophenethyl)-1H-pyrrole-2-carboxylic acid (4, 200.0 mg, 0.8 mmol), 1-ethyl-3-(3-dimethylaminopropyl) carbodiimide (153.0 mg, 0.8 mmol) and hydroxybenzotriazole (108.0 mg, 0.8 mmol). The reaction mixture was stirred at 60° C. for 4 h and then diluted with ethyl acetate (30 mL). The resulting mixture was washed with of brine (20 mL), dried over anhydrous sodium sulfate and concentrated under vacuum. The residue was purified by flash chromatography with ethyl acetate/hexane (3:7) to afford 6-(((4-chlorophenyl) thio) methyl)-4-oxo-4H-pyran-3-yl 4-(4-chlorophenethyl)-1H-pyrrole-2-carboxylate (14) as a white solid (150.0 mg, 37%). $^1$H NMR (DMSO-d$_6$, 300 MHz) δ 11.89 (s, 1H), 8.56 (s, 1H), 7.55-7.35 (m, 4H), 7.32 (dd, J=6.2, 2.0 Hz, 2H), 7.24 (d, J=8.4 Hz, 2H), 6.91 (d, J=2.7 Hz, 1H), 6.87-6.80 (m, 1H), 6.42 (s, 1H), 4.27 (s, 2H), 2.95-2.80 (m, 2H), 2.76-2.65 (m, 2H). ESI-MS, m/z=500 [M+H]$^+$.

Example 5: Synthesis of 6-(((4-chlorophenyl) thio) methyl)-4-oxo-4H-pyran-3-yl 4H-furo[3,2-b] pyrrole-5-carboxylate (15)

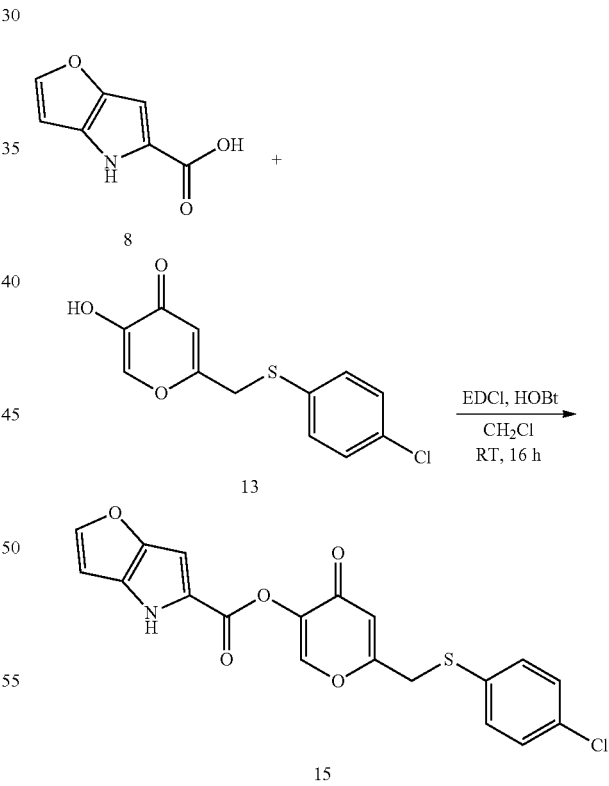

6-(((4-Chlorophenyl) thio) methyl)-4-oxo-4H-pyran-3-yl 4H-furo[3,2-b] pyrrole-5-carboxylate (15)

To a stirring solution of 2-(((4-chlorophenyl) thio) methyl)-5-hydroxy-4H-pyran-4-one (13, 450.0 mg, 1.7 mmol) in dichloromethane (50 mL) was added 4H-furo[3, 2-b]pyrrole-5-carboxylic acid (8, 360.0 mg, 2.4 mmol), 1-ethyl-3-(3-dimethylaminopropyl) carbodiimide (450.0 mg, 2.4 mmol) and hydroxybenzotriazole (320.0 mg, 2.4 mmol). The reaction mixture was stirred at RT for 16 h. After the reaction was completed, the mixture was extracted with water, and brine, dried over anhydrous sodium sulfate and concentrated under vacuum. The crude product was purified by Pre-HPLC to afford 6-(((4-chlorophenyl) thio) methyl)-4-oxo-4H-pyran-3-yl 4H-furo[3,2-b] pyrrole-5-carboxylate (15) as an off-white solid (159.1 mg, 24%). $^1$H NMR (DMSO-d$_6$, 300 MHz) δ 11.99 (s, 1H), 8.62 (s, 1H), 7.89 (d, J=2.4 Hz, 1H), 7.49-7.42 (m, 4H), 6.95 (s, 1H), 6.67 (s, 1H), 6.64 (s, 1H), 4.29 (s, 2H). ESI-MS, m/z=402 [M+H]$^+$.

Example 6: Synthesis of 5-chloro-2-oxo-1,2-dihydroquinolin-3-yl 4-(4-chlorophenethyl)-1H-pyrrole-2-carboxylate (18)

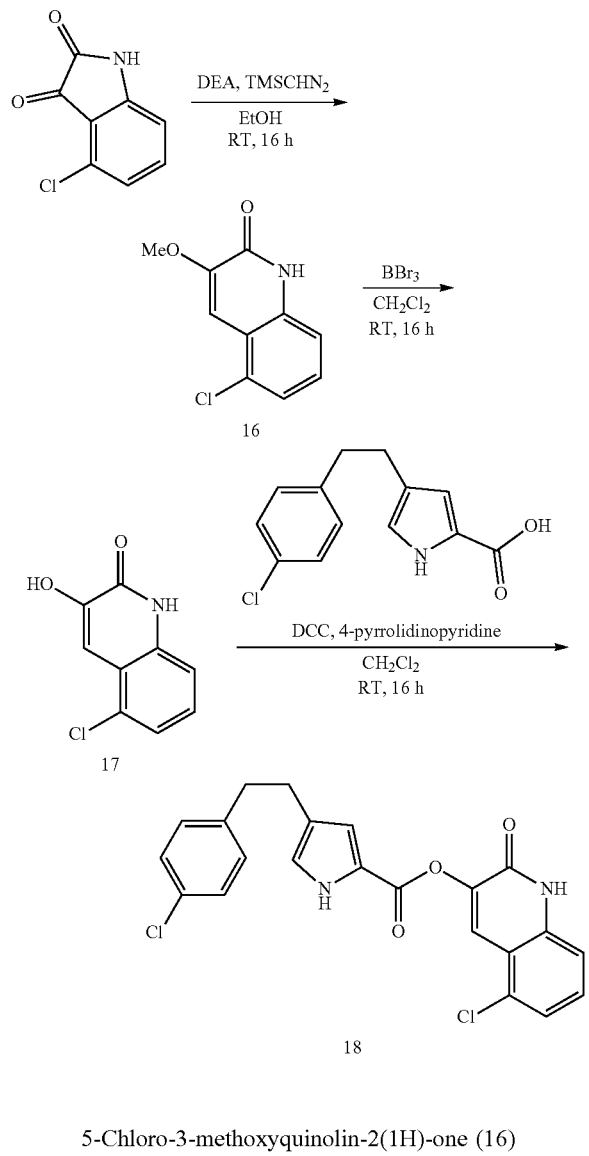

5-Chloro-3-methoxyquinolin-2(1H)-one (16)

To a stirring solution of 4-chloroindoline-2,3-dione (3.6 g, 20.0 mmol), diethylamine (25.0 mL, 240.0 mmol) in ethanol (30 mL) was added (trimethylsilyl) diazomethane (20.0 mL, 30.0 mmol) and the resulting mixture stirred at RT for 16 h. The solid precipitated from the reaction mixture, and was collected by filtration and rinsed with ethanol (3×10 mL) to provide 5-chloro-3-methoxyquinolin-2(1H)-one (16) as a gray solid (2.6 g, 65%). $^1$H NMR (DMSO-d$_6$, 400 MHz) δ 12.5 (s, 1H), 7.36-7.20 (m, 4H), 3.88 (s, 3H). ESI-MS, m/z=210 [M+H]$^+$.

5-Chloro-3-hydroxyquinolin-2(1H)-one (17)

To a stirring solution of 5-chloro-3-methoxyquinolin-2 (1H)-one (16, 2.6 g, 12.4 mmol) in dichloromethane (50 mL) was added boron tribromide (62.4 g, 248.0 mmol). The resulting solution was stirred at RT for 16 h. The solid was collected by filtration and rinsed with methanol (2×20 mL) to provide 5-chloro-3-hydroxyquinolin-2 (1H)-one (17) as a gray solid (1.2 g, 50%). $^1$H NMR (DMSO-d$_6$, 400 MHz) δ 12.26 (s, 1H), 10.07 (s, 1H), 7.32-7.23 (m, 4H). ESI-MS, m/z=196 [M+H]$^+$ 5-Chloro-2-oxo-1,2-dihydroquinolin-3-yl 4-(4-chlorophenethyl)-1H-pyrrole-2-carboxylate (18)

A mixture of 4-(4-chlorophenethyl)-1H-pyrrole-2-carboxylic acid (4, 0.4 g, 1.7 mmol), N, N-dicyclohexylcarbodiimide (0.35 g, 1.7 mmol), 5-chloro-3-hydroxyquinolin-2 (1H)-one (17, 0.3 g, 1.5 mmol) and 4-pyrrolidinopyridine (0.24 g, 0.2 mmol) in 50 mL of dichloromethane was stirred at RT for 16 h. The mixture was concentrated under vacuum and the crude product was purified by Prep-HPLC to afford 5-chloro-2-oxo-1,2-dihydroquinolin-3-yl 4-(4-chlorophenethyl)-1H-pyrrole-2-carboxylate (18) as an off-white solid (0.15 g, 23%). $^1$H NMR (DMSO-d$_6$, 400 MHz) δ 12.50 (s, 1H), 11.93 (s, 1H), 7.99 (s, 1H), 7.54 (m, 1H), 7.48-7.13 (m, 6H), 6.72-6.52 (m, 2H), 2.97-2.86 (m, 2H), 2.76-2.40 (m, 2H). ESI-MS, m/z=427 [M+H]$^+$.

Example 7: Synthesis of 5-chloro-2-oxo-1,2-dihydroquinolin-3-yl 4H-furo[3,2-b]pyrrole-5-carboxylate (19)

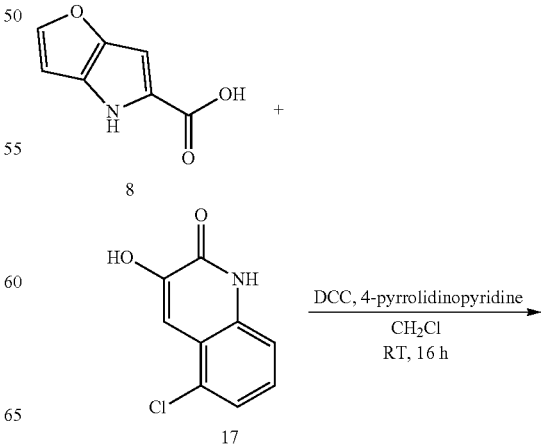

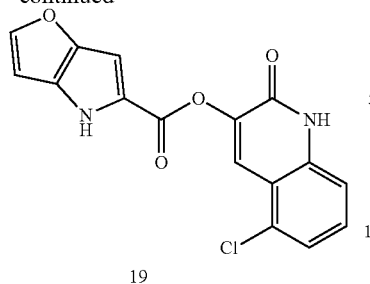

5-Chloro-2-oxo-1,2-dihydroquinolin-3-yl 4H-furo[3,2-b]pyrrole-5-carboxylate (19)

A mixture of 4H-furo[3,2-b] pyrrole-5-carboxylic acid (8, 0.5 g, 3.0 mmol), N, N-dicyclohexylcarbodiimide (0.6 g, 3.0 mmol), 5-chloro-3-hydroxyquinolin-2 (1H)-one (17, 0.6 g, 3.0 mmol) and 4-pyrrolidinopyridine (0.4 g, 0.3 mmol) in dichloromethane (20 mL) was stirred at RT for 16 h. The mixture was concentrated under vacuum and the residue was purified by flash chromatogram with methanol/dichloromethane (5:95) to afford 5-chloro-2-oxo-1,2-dihydroquinolin-3-yl 4H-furo[3,2-b] pyrrole-5-carboxylate (19) as a white solid (0.13 g, 13%). $^1$H NMR (DMSO-$d_6$, 300 MHz) δ 12.55 (s, 1H), 12.05 (s, 1H), 8.04 (s, 1H), 7.91 (d, J=2.4 Hz, 1H), 7.57-7.51 (m, 1H), 7.42-7.34 (m, 2H), 7.01 (s, 1H), 6.69-6.68 (m, 1H). ESI-MS, m/z=329 [M+H]$^+$.

Example 8: Synthesis of 5-chloro-2-oxo-1,2-dihydroquinolin-3-yl 4-phenethyl-H-pyrrole-2-carboxylate (23)

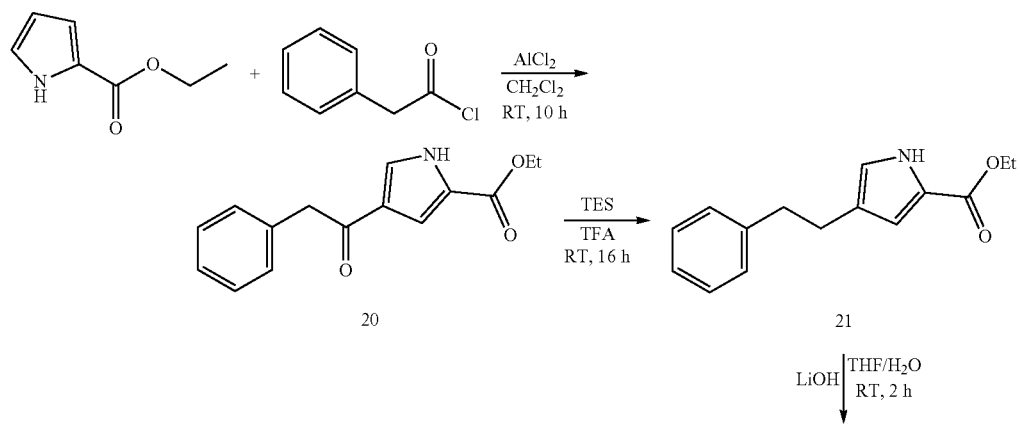

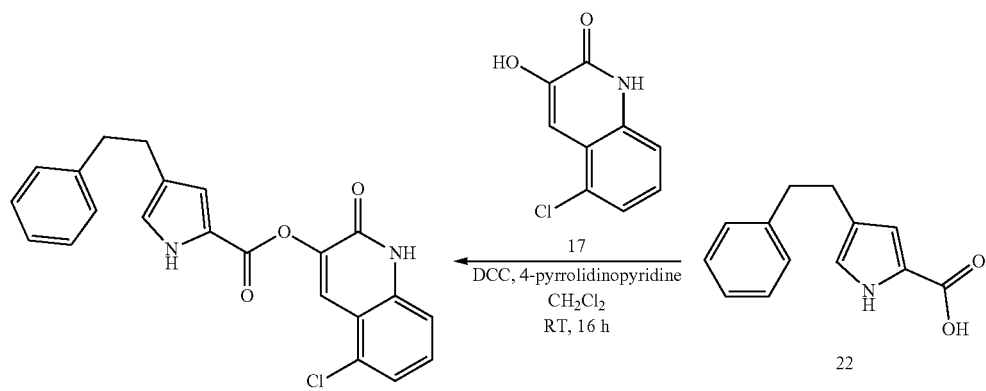

Ethyl 4-(2-phenylacetyl)-1H-pyrrole-2-carboxylate (20)

Ethyl 1H-pyrrole-2-carboxylate (20.0 g, 140.0 mmol) in dichloromethane (400 mL) was added to an ice cooled stirring mixture of aluminum chloride (23.0 g, 280.0 mmol) and 2-phenylacetyl chloride (44.0 g, 280.0 mmol) in dichloromethane (200 mL) under $N_2$. The resulting solution was stirred at RT for 10 h before quenched by the addition of saturated $NH_4Cl_{(aq)}$ (200 mL). The resulting solution was extracted with ethyl acetate (3×500 mL) and the organic layers combined. Then the organic layer was washed with brine, dried over magnesium sulfate, filtered and evaporated. The residue was purified by flash column chromatography with ethyl acetate/petroleum (1:3) to afford ethyl 4-(2-phenylacetyl)-1H-pyrrole-2-carboxylate (20) as a white solid (28.0 g, 76%). ESI-MS, m/z=358 [M+H]$^+$.

Ethyl 4-phenethyl-1H-pyrrole-2-carboxylate (21)

To a stirring solution of ethyl 4-(2-phenylacetyl)-1H-pyrrole-2-carboxylate (20, 19.0 g, 70.0 mmol) in trifluoroacetic acid (50 mL) was added triethylsilane (70.0 mL, 434.0 mmol). The resulting solution was stirred at RT for 10 h. The residue was purified by flash column chromatography with ethyl acetate/petroleum ether (1:3) to afford ethyl 4-phenethyl-1H-pyrrole-2-carboxylate (21) as a white solid (14.0 g, 78%). ESI-MS, m/z=244 [M+H]$^+$.

4-Phenethyl-1H-pyrrole-2-carboxylic acid (22)

To a stirring solution of ethyl 4-phenethyl-1H-pyrrole-2-carboxylate (21, 1.5 g, 6.2 mmol) in tetrahydrofuran (30 mL) was added the solution of lithium hydroxide (0.7 g, 31.0 mmol) in water (15 mL). The resulting solution was stirred at RT for 2 h. The resulting mixture was concentrated under vacuum. The resulting mixture was made acidic (pH=56) with the dropwise addition of 10% $HCl_{(aq)}$. The white solid that precipitated from the reaction was filtrated off and washed with water. The solid was purified by Pre-HPLC to obtain 4-phenethyl-1H-pyrrole-2-carboxylic acid (22) as a pink solid (0.13 g, 10%). $^1$H NMR (DMSO-$d_6$, 400 MHz) δ 12.21 (s, 1H), 11.51 (s, 1H), 7.53-7.14 (m, 5H), 6.55 (s, 1H), 6.48 (s, 1H), 3.34-2.90 (m, 2H), 2.79-2.66 (m, 2H). ESI-MS, m/z=216 [M+H]$^+$.

5-Chloro-2-oxo-1,2-dihydroquinolin-3-yl 4-phenethyl-1H-pyrrole-2-carboxylate (23)

A mixture of 4-phenethyl-1H-pyrrole-2-carboxylic acid (22, 1.2 g, 5.6 mmol), N, N-dicyclohexylcarbodiimide (1.2 g, 5.8 mmol), 5-chloro-3-hydroxyquinolin-2(1H)-one (17, 1.0 g, 5.1 mmol) and 4-pyrrolidinopyridine (0.9 g, 0.5 mmol) in dichloromethane (150 mL) was stirred at RT for 16 h. The mixture was concentrated under vacuum and the residue was purified by Pre-HPLC to afford 5-chloro-2-oxo-1,2-dihydroquinolin-3-yl 4-phenethyl-1H-pyrrole-2-carboxylate (23) as an off-white solid (0.13 g, 6%). $^1$H NMR (DMSO-$d_6$, 300 MHz) δ 12.50 (s, 1H), 11.93 (s, 1H), 7.99 (s, 1H), 7.56-7.52 (m, 1H), 7.41-7.17 (m, 8H), 6.96-6.92 (m, 1H), 3.34-2.86 (m, 2H), 2.81-2.75 (m, 2H). ESI-MS, m/z=393 [M+H]$^+$.

Example 9: Synthesis of 5-chloro-2-oxo-1,2-dihydroquinolin-3-yl 3-phenethyl-1H-pyrazole-5-carboxylate (27)

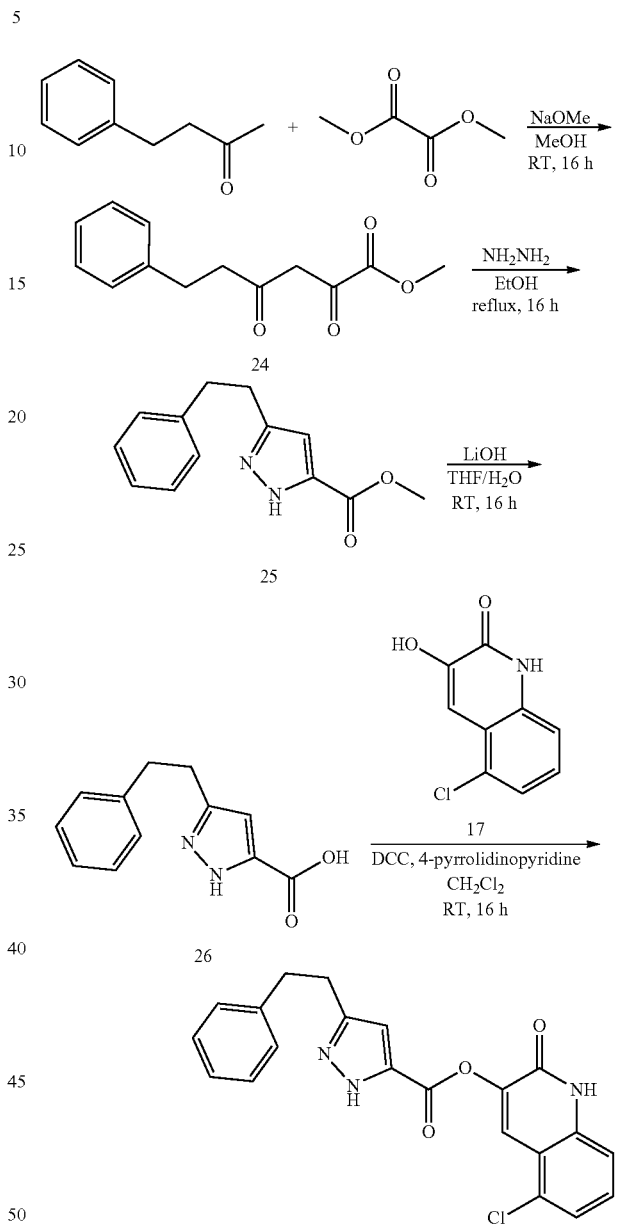

Methyl 2,4-dioxo-6-phenylhexanoate (24)

To a stirring solution of benzylacetone (30.0 g, 200.0 mmol) in dry methanol (300 mL) was added dimethyl oxalate (27.0 g, 230.0 mmol) and sodium methoxide (42.0 mL, 200.0 mmol) at 0° C. The reaction was slowly warmed to RT and stirred for 16 h. The mixture was diluted with ethyl acetate (500 mL) and brine, dried over magnesium sulfate, filtered and evaporated. The residue was purified by flash column chromatography with ethyl acetate/petroleum ether (1:3) to afford methyl 2,4-dioxo-6-phenylhexanoate (24) as a yellow solid (13.0 g, 27%). ESI-MS, m/z=235 [M+H]$^+$.

Methyl 3-phenethyl-1H-pyrazole-5-carboxylate (25)

To a stirring solution of methyl 2,4-dioxo-6-phenyl-hexanoate (24, 13.0 g, 56.0 mmol) in ethanol (56 mL) was added hydrazine (51 wt % aqueous solution) (10.0 mL, 213.9 mmol). The mixture was heated to reflux for 16 h. The reaction was concentrated in vacuo and the residue was purified by flash column chromatography with ethyl acetate/petroleum (2:3) to afford methyl 3-phenethyl-1H-pyrazole-5-carboxylate (25) as yellow oil (6.0 g, 50%). ESI-MS, m/z=231 [M+H]$^+$.

3-Phenethyl-1H-pyrazole-5-carboxylic acid (26)

To a stirring solution of methyl 3-phenethyl-1H-pyrazole-5-carboxylate (25, 5.0 g, 20.0 mmol) in tetrahydrofuran (40 mL) was added the solution of lithium hydroxide (1.0 g, 100.0 mmol) in water (20 mL). The mixture was stirred at RT for 16 h. Most of tetrahydrofuran was evaporated in vacuo. The pH value of the mixture was adjusted to 2 with 1N HCl$_{(aq)}$. The mixture was filtered and the solid was collected. The solid was purified by Pre-HPLC to afford further purified by Pre-HPLC to afford 3-phenethyl-1H-pyrazole-5-carboxylic acid (26) as a white solid (83.9 mg, 2%). $^1$H NMR (DMSO-d$_6$, 400 MHz) δ 12.97 (s, 2H), 7.30-7.17 (m, 5H), 6.48 (s, 1H), 2.92 (s, 4H). ESI-MS, m/z=217 [M+H]$^+$.

5-Chloro-2-oxo-1,2-dihydroquinolin-3-yl 3-phenethyl-1H-pyrazole-5-carboxylate (27)

A mixture of 3-phenethyl-1H-pyrazole-5-carboxylic acid (26, 100.0 mg, 0.5 mmol), N, N-dicyclohexylcarbodiimide (100 mg, 0.5 mmol), 5-chloro-3-hydroxyquinolin-2(1H)-one (17, 84.0 mg, 0.4 mmol) and 4-pyrrolidinopyridine (7.0 mg, 0.05 mmol) in dichloromethane (20 mL) was stirred at RT for 16 h. The mixture was concentrated under vacuum and the crude product was purified by Pre-HPLC to afford 5-chloro-2-oxo-1,2-dihydroquinolin-3-yl 3-phenethyl-1H-pyrazole-5-carboxylate (27) as a white solid (17.0 mg, 10%). $^1$H NMR (DMSO-d$_6$, 400 MHz) δ 13.54 (s, 1H), 12.55 (s, 1H), 8.04 (s, 1H), 7.55 (m, 1H), 7.42-7.19 (m, 7H), 6.72 (s, 1H), 2.99 (s, 4H). ESI-MS, m/z=394 [M+H]$^+$.

Example 10: Synthesis of 5-chloro-2-oxo-1,2-dihydroquinolin-3-yl 3-(4-chlorophenethyl)-1H-pyrazole-5-carboxylate (32)

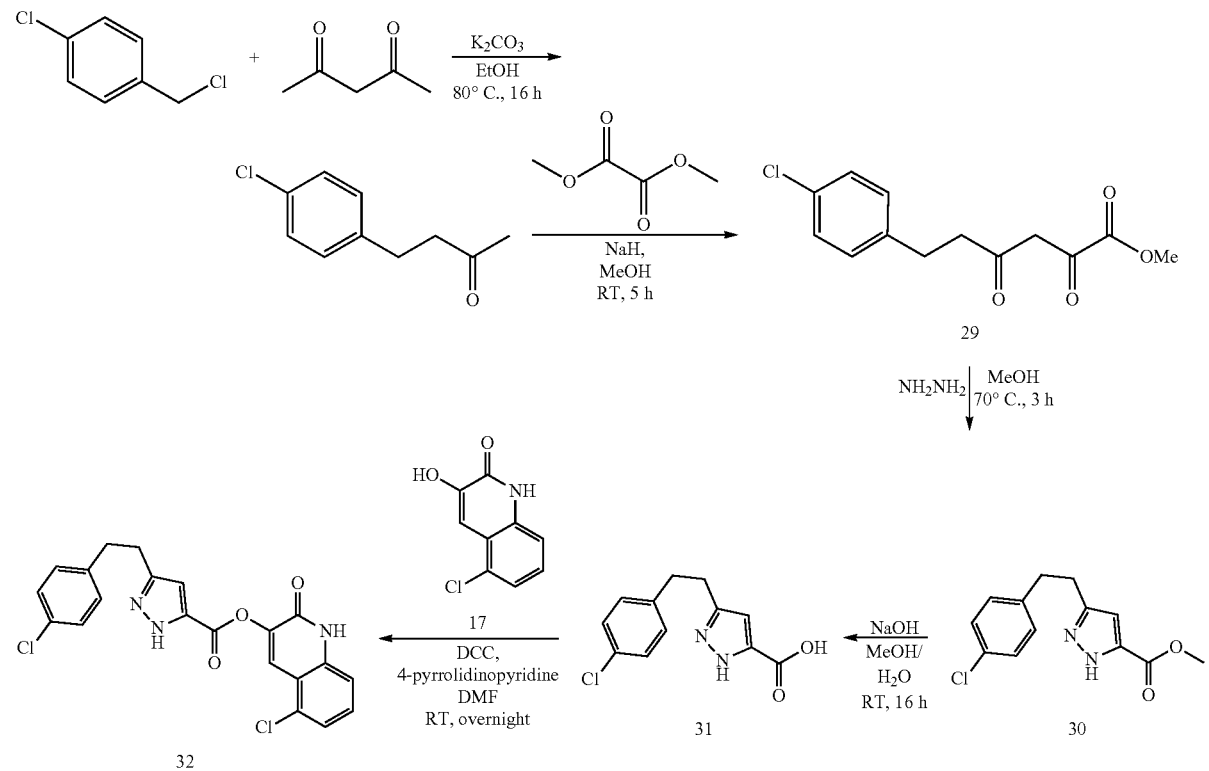

4-(4-Chlorophenyl) butan-2-one (28)

To an stirring solution of 1-chloro-4-(chloromethyl) benzene (22.0 g, 136.6 mmol) in ethanol (200 mL) was added potassium carbonate (19.0 g, 137.5 mmol) and pentane-2, 4-dione (14.4 g, 143.8 mmol). The resulting mixture was heated at 80° C. for 16 h. After the reaction was completed, the mixture was cooled to RT and then filtered. The filtrate was evaporated in vacuo. The residue was purified by flash column chromatography with ethyl acetate/petroleum ether (1:9) to afford 4-(4-chlorophenyl) butan-2-one (28) as a colorless solid (18.0 g, 72%). $^1$H NMR (CDC$_3$-d, 300 MHz) δ=7.32-7.24 (m, 2H), 7.20-7.10 (m, 2H), 2.95-2.85 (m, 2H), 2.83-2.71 (m, 2H), 2.17 (s, 3H). ESI-MS, m/z=183 [M+H]$^+$.

Methyl 6-(4-chlorophenyl)-2,4-dioxohexanoate (29)

To a solution of methanol (90 mL) was added sodium hydride (4.8 g, 201.3 mmol) in portions, then 4-(4-chlorophenyl) butan-2-one (28, 22.0 g, 120.5 mmol) and dimethyl oxalate (14.2 g, 120.3 mmol) was added to the mixture at RT. The resulting mixture was stirred for 5 h at RT. After the reaction was completed, the mixture was quenched with 1N HCl$_{(aq)}$. The mixture was evaporated in vacuo to remove most of the solvent. The residue was diluted with ethyl acetate, washed with brine, dried over anhydrous sodium sulfate and filtered. The filtrate was evaporated in vacuo. The residue was purified by flash column chromatography with petroleum ether to afford methyl 6-(4-chlorophenyl)-2,4-dioxohexanoate (29) as a yellow oil as a mixture (3.7 g, 11%). ESI-MS, m/z=269 [M+H]$^+$.

Methyl 3-(4-chlorophenethyl)-1H-pyrazole-5-carboxylate (30)

To a stirring solution of methyl 6-(4-chlorophenyl)-2,4-dioxohexanoate (29, 500.0 mg, 1.9 mmol) in methanol (6 mL) was added hydrazine (51 wt % aqueous solution) (0.1 mL, 2.1 mmol). The resulting mixture was heated at 70° C. for 3 h. After the reaction was completed, the mixture was evaporated in vacuo. The residue was purified by reverse phase flash column chromatography to afford methyl 3-(4-chlorophenethyl)-1H-pyrazole-5-carboxylate (30) as a white solid as a mixture (100.0 mg, 20%). ESI-MS, m/z=265 [M+H]$^+$.

3-(4-Chlorophenethyl)-1H-pyrazole-5-carboxylic acid (31)

To a mixture of methyl 3-(4-chlorophenethyl)-1H-pyrazole-5-carboxylate (30, 1.1 g, 4.2 mmol) in methanol (20 mL) was added sodium hydroxide (0.7 g, 16.7 mmol) and water (5 mL). The resulting mixture was stirred at RT for 16 h. After the reaction was completed, the pH value of the mixture was adjusted to 1 with 1N HCl$_{(aq)}$. The mixture was extracted with ethyl acetate, washed with brine, dried over anhydrous sodium sulfate and filtered. The filtrate was evaporated in vacuo. The residue was purified by Prep-HPLC to afford 3-(4-chlorophenethyl)-1H-pyrazole-5-carboxylic acid (31) as a white solid (0.9 g, 90%). $^1$H NMR (DMSO-d$_6$, 400 MHz) δ 12.97 (s, 2H), 7.34-7.32 (m, 2H), 7.24 (d, 2H, J=8.4 Hz), 6.48 (s, 1H), 2.95-2.87 (m, 4H). ESI-MS, m/z=250 [M+H]$^+$.

5-Chloro-2-oxo-1,2-dihydroquinolin-3-yl 3-(4-chlorophenethyl)-1H-pyrazole-5-carboxylate (32)

To a solution of 3-(4-chlorophenethyl)-1H-pyrazole-5-carboxylic acid (31, 250.0 mg, 1.0 mmol) in N, N-dimethylformamide (10 mL) was added 5-chloro-3-hydroxyquinolin-2(1H)-one (17, 292.5 mg, 1.5 mmol), N, N-dicyclohexylcarbodiimide (309.3 mg, 1.5 mmol) and 4-(pyrrolidin-1-yl) pyridine (27.7 mg, 0.2 mmol). The reaction mixture was stirred at RT overnight. After the reaction was completed, the mixture was diluted with water, extracted with dichloromethane, washed with brine, dried over anhydrous sodium sulfate and filtered. The filtrate was evaporated in vacuo. The residue was purified by flash column chromatography with methanol/dichloromethane (1:9) to afford 5-chloro-2-oxo-1,2-dihydroquinolin-3-yl 3-(4-chlorophenethyl)-1H-pyrazole-5-carboxylate (32) as a grey solid (18.9 mg, 4%). $^1$H NMR (DMSO-d$_6$, 300 MHz) δ=13.52 (s, 1H), 12.54 (s, 1H), 8.03 (s, 1H), 7.56-7.51 (m, 1H), 7.41-7.34 (m, 4H), 7.31-7.25 (m, 2H), 6.71 (s, 1H), 3.17-2.98 (m, 4H). ESI-MS, m/z=428 [M+H]$^+$.

Example 11: Synthesis of 5-chloro-2-oxo-1,2-dihydroquinolin-3-yl 3-(naphthalen-1-ylmethyl)-1H-pyrazole-5-carboxylate (39)

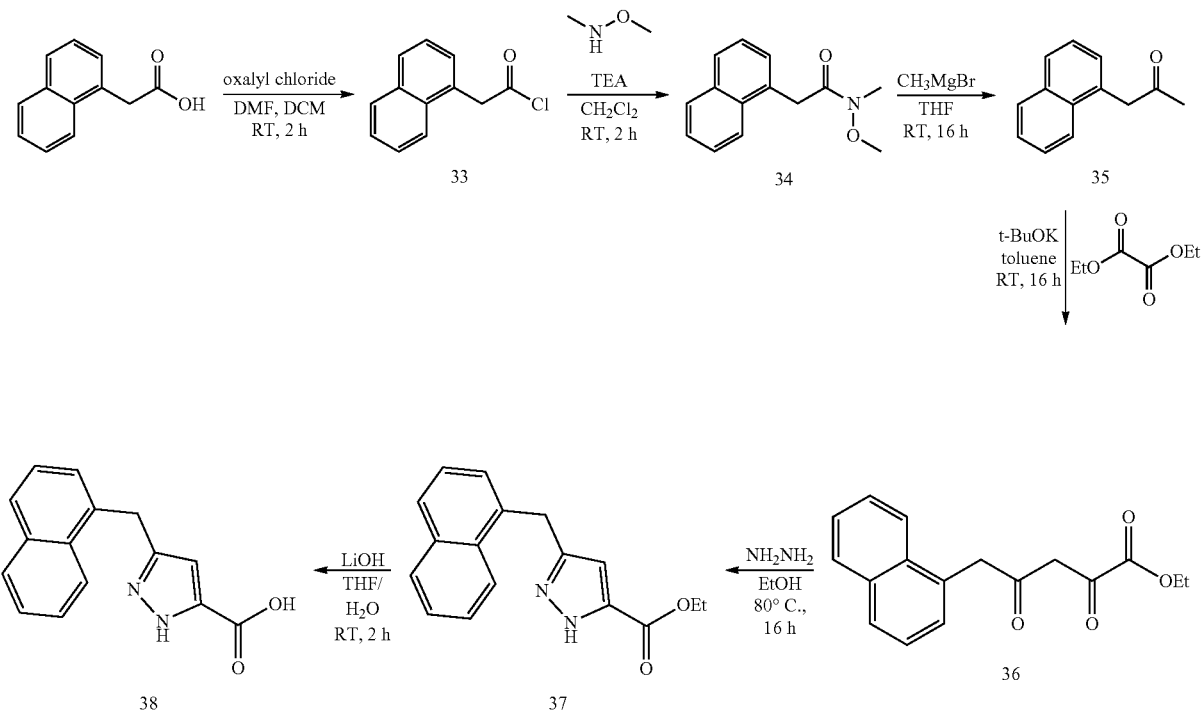

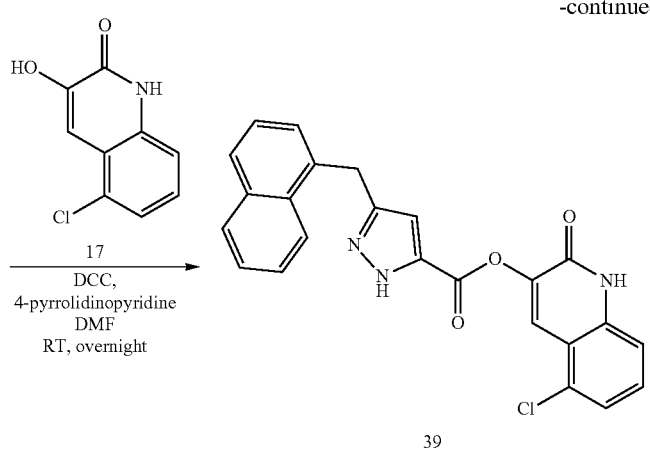

2-(Naphthalen-1-yl) acetyl chloride (33)

To a stirring solution of 2-(naphthalen-1-yl) acetic acid (18.0 g, 95.0 mmol) in dichloromethane (300 mL) and N,N-dimehtylformamide (0.5 mL) was added oxalyl chloride (8.5 mL, 100.0 mmol) dropwise at 0° C. The resulting solution was stirred for at RT for 2 h. The resulting mixture was concentrated under vacuum to afford 2-(naphthalen-1-yl) acetyl chloride (33) (21.0 g, crude) as a yellow oil.

N-Methoxy-N-methyl-2-(naphthalen-1-yl) acetamide (34)

To a mixture of methoxy(methyl) amine hydrochloride (6.0 g, 98.0 mmol), trimethylamine (20.0 mL, 149.0 mmol) and dichloromethane (200 mL) was added 2-(naphthalen-1-yl)acetyl chloride (33, 17.0 g, 83.0 mmol) in dichloromethane (50 mL) at 0° C. The resulting solution was stirred at RT for 2 h, and concentrated under vacuum. The residue was purified by flash column chromatography with ethyl acetate/petroleum ether (1:1) to afford N-methoxy-N-methyl-2-(naphthalen-1-yl) acetamide (34) as a yellow oil (7.0 g, 50%). ESI-MS, m/z=230 [M+H]$^+$.

1-(Naphthalen-1-yl) propan-2-one (35)

To a stirring solution of N-methoxy-N-methyl-2-(naphthalen-1-yl) acetamide (34, 7.0 g, 31.0 mmol) in tetrahydrofuran (150 mL) was added methyl magnesium bromide (60.0 mL, 1.0 M in tetrahydrofuran) dropwise at 0° C. The resulting solution was stirred for at RT for 16 h. The reaction was quenched by the addition of saturated NH$_4$Cl$_{(aq)}$ (100 mL), and extracted with ethyl acetate (2×300 mL). The combined organic layers were washed with brine, dried over anhydrous sodium sulfate and concentrated in vacuo. The residue was purified by flash column chromatography with ethyl acetate/petroleum ether (1:3) to afford 1-(naphthalen-1-yl) propan-2-one (35) as a yellow oil (3.5 g, 61%). ESI-MS, m/z=185 [M+H]$^+$.

Ethyl 5-(naphthalen-1-yl)-2,4-dioxopentanoate (36)

To a stirred solution of 1-(naphthalen-1-yl) propan-2-one (35, 3.0 g, 16.0 mmol) diethyl oxalate (3.0 g, 20.0 mmol) in toluene (100 mL) was added potassium tert-butoxide (1.5 g, 16.0 mmol) at 0° C. under N$_2$. The reaction mixture was stirred at 0° C. for 2 h and then allowed to warm to RT overnight. The solvent was removed and the residue was dissolved in water and neutralized to pH 2 with 1N HCl$_{(aq)}$ and extracted with ethyl acetate. The organic phase was combined and washed with brine, and dried over anhydrous sodium sulfate. The residue was purified by flash column chromatography with ethyl acetate/petroleum ether (1:1) to afford ethyl 5-(naphthalen-1-yl)-2,4-dioxopentanoate (36) as a yellow oil (1.5 g, 33%). ESI-MS, m/z=285 [M+H]$^+$.

Ethyl 3-(naphthalen-1-ylmethyl)-1H-pyrazole-5-carboxylate (37)

A mixture of hydrazine (51 wt % aqueous solution) (1.0 mL, 21.4 mmol), ethyl 5-(naphthalen-1-yl)-2,4-dioxopentanoate (36, 1.5 g, 5.3 mmol) in ethanol (50 mL) was stirred at 80° C. for 16 h. The reaction mixture was concentrated under vacuum, and the residue was purified by flash column chromatography with ethyl acetate/petroleum ether (1:1) to obtain ethyl 3-(naphthalen-1-ylmethyl)-1H-pyrazole-5-carboxylate (37) as a yellow solid (0.8 g, 57%). ESI-MS, m/z=281 [M+H]$^+$. 3-(Naphthalen-1-ylmethyl)-1H-pyrazole-5-carboxylic acid (38)

To a stirring solution of ethyl 3-(naphthalen-1-ylmethyl)-1H-pyrazole-5-carboxylate (37, 0.8 g, 2.9 mmol) in tetrahydrofuran (30 ml) was added the solution of lithium hydroxide (0.4 g, 14.5 mmol) in water (15 mL). The resulting solution was stirred at RT for 2 h. The resulting mixture was concentrated under vacuum, and then acidified to pH 1 with 10% HCl$_{(aq)}$. The white solid precipitated was collected by filtration and washed with water. The solid was further purified by Prep-HPLC to obtain 3-(naphthalen-1-ylmethyl)-1H-pyrazole-5-carboxylic acid (38) as a white solid (79.9 mg, 11%). $^1$H NMR (DMSO-d$_6$, 400 MHz) δ 13.11 (br s, 2H), 8.14-8.12 (m, 1H), 7.75-7.73 (m, 1H), 7.93-7.85 (m, 1H), 7.82-7.40 (m, 4H), 6.38 (s, 1H), 4.43 (s, 2H). ESI-MS, m/z=253 [M+H]$^+$.

5-Chloro-2-oxo-1,2-dihydroquinolin-3-yl 3-(naphthalen-1-ylmethyl)-1H-pyrazole-5-carboxylate (39)

To a solution of 3-(naphthalen-1-ylmethyl)-1H-pyrazole-5-carboxylic acid (38, 500.0 mg, 2.0 mmol) in N,N-dimethylformamide (10 mL) was added 5-chloro-3-hydroxyquinolin-2(1H)-one (17, 273.0 mg, 1.4 mmol), N,N-dicyclohexylcarbodiimide (1.9 g, 9.0 mmol) and 4-(pyrrolidin-1-yl)pyridine (110.0 mg, 0.8 mmol). The reaction mixture was stirred at RT overnight. After the reaction was completed, the mixture was diluted with water, extracted with dichloromethane, washed with brine, dried over anhydrous sodium sulfate and filtered. The filtrate was evaporated in vacuo. The residue was purified by flash column chromatography with methanol/dichloromethane (5:95) to afford 5-chloro-2-oxo-1,2-dihydroquinolin-3-yl 3-(naphthalen-1-ylmethyl)-1H-pyrazole-5-carboxylate (39) as a white solid (30.0 mg, 5%). $^1$H NMR (DMSO-d$_6$, 300 MHz) δ 13.73 (s, 1H), 12.52 (s, 1H), 8.16-7.86 (m, 4H), 7.61-7.32 (m, 7H), 6.57 (s, 1H), 4.53 (s, 2H). ESI-MS, m/z=430 [M+H]$^+$.

Example 12: Synthesis of 5-(((3,4-dichlorophenyl)thio) methyl)-2-oxo-1,2-dihydropyridin-3-yl 1H-pyrazole-5-carboxylate (47)

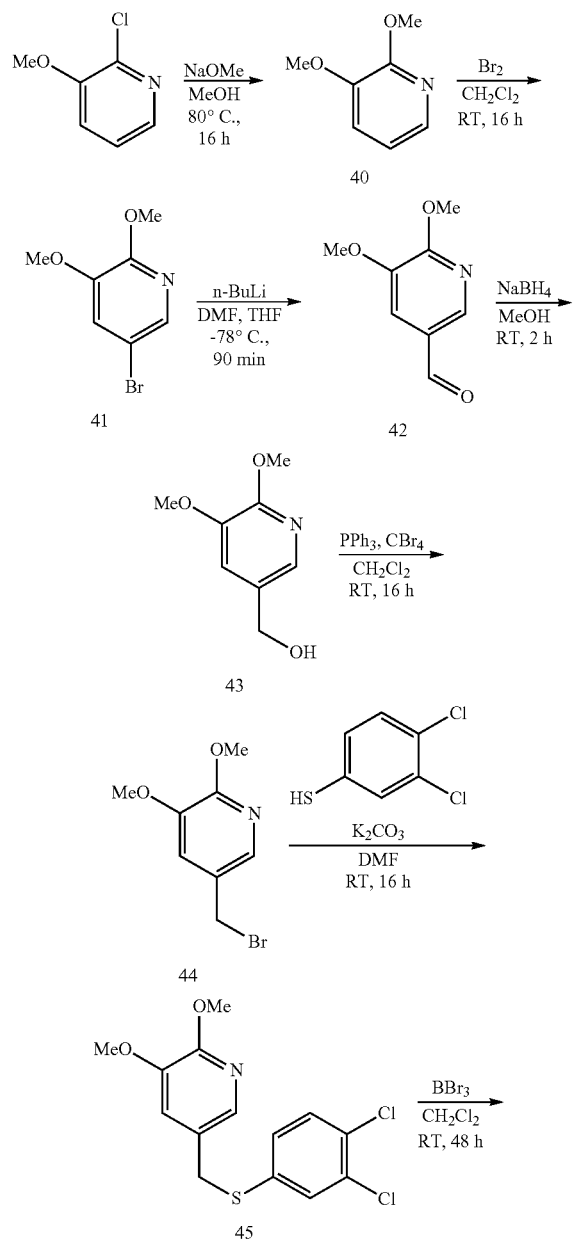

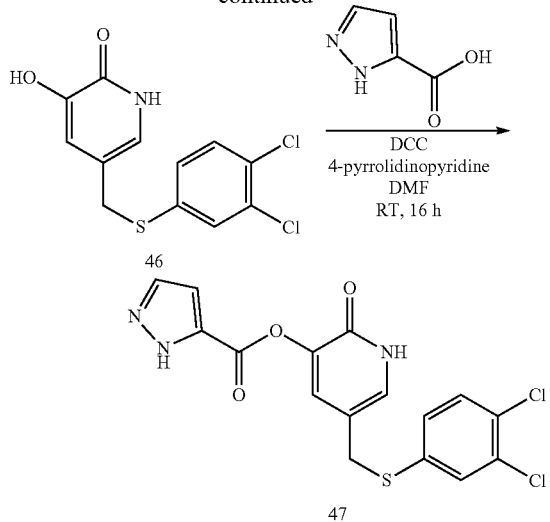

2,3-Dimethoxypyridine (40)

To a stirring solution of sodium methoxide (300.0 mL, 30% in methanol) was added 2-chloro-3-methoxypyridine (55.0 g, 383.1 mmol). The reaction mixture was stirred at 80° C. overnight. After the reaction was completed, the mixture was evaporated in vacuo. The residue was dissolved with ethyl acetate, washed with brine, dried over anhydrous sodium sulfate and filtered. The filtrate was evaporated in vacuo. The residue was purified by flash chromatogram with ethyl acetate/petroleum ether (1:5) to afford 2,3-dimethoxypyridine (40) as yellow oil (42.0 g, 79%). ESI-MS, m/z=140 [M+H]$^+$.

5-Bromo-2,3-dimethoxypyridine (41)

To a stirring solution of 2,3-dimethoxypyridine (40, 27.0 g, 194.0 mmol) in dichloromethane (200 mL) was added bromine (9.0 mL, 174.6 mmol). The reaction mixture was stirred at RT overnight. The pH value of the mixture was adjusted to 6 with saturated NaHCO$_{3(aq)}$. The mixture was extracted with dichloromethane (2×300 mL), washed with brine, dried over anhydrous sodium sulfate and filtered. The filtrate was evaporated in vacuo. The residue was purified by flash chromatogram with ethyl acetate/petroleum ether (1:5) to afford 5-bromo-2,3-dimethoxypyridine (41) as a yellow oil (22.0 g, 52%). ESI-MS, m/z=218 [M+H]$^+$.

5,6-Dimethoxynicotinaldehyde (42)

To a solution of 5-bromo-2,3-dimethoxypyridine (41, 21.7 g, 99.5 mmol) in anhydrous tetrahydrofuran (200 mL) was dropwise added n-butyl lithium (48.0 mL, 2.5 mol/L in hexane) at −78° C. under N$_2$. The mixture was stirred for at −78° C. for 1 h. Then N, N-dimethylformamide (16.2 mL) was added to the mixture at −78° C. The reaction mixture was stirred for another 30 min at −78° C. After the reaction was completed, the mixture was quenched by saturated NH$_4$Cl$_{(sat.)}$, extracted with ethyl acetate, washed with brine, dried over anhydrous sodium sulfate and filtered. The filtrate was evaporated in vacuo. The residue was purified by flash chromatogram with ethyl acetate/petroleum ether (1:3) to afford 5,6-dimethoxynicotinaldehyde (42) as a yellow solid (13.5 g, 81%). ESI-MS, m/z=168 [M+H]$^+$.

(5,6-Dimethoxypyridin-3-yl) methanol (43)

To a stirring solution of 5,6-dimethoxynicotinaldehyde (42, 21.0 g, 125.6 mmol) in methanol (200 mL) was added NaBH$_4$ (17.1 g, 452.0 mmol) in portions. The reaction mixture was stirred at RT for 2 h. After the reaction was completed, the mixture was quenched by saturated NH$_4$Cl$_{(sat.)}$. The mixture was extracted with ethyl acetate, washed by brine, dried over anhydrous sodium sulfate and filtered. The filtrate was evaporated in vacuo. The residue was purified by flash chromatogram with dichloromethane/methanol (9:1) to afford (5,6-dimethoxypyridin-3-yl) methanol (43) as a yellow solid (10.5 g, 49%). ESI-MS, m/z=170 [M+H]$^+$.

5-(Bromomethyl)-2,3-dimethoxypyridine (44)

To a solution of (5,6-dimethoxypyridin-3-yl) methanol (43, 10.3 g, 60.9 mmol) in dichloromethane (200 mL) was added triphenylphosphine (24.0 g, 91.5 mmol) at 0° C. under N$_2$. The mixture was stirred for 30 min at 0° C. Then tetrabromomethane (30.0 g, 91.3 mmol) was added to the mixture. The reaction mixture was stirred at RT overnight. The mixture was diluted with water, extracted with dichloromethane, washed with brine, dried over anhydrous sodium sulfate and filtered. The filtrate was evaporated in vacuo. The residue was purified by flash chromatogram with ethyl acetate/petroleum ether (1:5) to afford 5-(bromomethyl)-2,3-dimethoxypyridine (44) as a brown solid (6.6 g, 47%). ESI-MS, m/z=232 [M+H]$^+$.

5-(((3,4-Dichlorophenyl) thio) methyl)-2,3-dimethoxypyridine (45)

To a mixture of 5-(bromomethyl)-2,3-dimethoxypyridine (44, 540.0 mg, 2.3 mmol) and 3,4-dichlorobenzene-1-thiol (498.4 mg, 2.8 mmol) in N, N-dimethylforamide (10 mL) was added potassium carbonate (646.0 mg, 4.7 mmol). The mixture was stirred at RT overnight. The mixture was diluted with water, extracted with dichloromethane, washed with brine, dried over anhydrous sodium sulfate and filtered. The filtrate was evaporated in vacuo. The residue was purified by flash chromatogram with ethyl acetate/petroleum ether (3:7) to afford 5-(((3,4-dichlorophenyl) thio) methyl)-2,3-dimethoxypyridine (45) as a brown solid (640.0 mg, 83%). ESI-MS, m/z=330 [M+H]$^+$.

5-(((3,4-Dichlorophenyl) thio) methyl)-3-hydroxypyridin-2(1H)-one (46)

To a stirring solution of 5-(((3,4-dichlorophenyl) thio) methyl)-2,3-dimethoxypyridine (45, 330.0 mg, 1.0 mmol) in dichloromethane (10 mL) was added tribromoborane (10.0 mL, 1.0 M in dichloromethane). The reaction mixture was stirred at RT for 48 h. The resulting mixture was evaporated in vacuo. The pH value of the mixture was adjusted to 1 with 1N HCl$_{(aq)}$. The mixture was extracted with dichloromethane, washed with brine, dried over anhydrous sodium sulfate and filtered. The filtrate was evaporated in vacuo. The residue was purified by Prep-HPLC to afford 5-(((3,4-dichlorophenyl) thio) methyl)-3-hydroxypyridin-2(1H)-one (46) as a pink solid (132.6 mg, 44%). $^1$H NMR (DMSO-d$_6$, 300 MHz) δ 11.51 (s, 1H), 9.14 (s, 1H), 7.59 (d, J=2.4 Hz, 1H), 7.53 (d, J=8.4 Hz, 1H), 7.29 (dd, J=8.4, 2.4 Hz, 1H), 6.81 (s, 1H), 6.70 (d, J=2.4 Hz, 1H), 4.03 (s, 2H). ESI-MS, m/z=302 [M+H]$^+$.

5-(((3,4-Dichlorophenyl) thio) methyl)-2-oxo-1,2-dihydropyridin-3-yl 1H-pyrazole-5-carboxylate (47)

To a stirring solution of 5-(((3,4-dichlorophenyl) thio) methyl)-3-hydroxypyridin-2(1H)-one (46, 302.0 mg, 1.0 mmol) in N, N-dimethylformamide (15 mL) was added N, N-dicyclohexylcarbodiimide (309.0 mg, 1.5 mmol), 1H-pyrazole-5-carboxylic acid (168.0 mg, 1.5 mmol), 4-(pyrrolidin-1-yl) pyridine (30.0 mg, 0.2 mmol). The reaction mixture was stirred at RT overnight, diluted with water, and extracted with dichloromethane (2×50 mL). The organic layers were combined, washed with brine, dried over anhydrous sodium sulfate, and concentrated in vacuo. The residue was purified by flash column chromatography with methanol/dichloromethane (5:95), and then by Prep-HPLC to afford 5-(((3,4-dichlorophenyl) thio) methyl)-2-oxo-1,2-dihydropyridin-3-yl 1H-pyrazole-5-carboxylate (47) as a white solid (31.7 mg, 8%). $^1$H NMR (DMSO-d$_6$, 300 MHz) δ 13.71 (s, 1H), 11.96 (s, 1H), 7.96 (1, 1H), 7.64-7.48 (m, 3H), 7.35-7.30 (m, 2H), 6.90 (s, 1H), 4.13 (s, 2H). ESI-MS, m/z=396 [M+1]$^+$.

Example 13: Synthesis of 5-(((3,4-dichlorophenyl) thio) methyl)-2-oxo-1,2-dihydropyridin-3-yl 3-(4-chlorophenethyl)-1H-pyrazole-5-carboxylate (48)

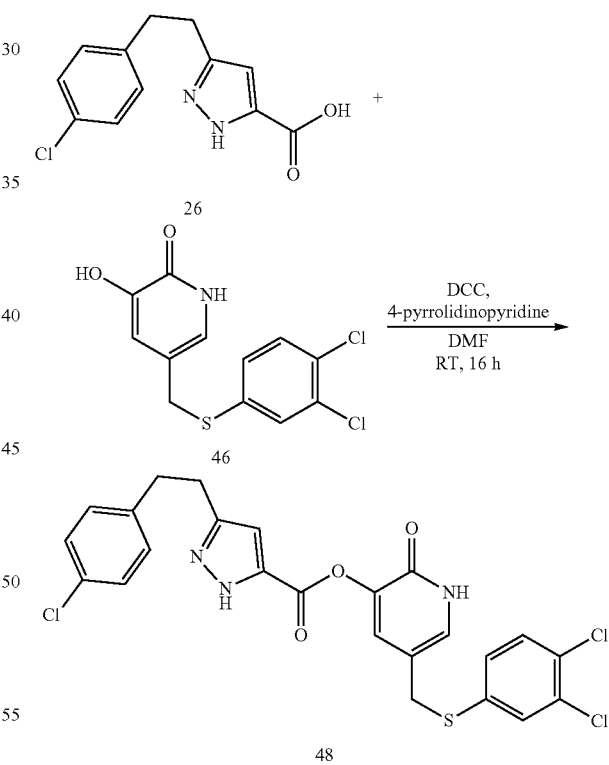

5-(((3,4-Dichlorophenyl) thio) methyl)-2-oxo-1,2-dihydropyridin-3-yl 3-(4-chlorophenethyl)-1H-pyrazole-5-carboxylate (48)

A mixture of 3-(4-chlorophenethyl)-1H-pyrazole-5-carboxylic acid (31, 200.0 mg, 0.8 mmol), N, N-dicyclohexylcarbodiimide (198.0 mg, 1.0 mmol), 5-(((3,4-dichlorophenyl) thio) methyl)-3-hydroxypyridin-2(1H)-one (46, 240.0 mg, 0.8 mmol) and 4-(pyrrolidin-1-yl) pyridine (24.0 mg, 0.2 mmol) in N, N-dimethylformamide (15 mL) was stirred at RT for 16 h. The resulting mixture was diluted with water, extracted with ethyl acetate, washed with brine, dried over anhydrous sodium sulfate and filtered. The filtrate was evaporated in vacuo. The residue was purified by flash chromatogram with dichloromethane/methanol (95:5) and then purified by Prep-HPLC under the following conditions: (column: SunFire Prep $C_{18}$ OBD column 19×150 mm 5 μm 10 nm; Mobile Phase A: water (0.1% formic acid), Mobile Phase B: acetonitrile; Flow rate: 25 mL/min; Gradient: 52% B to 77% B in 7 min; 254/220 nm; $R_t$: 6.82 min) to afford 5-(((3,4-dichlorophenyl) thio) methyl)-2-oxo-1,2-dihydropyridin-3-yl 3-(4-chlorophenethyl)-1H-pyrazole-5-carboxylate (48) as a white solid (60.0 mg, 14%). $^1$H NMR (DMSO-$d_6$, 300 MHz) δ 13.45 (s, 1H), 11.94 (s, 1H), 7.64 (d, J=1.8 Hz, 1H), 7.56 (d, J=8.4 Hz, 1H), 7.45 (s, 1H), 7.36-7.24 (m, 6H), 6.65 (s, 1H), 4.12 (s, 2H), 2.96 (s, 4H). ESI-MS, m/z=534 [M+H]$^+$.

Example 14: Synthesis of 5-(((3,4-dichlorophenyl) thio) methyl)-2-oxo-1,2-dihydropyridin-3-yl 3-phenethyl-1H-pyrazole-5-carboxylate (49)

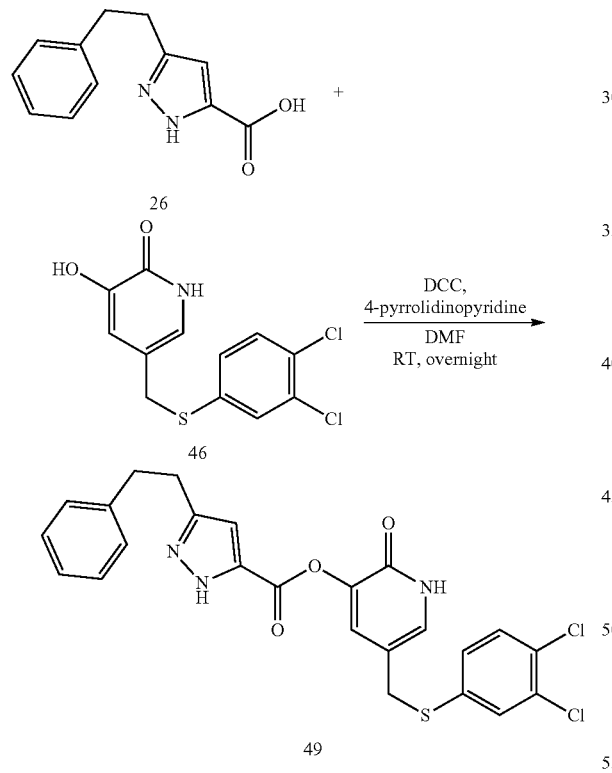

5-(((3,4-Dichlorophenyl) thio) methyl)-2-oxo-1,2-dihydropyridin-3-yl 3-phenethyl-1H-pyrazole-5-carboxylate (49)

To a stirring solution of 5-(((3,4-dichlorophenyl) methyl)-3-hydroxypyridin-2(1H)-one (46, 300.0 mg, 1.0 mmol) in N, N-dimethylformamide (15 mL) was added N, N-dicyclohexylcarbodiimide (248.0 mg, 1.2 mmol), 3-phenethyl-1H-pyrazole-5-carboxylic acid (26, 250.0 mg, 1.2 mmol), 4-(pyrrolidin-1-yl) pyridine (30.0 mg, 0.2 mmol). The reaction mixture was stirred at RT overnight, diluted with water, and extracted with dichloromethane (2×80 mL). The organic layers were combined, washed with brine, dried over anhydrous sodium sulfate, and concentrated in vacuo. The residue was purified by flash column chromatography with methanol/dichloromethane (5:95), then by Prep-HPLC with the following conditions (SunFire Prep $C_{18}$ OBD Column, 19×150 mm 5 μm 10 nm; mobile phase, water (0.1% formic acid) and acetonitrile (53% acetonitrile up to 70% in 7 min) to afford 5-(((3,4-dichlorophenyl) thio) methyl)-2-oxo-1,2-dihydropyridin-3-yl 3-phenethyl-1H-pyrazole-5-carboxylate (49) as a white solid (152.0 mg, 18%). $^1$H NMR (DMSO-$d_6$, 300 MHz) δ 13.47 (s, 1H), 11.94 (s, 1H), 7.64 (d, J=2.4 Hz, 1H), 7.57 (d, J=8.4 Hz, 1H), 7.46 (s, 1H), 7.35-7.17 (m, 7H), 6.65 (s, 1H), 4.13 (s, 2H), 2.97 (s, 4H). ESI-MS, m/z=500 [M+H]$^+$.

Example 15: Synthesis of 5-(((3,4-dichlorophenyl) thio) methyl)-2-oxo-1,2-dihydropyridin-3-yl 4-phenethyl-1H-pyrrole-2-carboxylate (50)

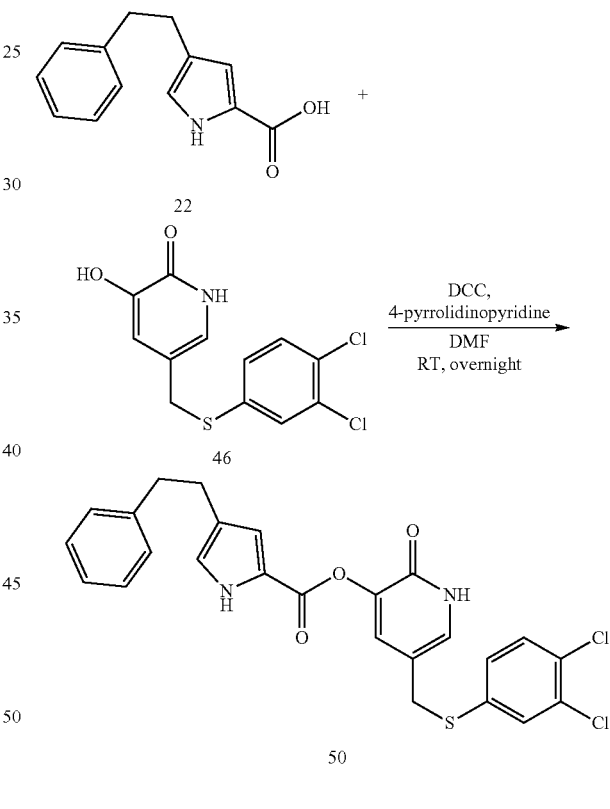

5-(((3,4-Dichlorophenyl) thio) methyl)-2-oxo-1,2-dihydropyridin-3-yl 4-phenethyl-1H-pyrrole-2-carboxylate (50)

To a stirring solution of 5-(((3,4-dichlorophenyl) thio) methyl)-3-hydroxypyridin-2(1H)-one (46, 450.0 mg, 1.5 mmol) in N, N-dimethylformamide (10 mL) was added N, N-dicyclohexylcarbodiimide (371.0 mg, 1.8 mmol), 4-phenethyl-1H-pyrrole-2-carboxylic acid (323.0 mg, 1.5 mmol), 4-(pyrrolidin-1-yl) pyridine (45.0 mg, 0.3 mmol). The reaction mixture was stirred at RT overnight, diluted with water, and extracted with dichloromethane (2×100 mL). The organic layers were combined, washed with brine, dried over anhydrous sodium sulfate, and concentrated in vacuo. The residue was purified by flash column chromatography with methanol/dichloromethane (5:95), and then by Prep-HPLC to afford 5-(((3,4-dichlorophenyl) thio) methyl)-2-oxo-1,2-dihydropyridin-3-yl 4-phenethyl-1H-pyrrole-2-carboxylate (50) as a white solid (97.9 mg, 13%). $^1$H NMR (DMSO-$d_6$, 300 MHz) δ 11.89 (s, 1H), 11.83 (s, 1H), 7.63 (d, J=2.4 Hz, 1H), 7.56 (d, J=8.4 Hz, 1H), 7.42 (s, 1H), 7.42-7.10 (m, 7H), 6.90 (d, J=2.1 Hz, 1H), 6.83 (s, 1H), 4.12 (s, 2H), 2.92-2.80 (m, 2H), 2.80-2.70 (m, 2H). ESI-MS, m/z=499 [M+1]$^+$.

Example 16: Synthesis of 6-(3,5-difluorophenethyl)-3-oxo-2,3-dihydropyridazin-4-yl 4-(4-chlorophenethyl)-1H-pyrrole-2-carboxylate (56)

extracted with ethyl acetate (3×500 mL) and the organic layers combined. Then the organic layer was washed with brine. The mixture was dried over anhydrous sodium sulfate and filtered. The residue was purified by flash column chromatography with ethyl acetate/petroleum ether (1:3) to afford 3-chlorobenzo[5, 6][1,4] dioxino[2,3-c] pyridazine (51) as a white solid (32.0 g, 50%). ESI-MS, m/z=221 [M+H]$^+$.

3-Vinylbenzo[5, 6][1,4] dioxino[2,3-c] pyridazine (52)

To a stirring solution of 3-chlorobenzo[5, 6][1,4] dioxino [2,3-c] pyridazine (51, 30.0 g, 136.0 mmol) in 1,4-dioxane (300 mL) was added 4, 4, 5,5-tetramethyl-2-vinyl-1, 3,2-dioxaborolane (25.2 g, 164.0 mmol), Pd(dppf)Cl$_2$ (20.1 g,

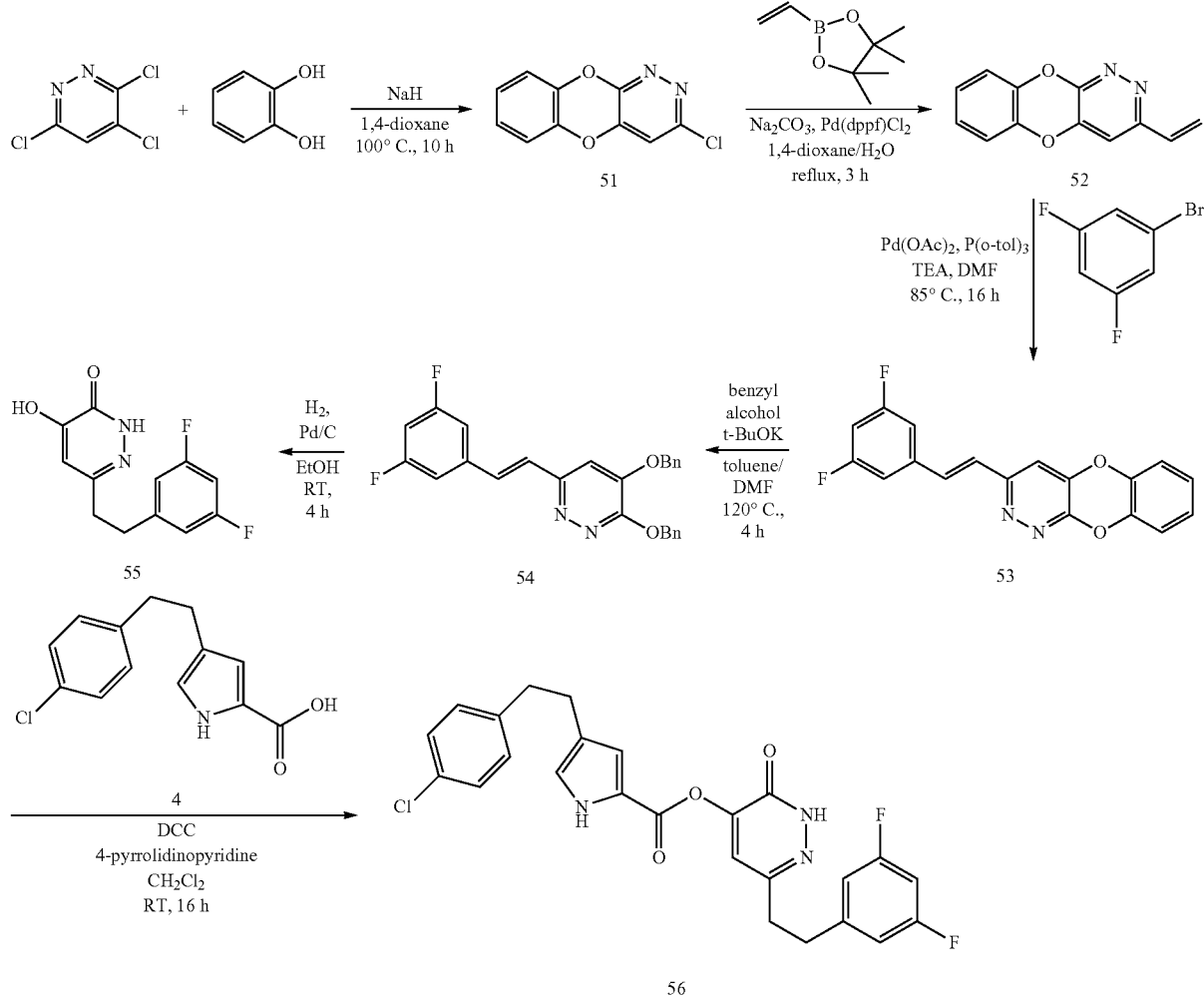

3-Chlorobenzo[5, 6] [1,4] dioxino[2,3-c] pyridazine (51)

To a suspension of sodium hydride (15.0 g, 375.0 mmol) in 1,4-dioxane (400 mL) was added benzene-1,2-diol (36.0 g, 320.0 mmol) and 3, 4,6-trichloropyridazine (60.0 g, 320.0 mmol) under the ice-bath. The resulting solution was stirred at 100° C. for 10 h before quenched by the addition of saturated NaCl$_{(aq)}$ (100 mL). The resulting solution was 27.6 mmol), sodium carbonate (28.8 g, 272.0 mmol), and water (60 mL). The resulting solution was heated to reflux for 3 h.

The resulting solution was extracted with ethyl acetate (3×500 mL) and the organic layers combined. Then the organic layer was washed with brine. The mixture was dried over anhydrous sodium sulfate and filtered. The residue was purified by flash column chromatography with ethyl acetate/ petroleum ether (1:3) to afford 3-vinylbenzo[5, 6][1,4]dioxino[2,3-c] pyridazine (52) as a white solid (18.0 g, 65%). ESI-MS, m/z=213 [M+H]⁺.

(E)-3-(3,5-Difluorostyryl) benzo[5, 6][1,4] dioxino [2,3-c] pyridazine (53)

To a stirring solution of 3-vinylbenzo[5, 6][1,4] dioxino [2,3-c] pyridazine (52, 15.0 g, 74.0 mmol) in N, N-dimethylforamide (100 mL) was added palladium diacetate (0.81 g, 3.6 mmol), tri(o-tolyl) phosphine (4.5 g, 15.0 mmol), triethylamine (144.0 g, 1410.0 mmol), and 1-bromo-3,5-difluorobenzene (17.1 g, 90.0 mmol). The resulting solution was stirred at 85° C. for 16 h. The resulting solution was extracted with ethyl acetate (3×500 mL) and the organic layers combined. Then the organic layer was washed with brine. The mixture was dried over anhydrous sodium sulfate and filtered. The residue was purified by flash column chromatography with ethyl acetate/petroleum ether (1:3) to afford (E)-3-(3,5-difluorostyryl)benzo[5, 6][1,4] dioxino[2,3-c] pyridazine (53) as an off-white solid (9.0 g, 41%). ESI-MS, m/z=325 [M+H]⁺.

(E)-3,4-Bis(benzyloxy)-6-(3,5-difluorostyryl) pyridazine (54)

To a solution of benzyl alcohol (6.0 g, 55.6 mmol) in toluene (50 mL), was added potassium tert-butoxide (6.4 g, 57.6 mmol) at 0° C. A solution of (E)-3-(3,5-difluorostyryl) benzo[5, 6][1,4] dioxino[2,3-c] pyridazine (53, 8.4 g, 26.0 mmol) in N, N-dimehtylforamide (30 mL) and toluene (10 mL) was added dropwise to the above reaction mixture at 0° C., and reaction mixture was heated to 120° C. for 4 h. The resulting solution was extracted with ethyl acetate (3×200 mL) and the organic layers combined. Then the organic layer was washed with brine. The mixture was dried over anhydrous sodium sulfate and filtered. The residue was purified by flash column chromatography with ethyl acetate/petroleum ether (1:1) to afford (E)-3,4-bis(benzyloxy)-6-(3,5-difluorostyryl) pyridazine (54) as a brown solid (2.8 g, 25%). ESI-MS, m/z=431 [M+H]⁺.

6-(3,5-Difluorophenethyl)-4-hydroxypyridazin-3 (2H)-one (55)

To a solution of (E)-3,4-bis(benzyloxy)-6-(3,5-difluorostyryl) pyridazine (54, 500.0 mg, 1.2 mmol) in ethanol (20 mL) was added 10% palladium on charcole (90.0 mg, 0.1 mmol). The mixture was stirred at RT for 4 h under hydrogen atmosphere. The reaction mixture was passed through a celite pad, and the filtrate was concentrated in vacuo to give a solid. The crude product was purified by Prep-HPLC to afford 6-(3, 5-difluorophenethyl)-4-hydroxypyridazin-3(2H)-one (55) as a pink solid (60.0 mg, 21%). ¹H NMR (DMSO-d₆, 300 MHz) δ 12.71 (s, 1H), 10.78 (br s, 1H), 7.06-6.96 (m, 3H), 6.60 (s, 1H), 6.88 (s, 1H), 2.97-2.89 (m, 2H), 2.81-2.77 (m, 2H). ESI-MS, m/z=253 [M+H]⁺.

6-(3, 5-Difluorophenethyl)-3-oxo-2, 3-dihydropyridazin-4-yl 4-(4-chlorophenethyl)-1H-pyrrole-2-carboxylate (56)

A solution of 6-(3, 5-difluorophenethyl)-4-hydroxypyridazin-3(2H)-one (55, 500.0 mg, 2.0 mmol), N, N-dicyclohexylcarbodiimide (450.0 mg, 2.2 mmol), 4-(4-chlorophenethyl)-1H-pyrrole-2-carboxylic acid (4, 550.0 mg, 4.4 mmol), 4-pyrrolidinopyridine (30.0 mg, 0.2 mmol) in dichloromethane (50 mL) was stirred at about 25° C. for 16 h. The resulting mixture was concentrated under vacuum. The crude product was purified by Prep-HPLC to afford 6-(3, 5-difluorophenethyl)-3-oxo-2, 3-dihydropyridazin-4-yl 4-(4-chlorophenethyl)-1H-pyrrole-2-carboxylate (56) as a white solid (48.7 mg, 5%). ¹H NMR (DMSO-d₆, 400 MHz) δ=13.17 (s, 1H), 11.99 (s, 1H), 7.49 (s, 1H), 7.33 (d, J=8.0 Hz, 2H), 7.26 (d, J=8.0 Hz, 2H), 7.17-6.98 (m, 3H), 6.97 (s, 1H), 6.89 (s, 1H), 2.99-2.84 (m, 6H), 2.76-2.72 (m, 2H). ESI-MS, m/z=484 [M+H]⁺.

Example 17: Synthesis of 6-(3, 5-difluorophenethyl)-3-oxo-2, 3-dihydropyridazin-4-yl 1H-pyrazole-5-carboxylate (57)

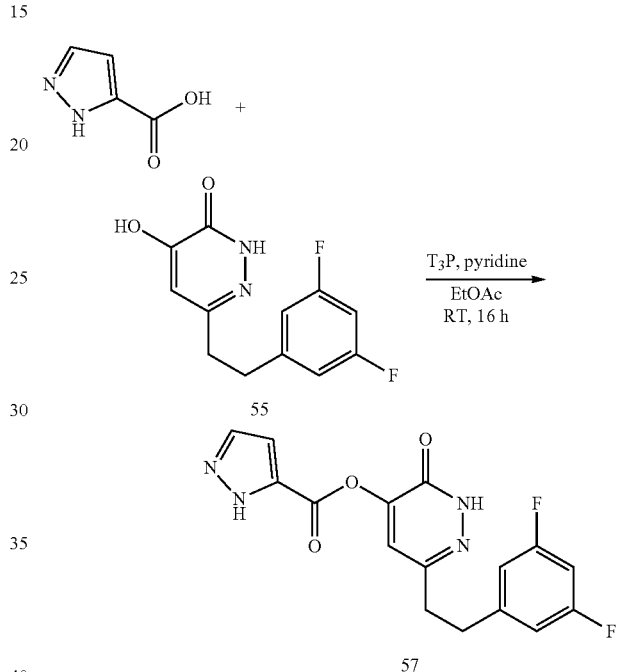

6-(3, 5-Difluorophenethyl)-3-oxo-2, 3-dihydropyridazin-4-yl 1H-pyrazole-5-carboxylate (57)

To a stirring solution of 6-(3, 5-difluorophenethyl)-4-hydroxypyridazin-3(2H)-one (55, 252.0 mg, 1.0 mmol) in ethyl acetate (10 mL) was added propylphosphonic anhydride solution (50% in ethyl acetate) (1.2 mL, 2.0 mmol), pyridine (1.0 mL, 12.2 mmol) and 1H-pyrazole-5-carboxylic acid (168.0 mg, 1.5 mmol). The reaction mixture was stirred at RT overnight, diluted with water and extracted with ethyl acetate. The combined organic layers were washed with brine, dried over anhydrous sodium sulfate, and concentrated in vacuo. The residue was purified by flash column chromatography with methanol/dichloromethane (5:95) and Prep-HPLC (column: SunFire Prep C₁₈ OBD column 19×150 mm 5 μm 10 nm; Mobile Phase A: water (0.1% formic acid), Mobile Phase B: acetonitrile; Flow rate: 25 mL/min; Gradient: 27% B to 47% B in 7 min; 254/220 nm; R_t: 6.88 min) to afford 6-(3, 5-difluorophenethyl)-3-oxo-2, 3-dihydropyridazin-4-yl 1H-pyrazole-5-carboxylate (57) as a white solid (10.2 mg, 3%). ¹H NMR (DMSO-d₆, 300 MHz) δ 13.22 (s, 1H), 12.70 (s, 1H), 7.55 (s, 1H), 7.13-6.92 (m, 4H), 6.59 (s, 1H), 3.05-2.85 (m, 2H), 2.85-2.69 (m, 2H). ESI-MS, m/z=347 [M+H]⁺.

Example 18: Synthesis of 6-(naphthalen-1-ylmethyl)-3-oxo-2, 3-dihydropyridazin-4-yl 3-phenethyl-1H-pyrazole-5-carboxylate (62)

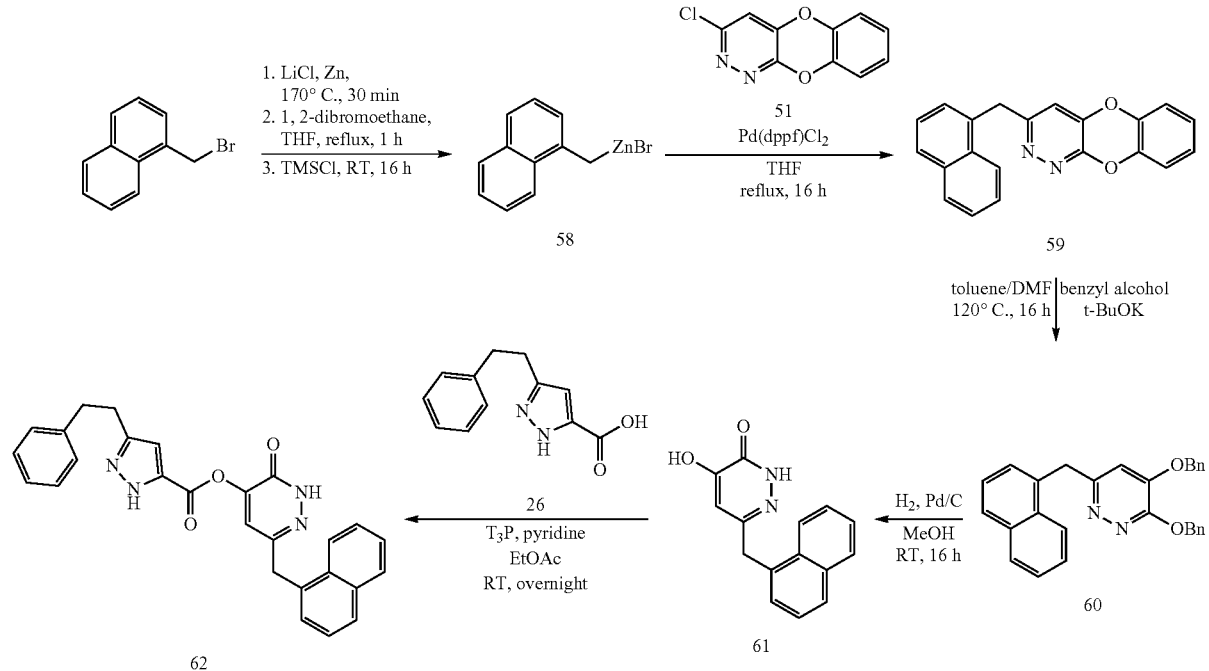
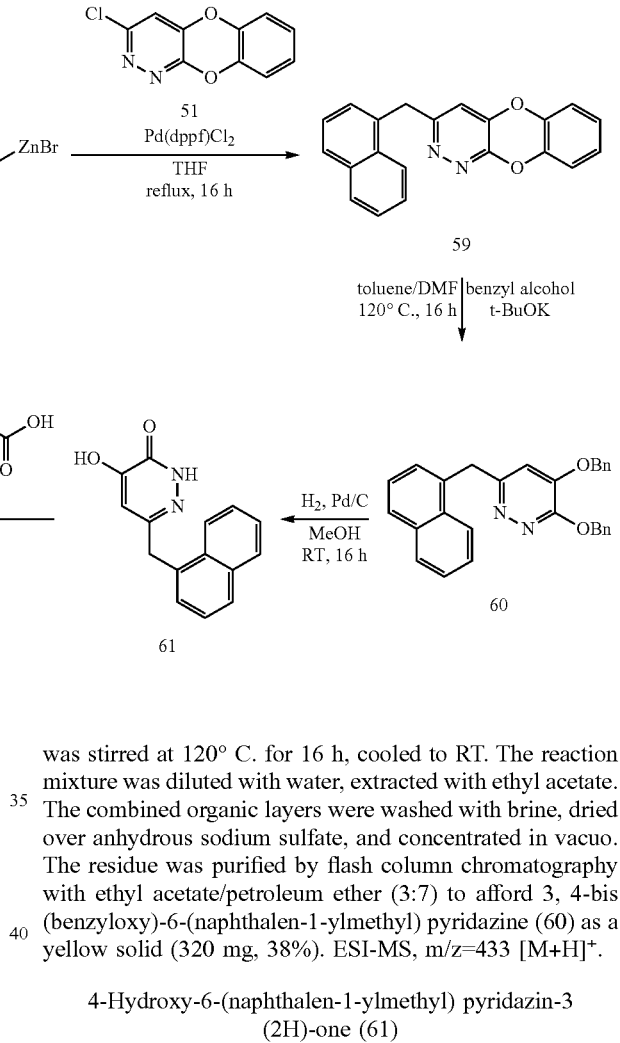

(Naphthalen-1-ylmethyl) zinc(II) bromide (58)

Under 3 mmHg, the mixture of lithium chloride (5.5 g, 130.0 mmol) and zinc (8.3 g, 130.0 mmol) was stirred at 170° C. for 0.5 h, cooled to RT, then 1,2-dibromoethane (1.9 g, 9.9 mmol) in tetrahydrofuran (100 mL) was slowly added and it was refluxed for 1 h, re-cooled to RT, chlorotrimethylsilane (1.1 g, 9.9 mmol) was added and the mixture was stirred for another 1 h, 1-(bromomethyl) naphthalene (11.0 g, 49.8 mmol) was added and it was stirred for 1 h. After filtration, the filtrate was directly used for the next step without further purification.

3-(Naphthalen-1-ylmethyl) benzo[5, 6][1, 4]dioxino[2, 3-c] pyridazine (59)

To the mixture of (naphthalen-1-ylmethyl) zinc(II) bromide (58) from last step was added 3-chlorobenzo[5, 6][1, 4]dioxino[2, 3-c] pyridazine (51, 2.8 g, 12.5 mmol), Pd(dppf)Cl$_2$ (1.5 g, 2.1 mmol). The mixture was refluxed overnight under N$_2$. The resulting mixture was diluted with water, and extracted with ethyl acetate. The combined organic layers were washed with brine, dried over anhydrous sodium sulfate, and concentrated in vacuo. The residue was purified by flash column chromatography with ethyl acetate/petroleum ether (1:5) to afford 3-(naphthalen-1-ylmethyl) benzo[5, 6][1, 4] dioxino[2, 3-c] pyridazine (59) as a yellow solid (632.0 mg, 16%). $^1$H NMR (DMSO-d$_6$, 300 MHz) δ 8.24-8.17 (m, 1H), 7.97-7.91 (m, 1H), 7.88-7.83 (m, 1H), 7.59-7.45 (m, 4H), 7.16-7.10 (m, 2H), 7.08-6.98 (m, 3H), 4.59 (s, 2H). ESI-MS, m/z=327 [M+H]$^+$.

3,4-Bis(benzyloxy)-6-(naphthalen-1-ylmethyl) pyridazine (60)

To the mixture of 3-(naphthalen-1-ylmethyl) benzo[5, 6][1, 4]dioxino[2, 3-c]pyridazine (59, 632.0 mg, 1.9 mmol) in N, N-dimethylformamide (10 mL) and toluene (20 mL) was added potassium tert-butoxide (868.0 mg, 7.7 mmol) and benzyl alcohol (837.0 mg, 7.7 mmol). The reaction mixture was stirred at 120° C. for 16 h, cooled to RT. The reaction mixture was diluted with water, extracted with ethyl acetate. The combined organic layers were washed with brine, dried over anhydrous sodium sulfate, and concentrated in vacuo. The residue was purified by flash column chromatography with ethyl acetate/petroleum ether (3:7) to afford 3, 4-bis (benzyloxy)-6-(naphthalen-1-ylmethyl) pyridazine (60) as a yellow solid (320 mg, 38%). ESI-MS, m/z=433 [M+H]$^+$.

4-Hydroxy-6-(naphthalen-1-ylmethyl) pyridazin-3(2H)-one (61)

To a solution of 3, 4-bis(benzyloxy)-6-(naphthalen-1-ylmethyl) pyridazine (60, 330.0 mg, 0.8 mmol) in methanol (10 mL) was added 10% palladium on charcoal (100.0 mg, 0.1 mmol), the reaction mixture was stirred at RT for 16 h under the atmosphere of H$_2$. The catalyst was filtered off and the filtrate was concentrated under vacuum. The residue was purified by flash column chromatography with dichloromethane/methanol (95:5) to afford 4-hydroxy-6-(naphthalen-1-ylmethyl) pyridazin-3(2H)-one (61) as a yellow solid (150.0 mg, 78%). $^1$H NMR (DMSO-d$_6$, 300 MHz) δ 12.68 (s, 1H), 8.13-8.06 (m, 1H), 7.96-7.89 (m, 1H), 7.83 (dd, J=5.7, 3.8 Hz, 1H), 7.59-7.43 (m, 4H), 6.41 (s, 1H), 4.26 (s, 2H). ESI-MS, m/z=253 [M+H]$^+$.

6-(Naphthalen-1-ylmethyl)-3-oxo-2, 3-dihydropyridazin-4-yl 3-phenethyl-1H-pyrazole-5-carboxylate (62)

To a solution of 4-hydroxy-6-(naphthalen-1-ylmethyl) pyridazin-3(2H)-one (61, 500.0 mg, 2.0 mmol) in ethyl acetate (10 mL) was added propylphosphonic anhydride solution (50% in ethyl acetate) (1.2 mL, 2.0 mmol), pyridine (1.0 mL, 12.2 mmol) and 3-phenethyl-1H-pyrazole-5-carboxylic acid (26, 428.0 mg, 2.0 mmol). The reaction mixture was stirred at RT overnight. The mixture was diluted with water, extracted with ethyl acetate, washed with brine, dried over anhydrous sodium sulfate and filtered. The filtrate was evaporated in vacuo. The residue was purified by flash column chromatography with methanol/dichloromethane (5:95) and then purified by Prep-HPLC (column: XBridge Prep $C_{18}$ OBD column 19×150 mm 5 μm C0013; Mobile Phase A: water (0.1% formic acid), Mobile Phase B: acetonitrile; Flow rate: 25 mL/min; Gradient: 45% B to 67% B in 7 min; 254/220 nm) to afford 6-(naphthalen-1-ylmethyl)-3-oxo-2, 3-dihydropyridazin-4-yl 3-phenethyl-1H-pyrazole-5-carboxylate (62) as an off-white solid (50.5 mg, 5%). $^1$H NMR (DMSO-$d_6$, 300 MHz) δ 13.54 (s, 1H), 13.24 (s, 1H), 8.15-8.12 (m, 1H), 7.97-7.93 (m, 1H), 7.88-7.84 (m, 1H), 7.60-7.44 (m, 5H), 7.31-7.16 (m, 5H), 6.65 (s, 1H), 4.48 (s, 2H), 2.96 (s, 4H). ESI-MS, m/z=451 [M+H]$^+$.

Example 19: Synthesis of 6-(naphthalen-1-ylmethyl)-3-oxo-2, 3-dihydropyridazin-4-yl 3-(3-chlorophenethyl)-1H-pyrazole-5-carboxylate (67)

Ethyl 6-(3-chlorophenyl)-2, 4-dioxohexanoate (64)

To a solution of sodium hydride (5.6 g, 232.0 mmol) in ethanol (150 mL) was added a mixture of 4-(3-chlorophenyl) butan-2-one (63, 19.6 g, 107.3 mmol) and diethyl oxalate (15.7 g, 107.4 mmol). The resulting mixture was stirred at RT for 5 h. After the reaction was completed, the mixture was cooled to RT. The pH value of the mixture was adjusted to 1 with 1N HCl$_{(aq)}$. The mixture was diluted with water, extracted with ethyl acetate, washed with brine, dried over anhydrous sodium sulfate and filtered. The filtrate was evaporated in vacuo. The residue was purified by flash column chromatography with petroleum ether to afford ethyl 6-(3-chlorophenyl)-2, 4-dioxohexanoate (64) as a yellow oil (17.9 g, 59%). ESI-MS, m/z=283 [M+H]$^+$.

Ethyl 3-(3-chlorophenethyl)-1H-pyrazole-5-carboxylate (65)

To a solution of 6-(3-chlorophenyl)-2, 4-dioxohexanoate (64, 17.2 g, 60.8 mmol) in ethanol (200 mL), was added

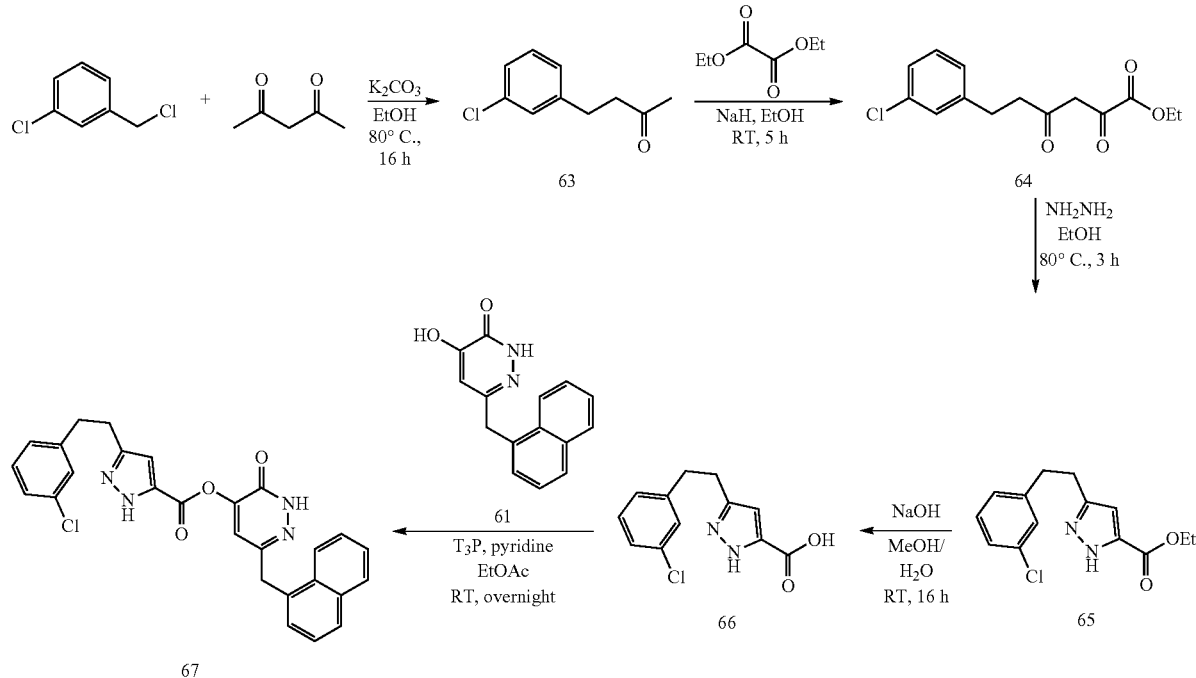

4-(3-Chlorophenyl) butan-2-one (63)

A mixture of 1-chloro-3-(chloromethyl) benzene (49.0 g, 304.3 mmol), pentane-2, 4-dione (30.6 g, 304.3 mmol) and potassium carbonate (42.3 g, 304.3 mmol) in ethanol (500 mL) was heated at 80° C. for 16 h. After the reaction was completed, the mixture was cooled to RT. The mixture was filtered. The filtrate was evaporated in vacuo. The residue was purified by flash column chromatography with ethyl acetate/petroleum ether (1:9) to afford 4-(3-chlorophenyl) butan-2-one (63) as yellow oil (20.0 g, 27%). ESI-MS, m/z=183 [M+H]$^+$.

hydrazine (51 wt % aqueous solution) (13.0 mL, 213.1 mmol). The resulting mixture was heated at 80° C. for 3 h. After the reaction was completed, the mixture was cooled to RT and then evaporated in vacuo. The residue was purified by recrystallization with ethanol/ethyl acetate/petroleum ether (1:10:1) to afford ethyl 3-(3-chlorophenethyl)-1H-pyrazole-5-carboxylate (65) as a white solid (15.6 g, 90%). ESI-MS, m/z=279 [M+H]$^+$.

3-(3-Chlorophenethyl)-1H-pyrazole-5-carboxylic acid (66)

To a solution of ethyl 3-(3-chlorophenethyl)-1H-pyrazole-5-carboxylate (65, 1.0 g, 3.6 mmol) in methanol (20 mL), was added sodium hydroxide (288.0 mg, 7.2 mmol) in water (3 mL). The resulting mixture was stirred at RT for 16 h. After the reaction was completed, the pH value of the mixture was adjusted to 1 with 1N HCl$_{(aq)}$. The mixture was diluted with water, extracted with ethyl acetate, washed with brine, dried over anhydrous sodium sulfate and filtered. The filtrate was evaporated in vacuo to afford 3-(3-chlorophenethyl)-1H-pyrazole-5-carboxylic acid (66) as a white solid (700 mg, 78%). $^1$H NMR (DMSO-d$_6$, 300 MHz) δ 12.96 (s, 2H), 7.33-7.17 (m, 4H), 6.48 (s, 1H), 2.95-2.87 (m, 4H). ESI-MS, m/z=250 [M+H]$^+$.

6-(Naphthalen-1-ylmethyl)-3-oxo-2, 3-dihydropyridazin-4-yl 3-(3-chlorophenethyl)-1H-pyrazole-5-carboxylate (67)

To a stirring solution of 4-hydroxy-6-(naphthalen-1-ylmethyl) pyridazin-3(2H)-one (61, 500.0 mg, 2.0 mmol) in ethyl acetate (10 mL) was added propylphosphonic anhydride solution (50% in ethyl acetate) (1.2 mL, 2.0 mmol), pyridine (1.0 mL, 12.2 mmol) and 3-(3-chlorophenethyl)-1H-pyrazole-5-carboxylic acid (66, 500.0 mg, 2.0 mmol). The reaction mixture was stirred at RT overnight. The mixture was diluted with water, extracted with ethyl acetate, washed with brine, dried over anhydrous sodium sulfate and filtered. The filtrate was evaporated in vacuo. The residue was purified by flash column chromatography with methanol/dichloromethane (5:95) and then purified by Prep-HPLC (column: XBridge Prep C$_{18}$ OBD column 19×150 mm 5 μm C0013; Mobile Phase A: water (0.1% formic acid), Mobile Phase B: acetonitrile; Flow rate: 25 mL/min; Gradient: 45% B to 65% B in 10 min; 254/220 nm) to afford 6-(naphthalen-1-ylmethyl)-3-oxo-2, 3-dihydropyridazin-4-yl 3-(3-chlorophenethyl)-1H-pyrazole-5-carboxylate (67) as a light yellow solid (114.2 mg, 12%). $^1$H NMR (DMSO-d$_6$, 300 MHz) δ 13.54 (s, 1H), 13.24 (s, 1H), 8.15-8.12 (m, 1H), 7.97-7.84 (m, 2H), 7.63-7.50 (m, 5H), 7.49-7.17 (m, 4H), 6.67 (s, 1H), 4.43 (s, 2H), 2.97 (s, 4H). ESI-MS, m/z=485 [M+H].

Example 20: Synthesis of 6-(naphthalen-1-ylmethyl)-3-oxo-2, 3-dihydropyridazin-4-yl 3-(4-fluorophenethyl)-1H-pyrazole-5-carboxylate (72)

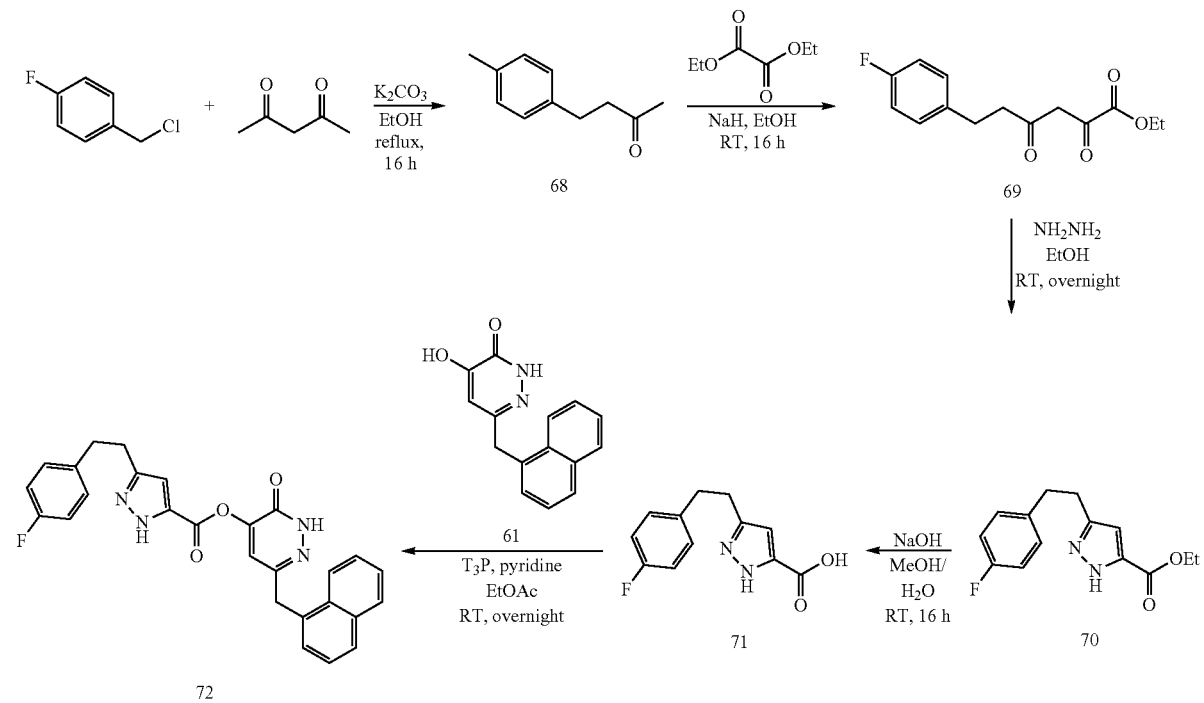

4-(4-Fluorophenyl) butan-2-one (68)

A mixture of 1-(chloromethyl)-4-fluorobenzene (30.0 g, 207.5 mmol), pentane-2, 4-dione (20.8 g, 207.8 mmol) and potassium carbonate (28.8 g, 208.4 mmol) in ethanol (200 mL) was refluxed for 16 h. The resulting mixture was cooled to RT and filtered. The filtrate was evaporated in vacuo. The residue was purified by flash column chromatography with ethyl acetate/petroleum ether (6:94) to afford 4-(4-fluorophenyl) butan-2-one (68) as light yellow oil (21.0 g, 61%). ESI-MS, m/z=167 [M+H]$^+$.

Ethyl 6-(4-fluorophenyl)-2,4-dioxohexanoate (69)

To an ice-cooled solution of ethanol (100 mL) was added sodium hydride (6.6 g, 164.5 mmol) in portions. Then a mixture of 4-(4-fluorophenyl) butan-2-one (68, 21.0 g, 126.4 mmol) and diethyl oxalate (18.5 g, 126.6 mmol) was added to the mixture at the same temperature. The resulting mixture was stirred at RT overnight. The pH value of the resulting mixture was adjusted to 1 with 1N HCl$_{(aq)}$. Most of the solvent was removed under vacuum. The residue mixture was extracted with ethyl acetate, washed with brine, dried over anhydrous sodium sulfate and filtered. The filtrate was evaporated in vacuo. The residue was purified by flash column chromatography with ethyl acetate/petroleum ether (1:9) to afford ethyl 6-(4-fluorophenyl)-2,4-dioxohexanoate (69) as yellow oil (24.3 g, 72%). ESI-MS, m/z=267 [M+H]$^+$.

Ethyl 3-(4-fluorophenethyl)-1H-pyrazole-5-carboxylate (70)

To a solution of ethyl 6-(4-fluorophenyl)-2, 4-dioxohexanoate (69, 24.3 g, 91.3 mmol) in ethanol (200 mL) was added hydrazine (51 wt % aqueous solution) (14.0 mL, 229.5 mmol). The resulting mixture was heated to reflux for 3 h. After the reaction was completed, the mixture was evaporated in vacuo. The residue was purified by recrystallization with ethanol/ethyl acetate/petroleum ether (1:8:1) to afford ethyl 3-(4-fluorophenethyl)-1H-pyrazole-5-carboxylate (70) as a white solid (20.0 g, 84%). ESI-MS, m/z=263 [M+H]$^+$.

3-(4-Fluorophenethyl)-1H-pyrazole-5-carboxylic acid (71)

To a solution of ethyl 3-(4-fluorophenethyl)-1H-pyrazole-5-carboxylate (70, 100.0 mg, 0.4 mmol) in methanol (5 mL) was added a solution of sodium hydroxide (836.0 mg, 20.9 mmol) in water (3 mL). The resulting mixture was stirred at RT for 16 h. The resulting mixture was evaporated in vacuo. The pH value of the mixture was adjusted to 1 with 1N HCl$_{(aq)}$. The mixture was extracted with ethyl acetate, washed with brine, dried over anhydrous sodium sulfate and filtered. The filtrate was evaporated in vacuo. The residue was purified by Prep-HPLC with the condition (column: SunFire Prep C$_{18}$ OBD column 19×150 mm 5 μm 10 nm; Mobile Phase A: water (0.1% formic acid), Mobile Phase B: acetonitrile; Flow rate: 25 mL/min; Gradient: 15% B to 55% B in 7 min; 254/220 nm; R$_t$: 6.22 min) to afford 3-(4-fluorophenethyl)-1H-pyrazole-5-carboxylic acid (71) as a white solid (40.0 mg, 42%). $^1$H NMR (DMSO-d$_6$, 300 MHz) δ 12.96 (s, 2H), 7.27-7.22 (m, 2H), 7.14-7.06 (m, 2H), 6.47 (s, 1H), 2.93-2.85 (m, 4H). ESI-MS, m/z=235 [M+H]$^+$.

6-(Naphthalen-1-ylmethyl)-3-oxo-2, 3-dihydropyridazin-4-yl 3-(4-fluorophenethyl)-1H-pyrazole-5-carboxylate (72)

To a solution of 4-hydroxy-6-(naphthalen-1-ylmethyl)pyridazin-3(2H)-one (61, 300.0 mg, 1.2 mmol) in ethyl acetate (10 mL) was added propylphosphonic anhydride solution (50% in ethyl acetate) (1.0 mL, 1.7 mmol), pyridine (0.8 mL, 9.8 mmol) and 3-(4-fluorophenethyl)-1H-pyrazole-5-carboxylic acid (71, 278.6 mg, 1.2 mmol). The reaction mixture was stirred at RT overnight. After the reaction was completed, the mixture was diluted with water, extracted with ethyl acetate, washed with brine, dried over anhydrous sodium sulfate and filtered. The filtrate was evaporated in vacuo. The residue was purified by flash column chromatography with methanol/dichloromethane (5:95) and then purified by Prep-HPLC (column: XBridge Prep C$_{18}$ OBD column 19×150 mm 5 m C0013; Mobile Phase A: water (0.1% formic acid), Mobile Phase B: acetonitrile; Flow rate: 25 mL/min; Gradient: 45% B to 66% B in 7 min; 254/220 nm) to afford 6-(naphthalen-1-ylmethyl)-3-oxo-2,3-dihydropyridazin-4-yl 3-(4-fluorophenethyl)-1H-pyrazole-5-carboxylate (72) as an off-white solid (114.2 mg, 12%). $^1$H NMR (DMSO-d$_6$, 300 MHz) δ 13.53 (s, 1H), 13.23 (s, 1H), 8.15-8.11 (m, 1H), 7.97-7.92 (m, 1H), 7.88-7.84 (m, 1H), 7.60-7.44 (m, 5H), 7.27-7.23 (m, 2H), 7.13-7.07 (m, 2H), 6.65 (s, 1H), 4.43 (s, 2H), 2.94 (s, 4H). ESI-MS, m/z=469 [M+H]$^+$.

Example 21: Synthesis of 6-(naphthalen-1-ylmethyl)-3-oxo-2, 3-dihydropyridazin-4-yl 3-benzyl-1H-pyrazole-5-carboxylate (77)

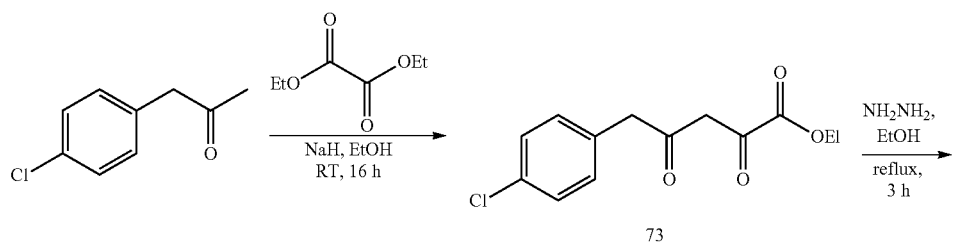

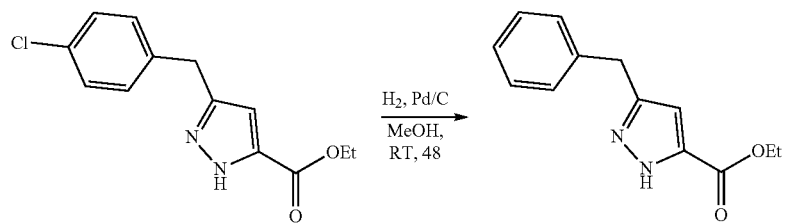

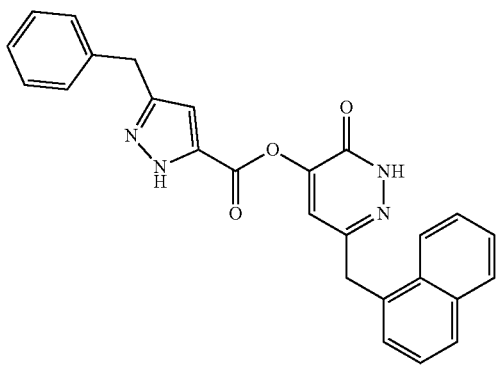
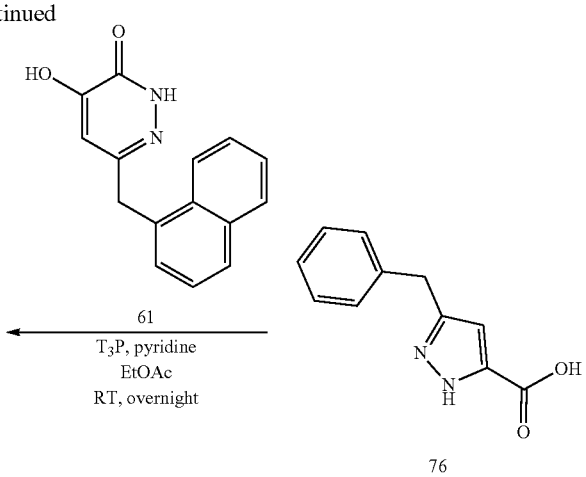

Ethyl 5-(4-chlorophenyl)-2, 4-dioxopentanoate (73)

To an ice cooled solution of ethanol (500 mL) was added sodium hydride (15.6 g, 650.0 mmol) in portions. Then the mixture of 1-(4-chlorophenyl) propan-2-one (50.0 g, 296.5 mmol) and diethyl oxalate (43.5 g, 297.3 mmol) was added to the mixture. The resulting mixture was stirred at RT for 16 h. After the reaction was completed, the pH value of the mixture was adjusted to 1 with 1N $HCl_{(aq)}$. The mixture was diluted with water, extracted with ethyl acetate, washed with brine, dried over anhydrous sodium sulfate and filtered. The filtrate was evaporated in vacuo. The residue was purified by flash column chromatography with ethyl acetate/petroleum ether (3:7) to afford ethyl 5-(4-chlorophenyl)-2, 4-dioxopentanoate (73) as yellow oil (59.0 g, 74%). ESI-MS, m/z=269 $[M+H]^+$.

Ethyl 3-(4-chlorobenzyl)-1H-pyrazole-5-carboxylate (74)

To a solution of ethyl 5-(4-chlorophenyl)-2, 4-dioxopentanoate (73, 59.0 g, 219.6 mmol) in ethanol (260 mL) was added hydrazine (51 wt % aqueous solution) (11.0 mL, 180.3 mmol). The resulting mixture was heated to reflux for 3 h. After the reaction was completed, the mixture was evaporated in vacuo. The residue was purified by recrystallization with ethanol/ethyl acetate/PE (1:8:1) to afford ethyl 3-(4-chlorobenzyl)-1H-pyrazole-5-carboxylate (74) as an off-white solid (32.0 g, 55%). ESI-MS, m/z=265 $[M+H]^+$.

Ethyl 3-benzyl-1H-pyrazole-5-carboxylate (75)

To a solution of ethyl 3-(4-chlorobenzyl)-1H-pyrazole-5-carboxylate (74, 5.0 g, 18.9 mmol) in methanol (150 mL) was added 10% Pd/C (1.2 g, 1.1 mmol). The reaction mixture was stirred at RT for 48 h under $H_2$. After the reaction was completed, the mixture was filtered. The filtrate was evaporated in vacuo. The residue was purified by reverse phase flash chromatography to afford ethyl 3-benzyl-1H-pyrazole-5-carboxylate (75) as a yellow solid (2.2 g, 50%). $^1$H NMR (DMSO-$d_6$, 300 MHz) δ 7.35-7.19 (m, 5H), 6.48 (s, 1H), 4.23 (q, J=7.2 Hz, 2H), 3.97 (s, 2H), 1.26 (t, J=7.2 Hz, 3H). ESI-MS, m/z=231 $[M+H]^+$.

3-Benzyl-1H-pyrazole-5-carboxylic acid (76)

To a solution of ethyl 3-benzyl-1H-pyrazole-5-carboxylate (75, 500.0 mg, 2.2 mmol) in methanol/water (10/2 mL) was added sodium hydroxide (176.0 mg, 4.4 mmol). The resulting mixture was refluxed for 1 h. After the reaction was completed, the mixture was evaporated in vacuo to remove most of the solvents. The pH value of the mixture was adjusted to 1 with 1N $HCl_{(aq)}$. The mixture was extracted with ethyl acetate, washed with brine, dried over anhydrous sodium sulfate and filtered. The filtrate was evaporated in vacuo. The residue was purified by Prep-HPLC with the conditions (column: SunFire Prep $C_{18}$ OBD column 19×150 mm 5 μm 10 nm; Mobile Phase A: water (0.1% formic acid), Mobile Phase B: acetonitrile; Flow rate: 25 mL/min; Gradient: 15% B to 35% B in 9 min; 254/220 nm; $R_t$: 8.9 min) to afford 3-benzyl-1H-pyrazole-5-carboxylic acid (76) as a white solid (130.0 mg, 30%). $^1$H NMR (DMSO-$d_6$, 300 MHz) δ 13.04 (s, 2H), 7.33-7.19 (m, 5H), 6.46 (s, 1H), 3.96 (s, 2H). ESI-MS, m/z=203 $[M+H]^+$.

6-(Naphthalen-1-ylmethyl)-3-oxo-2, 3-dihydropyridazin-4-yl 3-benzyl-1H-pyrazole-5-carboxylate (77)

To a stirring solution of 4-hydroxy-6-(naphthalen-1-ylmethyl) pyridazin-3(2H)-one (61, 500.0 mg, 2.0 mmol) in ethyl acetate (10 mL) was added propylphosphonic anhydride solution (50% in ethyl acetate) (1.5 mL, 2.5 mmol), pyridine (0.8 mL, 9.8 mmol) and 3-benzyl-1H-pyrazole-5-carboxylic acid (76, 404.0 mg, 2.0 mmol). The reaction mixture was stirred at RT overnight. The mixture was diluted with water, extracted with ethyl acetate, washed with brine, dried over anhydrous sodium sulfate and filtered. The filtrate was evaporated in vacuo. The residue was purified by flash column chromatography with methanol/dichloromethane (5:95) and then purified by Prep-HPLC (column: XBridge Prep $C_{18}$ OBD column 19×150 mm 5 μm C0013; Mobile Phase A: water (0.1% formic acid), Mobile Phase B: acetonitrile; Flow rate: 25 mL/min; Gradient: 45% B to 66% B in 7 min; 254/220 nm) to afford 6-(naphthalen-1-ylmethyl)-3-oxo-2, 3-dihydropyridazin-4-yl 3-benzyl-1H-pyrazole-5-carboxylate (77) as an off-white solid (73.0 mg, 8%).

¹H NMR (DMSO-d₆, 300 MHz) δ 13.68 (s, 1H), 13.24 (s, 1H), 8.14-8.11 (m, 1H), 7.97-7.92 (m, 1H), 7.88-7.83 (m, 1H), 7.59-7.44 (m, 5H), 7.34-7.20 (m, 5H), 6.63 (s, 1H), 4.45 (s, 2H), 4.02 (s, 2H). ESI-MS, m/z=437 [M+H]⁺.

Example 22: In vitro measurements of D-amino acid oxidase (DAAO) activities

The pkDAAO (porcine kidney DAAO) activity was measured by using D-Proine as a substrate to produce hydrogen peroxide ($H_2O_2$). The produced $H_2O_2$ would be oxidized by peroxidase, and the produced free radicals would further react with 1, 2-Phenylenediamine (OPD) reagent. The reaction product had an absorbance on 450 nm. The OD450 would be measured to represent the activity of pkDAAO. All compounds were dissolved in DMSO. Each compound was diluted with DMSO in 3 or 4-fold serial dilution to create a 9-point dose response curve. Each sample was added in triplicate, 10 μL/well, into 96-well assay microplate. Positive control wells were added with 10 μL of DMSO. The diluted compounds were incubated with pkDAAO in dark for 10 minutes and then reacted with D-Proline. The final reaction mixture was composed of 0.01 U/mL pkDAAO, 0.03% OPD, 25 μU/mL HRP and 40 mM D-Proline in PBS. The reaction plates were then incubated in the dark at room temperature. The OD450 absorbance readout was detected at 0 and 20 minute by Molecular Device Spectra Max Plus reader. The percentage of inhibition values for each well were calculated with the following equation:

The percentage of inhibition=(OD450$_{sample,20\ min}$−OD450$_{sample,0\ min}$)/(OD450$_{DMSO,\ 20\ min}$−OD450$_{DMSO,0\ min}$)×1000%

The nonlinear curve fitting model in GraphPad Prism 5 was used to calculate IC$_{50}$ value for each compound.

The hDAAO (human DAAO) activity was measured by using D-serine as a substrate to produce $H_2O_2$. The produced $H_2O_2$ would be oxidized by peroxidase, and the produced free radicals would further react with Amplex Red reagent to emit fluorescence. The intensity of fluorescence at 590 nm would be measured to represent the activity of hDAAO. All compounds were dissolved in DMSO. Each compound was diluted with DMSO in 3-fold serial dilution to create a 9-point dose response curve. Each sample was added in triplicate, 1 μL/well, into 96-well black plates. Positive control wells were added with 1 μL of DMSO. Then 49 μL of assay buffer (100 mM Tris-HCl, pH 8.5) containing 1.2 ng/mL hDAAO, 900 nM FAD, 0.2 units/mL HRP, and 100 μM Amplex Red was added to each well of the plate using a multichannel pipette. Next, 50 μL of 100 mM D-Serine in assay buffer was added. The reaction plates were then incubated in the dark at room temperature. The fluorescence readout was detected at 0 and 20 minute by Molecular Device Gemini EM fluorescence reader using the following settings: excitation filter 530 nm, and emission filter 590 nm. The percentage of inhibition values for each well was calculated with the following equation:

The percentage of inhibition=(fluorescence$_{sample,20\ min}$−fluorescence$_{sample,0\ min}$)/(fluorescence$_{DMSO,20\ min}$−fluorescence$_{DMSO,0\ min}$)×100%

The nonlinear curve fitting model in GraphPad Prism 5 was used to calculate IC$_{50}$ value for each compound.

TABLE 1

| DAAO Inhibitory Activities | | |
|---|---|---|
| Compound No. | hDAAO IC$_{50}$ (μM) | pkDAAO IC$_{50}$ (μM) |
| 1 | 100-500 | 10,000-50,000 |
| 5 | 10-100 | 10-100 |
| 9 | 1-10 | 10-100 |
| 14 | 1-10 | 10-100 |
| 18 | 0.1-0.5 | 1-10 |
| 23 | 0.1-1 | 1-10 |
| 27 | 0.1-0.5 | 0.1-1 |
| 32 | 0.1-1 | 0.1-0.5 |
| 49 | 1-10 | 0.1-1 |
| 50 | 1-10 | 1-10 |
| 56 | 1-10 | 10-100 |
| 62 | 0.1-1 | 0.01-0.1 |
| 67 | 0.1-0.5 | 0.01-0.1 |
| 72 | 0.1-0.5 | 0.01-0.1 |
| 77 | 0.1-1 | 0.01-0.1 |
|  | 0.1-0.5 | 0.01-0.1 |

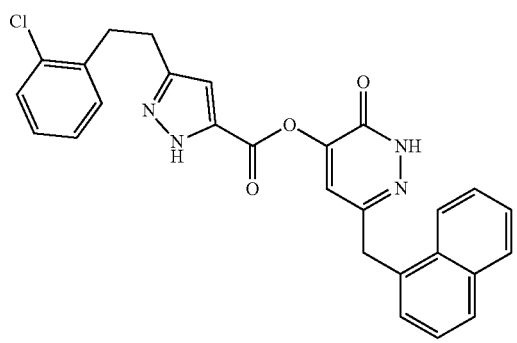 [SMILES: O=C(Oc1cc(Cc2cccc3ccccc23)n[nH]c1=O)c1cc(CCc2ccccc2Cl)n[nH]1]

TABLE 1-continued

DAAO Inhibitory Activities

| Compound No. | hDAAO IC$_{50}$ (μM) | pkDAAO IC$_{50}$ (μM) |
|---|---|---|
| 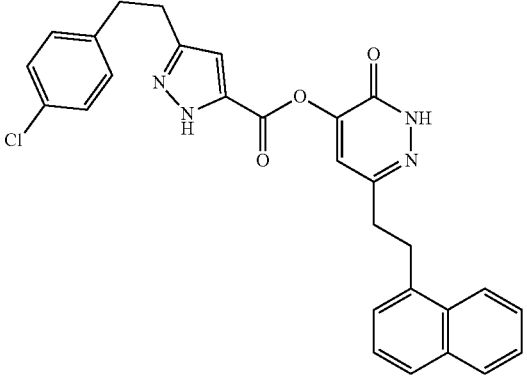 [SMILES: O=C(Oc1cc(CCc2cccc3ccccc23)n[nH]c1=O)c1cc(CCc2ccc(Cl)cc2)n[nH]1] | 0.1-0.5 | 0.01-0.1 |
| 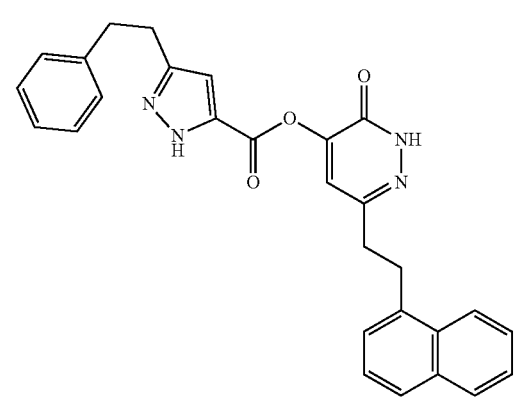 [SMILES: O=C(Oc1cc(CCc2cccc3ccccc23)n[nH]c1=O)c1cc(CCc2ccccc2)n[nH]1] | 0.1-0.5 | 0.01-0.1 |
| 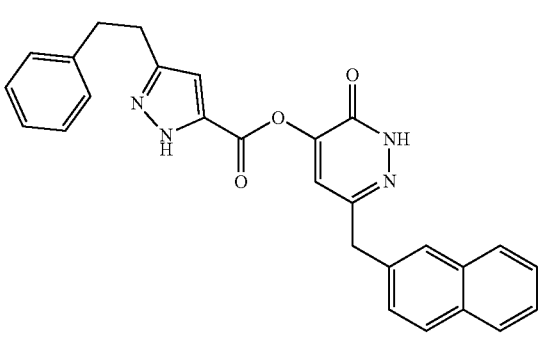 [SMILES: O=C(Oc1cc(Cc2ccc3ccccc3c2)n[nH]c1=O)c1cc(CCc2ccccc2)n[nH]1] | 0.1-0.5 | 0.01-0.1 |

The IC$_{50}$ values of some compounds are shown in Table 1. At the beginning, initially tested compounds did not provide good inhibitory activity. The IC$_{50}$ values were over 100 μM. After testing compounds with modified structures, IC$_{50}$ values of lower than 1 μM were obtained. The best compounds provided IC$_{50}$ values lower than 0.5 μM.

Example 23: Therapeutic Effects of the Compound of Example 1

The Effects of the Compound of Example 1 on Mice's Spontaneous Locomotion

The mice were group housed (3-5 mice per cage) with food and water available ad libitum in polysulfone ventilated cages (Alternative Design, AR, USA) in the animal rooms of SyneuRx International (Taiwan) Corp. The colony was maintained on a 12/12-hr light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The compound of Example 1 was placed into 100% PEG400, and was sonic vibrated until solution became clear. Appropriate amount of PBS (phosphate buffer saline) was added to the compound of Example 1/PEG400 clear solution tot reach the final concentration of each dose level. The adult mice were randomly assigned to three groups: vehicle control, Example 1 at 446 mg/kg and Example 1 at 892 mg/kg treatments.

An exemplary design of the experiment is shown in FIG. 1. Mice that received oral administration of either vehicle or low/high dose of the compound of Example 1 was immediately subjected to open field test and the index of spontaneous locomotion was expressed as total travel distance measured within the defined time frame.

The mice were placed in a Plexiglas cage (37.5 cm×21.5 cm×18 cm) under 50-65 lux light intensity, the spontaneous locomotion was measured for 120 minutes using the Etho-Vision video tracking system (Noldus Information Technology, the Netherlands). The travel distance of each mouse was measured as an index of spontaneous locomotion.

Figure 2:
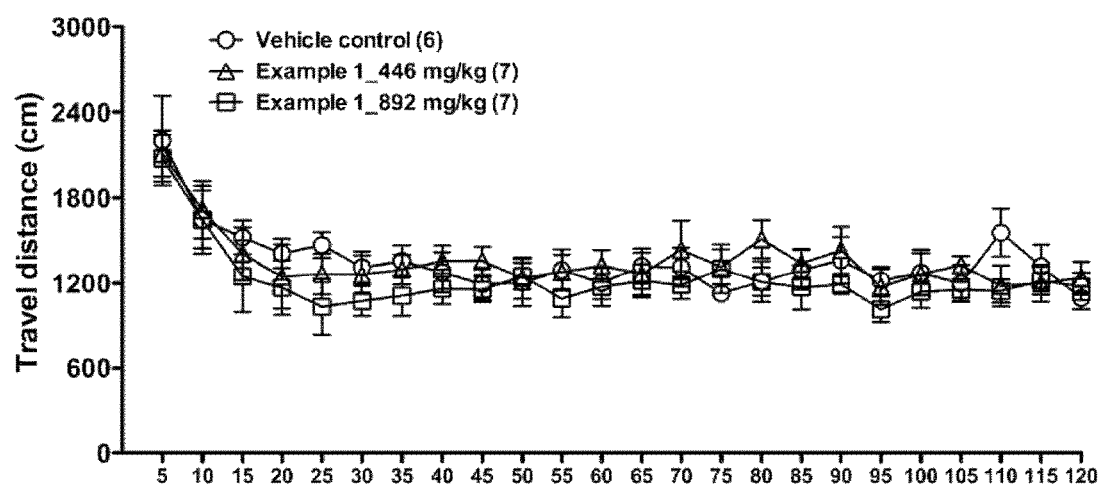
FIG. 2 is a diagram showing the spontaneous locomotion of the mice after administration of the compound of Example 1.

FIG. 2 shows the spontaneous locomotion after administration of the compound of Example 1, recording in 5 minute bins.

Mice in each group displayed habituation toward the testing chamber within 30 minutes. There was no significant difference between groups during the 120 minutes observation.

The Effects of the Compound of Example 1 on MK801-Treated Mice

The mice were group housed (3-5 mice per cage) with food and water available ad libitum in polysulfone ventilated cages (Alternative Design, AR, USA) in the animal rooms of the SyneuRx International (Taiwan) Corp. The colony was maintained on a 12/12-hr light/dark cycle at the temperature of 22±2° C. and all behavioral studies were performed during dark cycle. All animals used in this study were adult mice (at least 2.5 months of age). All animal procedures were performed according to the protocols approved by the Institutional Animal Care and Use Committee (IACUC). The mice were randomly assigned into four groups, Group 1: vehicle control, Group 2: MK801, Group 3: Example 1 at 446 mg/kg+MK801, Group 4: Example 1 at 892 mg/kg+MK801. Mice in Groups 2-4 received an acute administration of MK-801 (Sigma-Aldrich USA, a NMDA receptor antagonist, dissolved in normal saline, 0.1 mg/kg, i.p.) 20 minutes prior to behavioral tests. On the other hand, each mouse in Groups 4-5 received orally an acute administration of 446 or 892 mg/kg of the compound of Example 1 (dissolved in PBS with 30% PEG400 20 minutes prior to the MK801 administration. In addition, the dose of MK801 was adjusted by different requirement of each task (0.1 mg/kg for open field, 0.2 mg/kg for pre-pulse inhibition).

All mice in the experiments were tested by open field task and pre-pulse inhibition with at least 1-week interval between two tasks. The open field task was used to evaluate whether the compound of Example 1 can reverse the MK801-induced hyper-locomotion. The apparatus and recording method of open field were as descripted above, except the drug administrations. Pre-pulse inhibition (PPI) test, using SR-LAB startle apparatus (San Diego Instruments, San Diego, Calif., USA), was used to determine whether the compound of Example 1 administration can ameliorate the MK801-induced deficit of sensorimotor gating function in mice. Under a 72 dB background noise, each session was composed of 5 minutes accumulation period followed by 64 trials in four blocks. The pulse alone (PA) trial was a 40 ms, 120 dB white noise burst. In the pre-pulse (pp)+pulse trials, a 20 ms white noise pre-pulse stimuli of 78 dB (pp6), 82 dB (pp10), 90 dB (pp18) was presented 100 ms before a 40 ms 120 dB pulse. The non-stimulus (NS) trials presented the background noise only. The initial and the last blocks composed of six PA trials respectively. Two middle blocks consisted of PA, pp+pulse, and NS trials. These trials were presented pseudo-randomly and separated by inter-tribal interval of 15 s on average (varying between 10 to 20 s). The percentage of pre-pulse inhibition was calculated by the following formula: % PPI=100×[(PA score)−(pp-P score)]/(PA score), where the PA score was the average of the PA value in the middle blocks.

Figure 3:
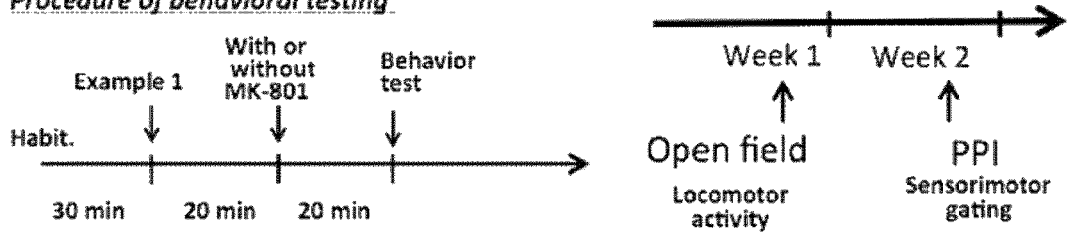
FIG. 3 is a diagram showing an exemplary design of the experiments of investigating open field and pre-pulse inhibition.

An exemplary design of the present experiments is shown in FIG. 3. The spontaneous locomotion activity and sensorimotor gating function of each mouse were tested by open field and pre-pulse inhibition, respectively, with at least 1-week interval between tests. Twenty minutes prior to the MK801 (or saline) injection, the compound of Example 1 (or vehicle) was administered to each mouse by gavage. Twenty minutes prior to the behavioral tests, the MK801 (or saline) was administrated to each mouse by i.p. injection.

Figure 4:
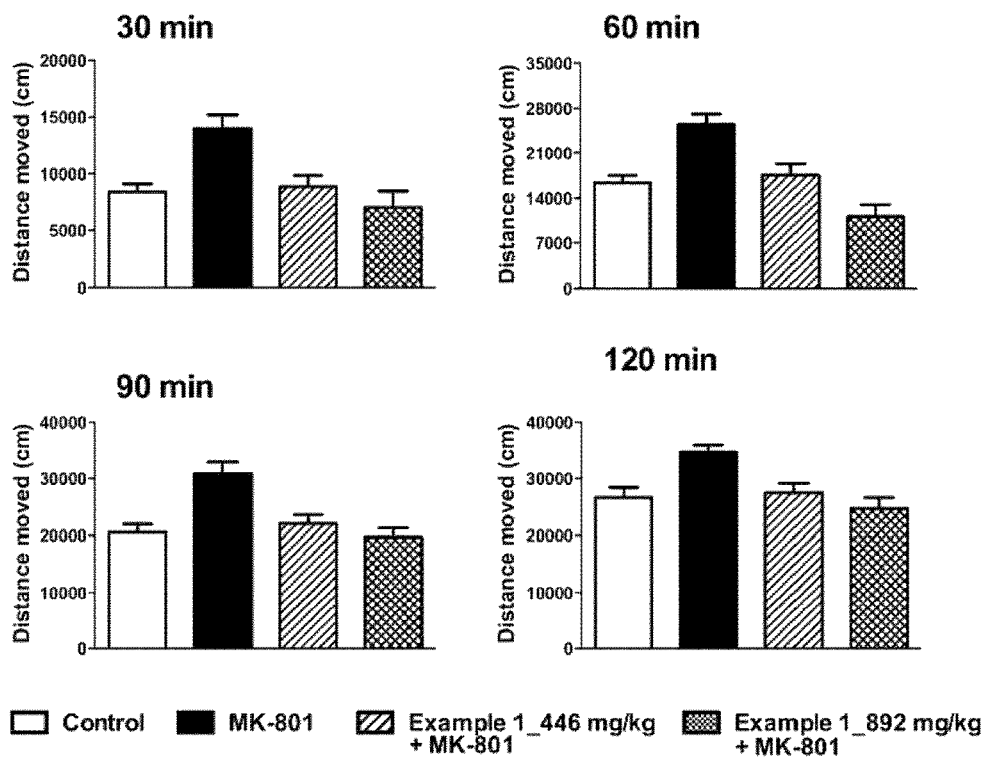
FIG. 4 includes diagrams showing the effects of the compound of Example 1 on locomotion in MK801-treated mice.

FIG. 4 shows the effects of the compound of Example 1 on locomotion in MK801-treated mice. Compared to the control group, the MK801-treated group displayed hyper-locomotion in open field task during the 120 minutes testing period. Mice that received either the low or high dose of the compound of Example 1 prior MK801 treatment displayed equal level of locomotion activity as mice in the control group during the 120 minutes testing period indicating amelioration of the MK801-induced hyper-locomotion by Example in these mice.

Figure 5:
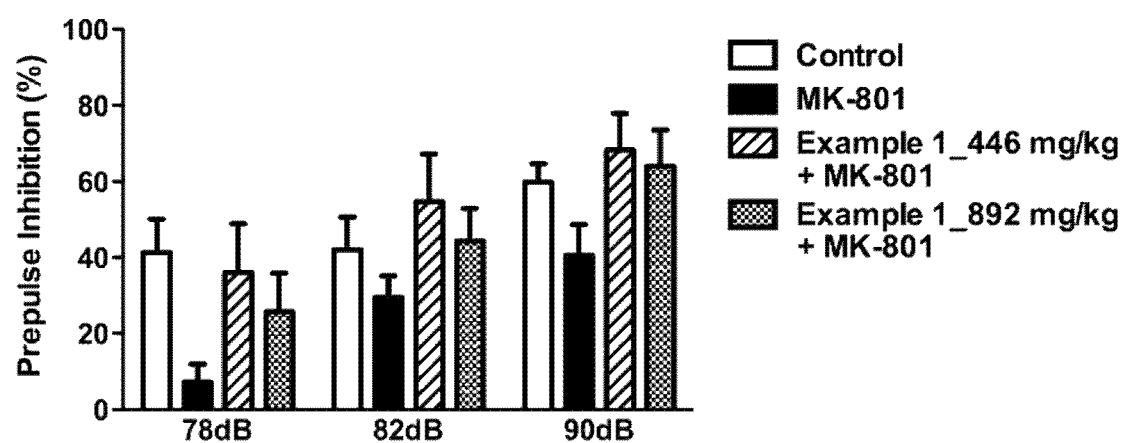
FIG. 5 is a diagram showing the effects of the compound of Example 1 on pre-pulse inhibition in MK801-treated mice.

FIG. 5 shows the effects of the compound of Example 1 on pre-pulse inhibition in MK801-treated mice. Compared to the control group, the MK801 group displayed lower percentage of pre-pulse inhibition in each pre-pulse intensity. Compared to the control group, the low/high dose of the compound of Example 1 treated groups displayed the same level of pre-pulse inhibition percentage in each pre-pulse intensity.

Psychosis symptoms are traditionally known to be challenging to observe and measure in animal model. However, recent developments have greatly improved the utility and validity of animal models in this field. As such, the psychosis-related behaviors can be tested in animal models include psychomotor agitation, excitement symptoms, sensory gating and sensitivity to psychotomimetic drugs, such as MK801 (Arguello & Gogos, 2006; Lai et al., 2014). In mice, parameters related to hyper-locomotion activity and alteration of novelty-induced locomotion activity (either impairment of habituation to novelty or increased exploration) in an open field task can be used to measure the psychomotor agitation and excitement symptoms, respectively (Lai et al., 2014; Powell & Miyakawa, 2006; Vardigan et al., 2010). In the present study, the administration of the compound of Example 1 reversed/protected MK801-induced hyper-locomotion activity in open field (FIG. 4). The result indicated that the compound of Example 1 is a potential drug for treating the psychosis symptoms (e.g. delusions and hallucinations).

Animal models involving MK-801 induced hyperactivity are commonly used in studying various neuropsychiatric disorders, and developing an analysis of conditions including, but not limited to, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia (see Rubia et al., 2010; Sheppard and Bradshaw, 1999; Bent et al., 2014; Powell and Miyakawa, 2006; Nestler and Hyman, 2010; Bubem´kova´-Vales˘ova et al., 2008; Gobira et al., 2013; Lai et al., 2014; Maio et al., 2014; Sontag et al., 2010; Ding et al., 2014; Walitza et al., 2007; Finestone et al., 1982; Golimstok et al., 2011).

In the pre-pulse inhibition task, administration of the compound of Example 1 at both low and high doses rescued/protected the MK801-induced PPI deficits. Deficits in pre-pulse inhibition have been commonly considered as a schizophrenic endophenotype in mouse models because the same deficit manifests can be identified in human (Arguello & Gogos, 2006; Geyer & Braff, 1987; Lai et al., 2014). The deficits of pre-pulse inhibition were also found in other central nerve system diseases, including schizophrenia, autism spectrum disorder, Asperger's disorder, obsessive compulsive disorder, Huntington's disease, nocturnal enuresis, attention deficit disorder, attention-deficit hyperactivity disorder, tic disorder, major depressive disorder, personality disorders, Tourette's syndrome, blepharospasm, non-epileptic seizures, post-traumatic stress disorder, panic disorder, bipolar disorder, mild dementia of Alzheimer, dementia with Lewy bodies, and Alzheimer's disease (see McAlonan et al., 2002; Braff et al., 2001; Giakoumaki et al., 2007; Ueki et al., 2006; Perriol et al., 2005; Ludewig et al., 2002; Castellanos et al., 1996; Cadenhead et al., 2000; Matsuo et al., 2017; Lai et al., 2014; McCool et al., 2003; Arguello and Gogos, 2006).

In summary, the results of the experiments described herein provide evidence that the compounds described herein are potent DAAO inhibitors and are promising drug candidates for the treatment of CNS disorders, particularly those involving DAAO.

Example 24: Therapeutic Effects of Compound 56

The Effects of Compound 56 on MK-801 Treated Mice

C57BL/6J male mice were group housed (3-5 mice per cage) with food and water available ad libitum in polysulfone ventilated cages (Alternative Design, AR, USA) in the animal room of SyneuRx. The colony was maintained on a 12/12-h light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The mice were randomly assigned into five groups, where Group 1: vehicle control, Group 2: MK-801, Group 3: Compound 56 at 10 mg/kg+MK-801, Group 4: Compound 56 at 30 mg/kg+MK-801, Group 5: Compound 56 at 100 mg/kg+MK-801. Mice at Group 2-5 received an acute administration of MK-801 (Sigma-Aldrich USA), a NMDA receptor antagonist, dissolved in normal saline, at 0.2 mg/kg for open field and 0.3 mg/kg for pre-pulse inhibition (PPI), respectively, by i.p. injection 20 minutes prior to the behavior tests. Each mouse at Group 3-5 received orally an acute administration of Compound 56 at 10, 30 and 100 mg/kg (dissolved in ddH$_2$O with 65% PEG400 and 10% DMSO) 20 minutes prior to the MK-801 administration. All mice were tested with the open field and pre-pulse inhibition tasks.

The open field task is a common measurement of novelty induced exploratory behavior and general activity in both mice and rats. The objective of this experiment was to evaluate the efficacy of compound 56 on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks (beam breaks) of each mouse was measured as an index of locomotion activity.

Pre-pulse inhibition, using SR-LAB startle apparatus (San Diego Instruments, San Diego, Calif., USA), was used to determine the efficacy of compound 56 on attenuating the MK-801 induced deficit of sensorimotor gating function in mice. Under 65 dB background noise, each session was composed of 5-minutes accumulation period followed by 64 trials in four blocks. The pulse alone (PA) trial was a 40 ms, 120 dB white noise burst. In the prepulse (pp)+pulse trials, a 20 ms white noise prepulse stimuli of 71 dB (pp6), 75 dB (pp10), and 83 dB (pp18) were presented 100 ms before a 40 ms 120 dB pulse. The non-stimulus (NS) trials presented the background noise only. The initial and the last blocks were composed of six PA trials, respectively. Two middle blocks consisted of PA, pp+pulse, and NS trials. These trials were presented pseudo-randomly and separated by intertribal intervals of 15 seconds on average (varying between 10 to 20 s). The percentage of prepulse inhibition was evaluated by the following formula: % PPI=100×[(PA score)−(pp-P score)]/(PA score), where the PA score was the average of the PA value in the middle blocks.

Figure 6:
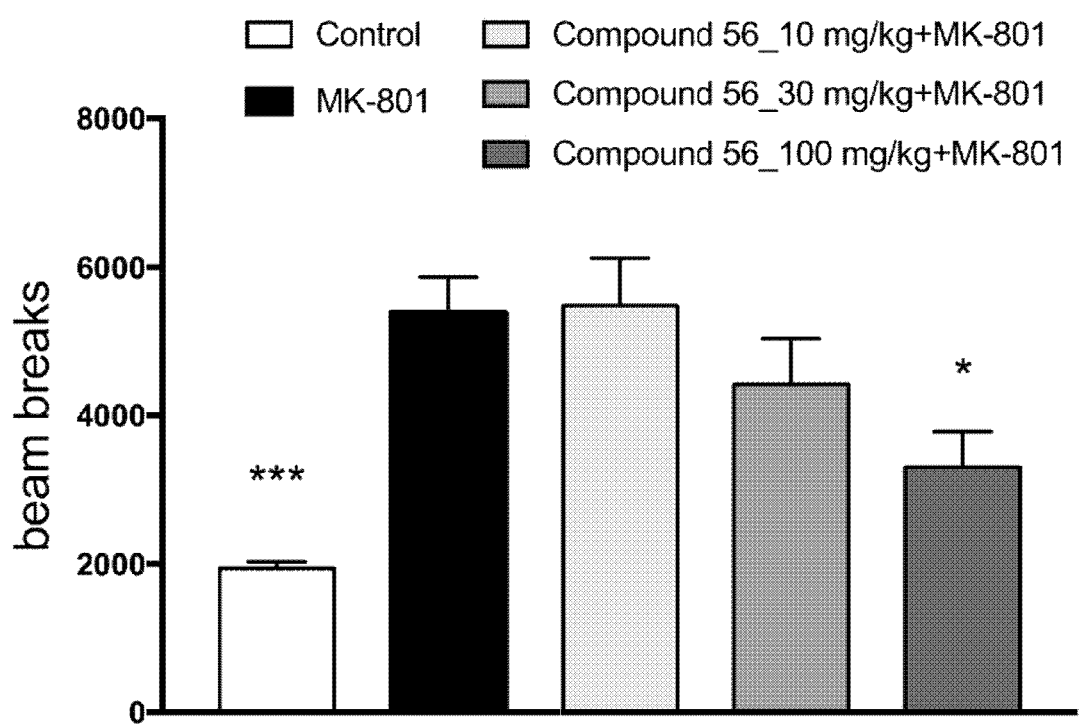
FIG. 6 is a graph showing the effects of compound 56 on locomotion in MK-801 treated mice.

FIG. 6 shows the effects of compound 56 (treatment with 10 mg/kg, 30 mg/kg, or 100 mg/kg of compound 56) on the locomotion (number of beam breaks) of MK-801 treated mice. Compared to the vehicle control group, the group treated with MK-801 alone (the MK-801 group) displayed hyper-locomotion in the open field task. In comparison to the MK-801 group, the group treated with a low dose (10 mg/kg) of compound 56 (and MK-801) showed no effect and the group treated with a middle dose (30 mg/kg) of compound 56 (and MK-801) displayed marginally lower locomotion activity, while the group treated with a high dose (100 mg/kg) of compound 56 (and MK-801) demonstrated significantly reduced MK-801 induced hyper-locomotion.

Figure 7:
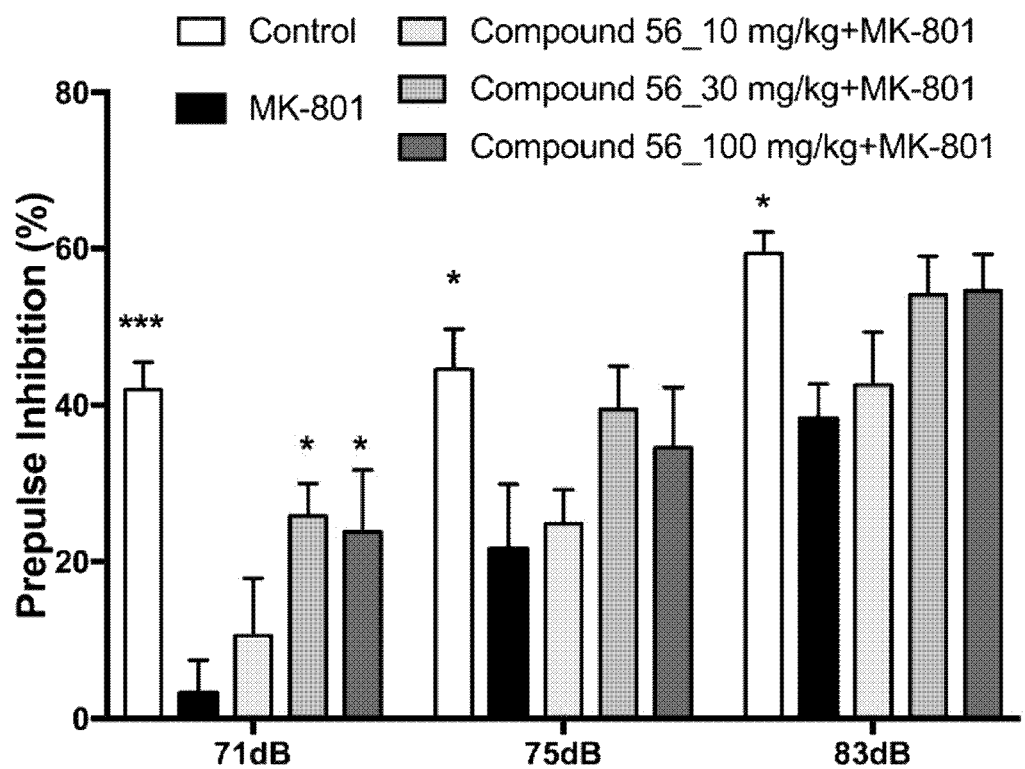
FIG. 7 is a graph showing the effects of compound 56 on pre-pulse inhibition in MK-801 treated mice.

FIG. 7 shows the effects of compound 56 (treatment with 10 mg/kg, 30 mg/kg, or 100 mg/kg of compound 56) on pre-pulse inhibition in MK-801 treated mice at different pre-pulse intensity levels (71 dB, 75 dB, 83 dB). Compared to the vehicle control group, the group treated with MK-801 group (the MK-801 group) displayed pre-pulse inhibition deficits in all pre-pulse intensity levels. At 71 dB pre-pulse intensity, treatment with compound 56 showed marginal improvement in pre-pulse inhibition deficits at 10 mg/kg and displayed a significantly higher percentage of pre-pulse inhibition (improved rescue effects on pre-pulse inhibition deficits) at 30 mg/kg and 100 mg/kg treatment with compound 56, in MK-801 treated mice. At the 75 and 83 dB pre-pulse intensities, the treatment with both 30 mg/kg and 100 mg/kg of compound 56 reduced the MK-801 induced pre-pulse inhibition deficit to a similar level as that of the vehicle control group, and demonstrated improved rescue effects on pre-pulse inhibition deficits.

Example 25: Synthesis of (78)

Synthesis of 6-(3, 5-difluorophenethyl)-3-oxo-2, 3-dihydropyridazin-4-yl 1H-pyrazole-5-carboxylate (78)

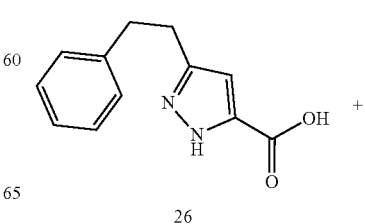

26

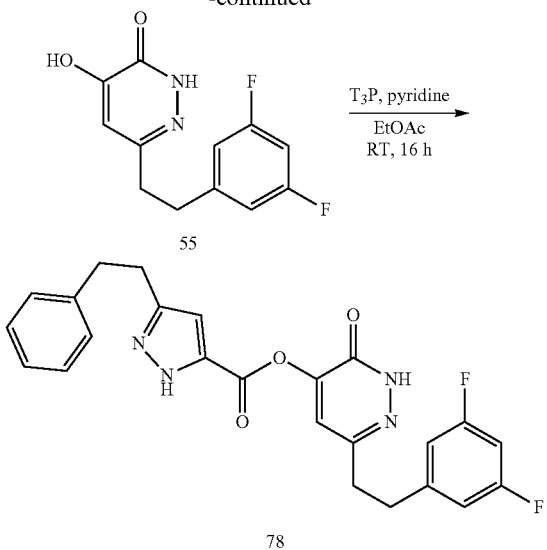

6-(3,5-difluorophenethyl)-3-oxo-2,3-dihydro-pyridazin-4-yl 3-phenethyl-1H-pyrazole-5-carboxylate (78)

Compound 78 was synthesized by the same methods as mentioned in Example 17 for compound 57, and according to the scheme above. The reaction was taken in 252 mg scale and afforded 6-(3,5-difluorophenethyl)-3-oxo-2,3-dihydro-pyridazin-4-yl 3-phenethyl-1H-pyrazole-5-carboxylate (78) as a white solid (30.2 mg, 7%). $^1$H NMR (300 MHz, DMSO-$d_6$) 13.56 (s, 1H), 13.19 (s, 1H), 7.51 (s, 1H), 7.32-7.17 (m, 5H), 7.00-7.08 (m, 3H), 6.69 (s, 1H), 2.98-2.73 (m, 8H). ESI-MS, m/z=451 [M+H]$^+$.

Example 26: Therapeutic Effects of Compound 78

The Effects of Compound 78 on MK-801 Treated Mice

C57BL/6J male mice were group housed (3-5 mice per cage) with food and water available ad libitum in polysulfone ventilated cages (Alternative Design, AR, USA) in the animal room of SyneuRx. The colony was maintained on a 12/12-h light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The mice were randomly assigned into five groups, where Group 1: vehicle control, Group 2: MK-801, Group 3: Compound 78 at 10 mg/kg+MK-801, Group 4: Compound 78 at 30 mg/kg+MK-801, Group 5: Compound 78 at 100 mg/kg+MK-801. Mice at Group 2-5 received an acute administration of MK-801 (Sigma-Aldrich USA), a NMDA receptor antagonist, dissolved in normal saline, at 0.2 mg/kg for open field and 0.3 mg/kg for pre-pulse inhibition (PPI), respectively, by i.p. injection 20 minutes prior to the behavior tests. Each mouse at Group 3-5 received orally an acute administration of Compound 78 at 10, 30 and 100 mg/kg (dissolved in ddH$_2$O with 65% PEG400 and 10% DMSO) 20 minutes prior to the MK-801 administration.

All mice were tested with the open field and pre-pulse inhibition tasks. The open field and pre-pulse inhibition tasks were used to evaluate the efficacy of the compound 78 on attenuating the MK-801 induced hyper-locomotion and deficit of sensorimotor gating function in mice, respectively. The apparatus and recording method used for the open field and pre-pulse inhibition tasks were as described above in Example 24.

Figure 8:
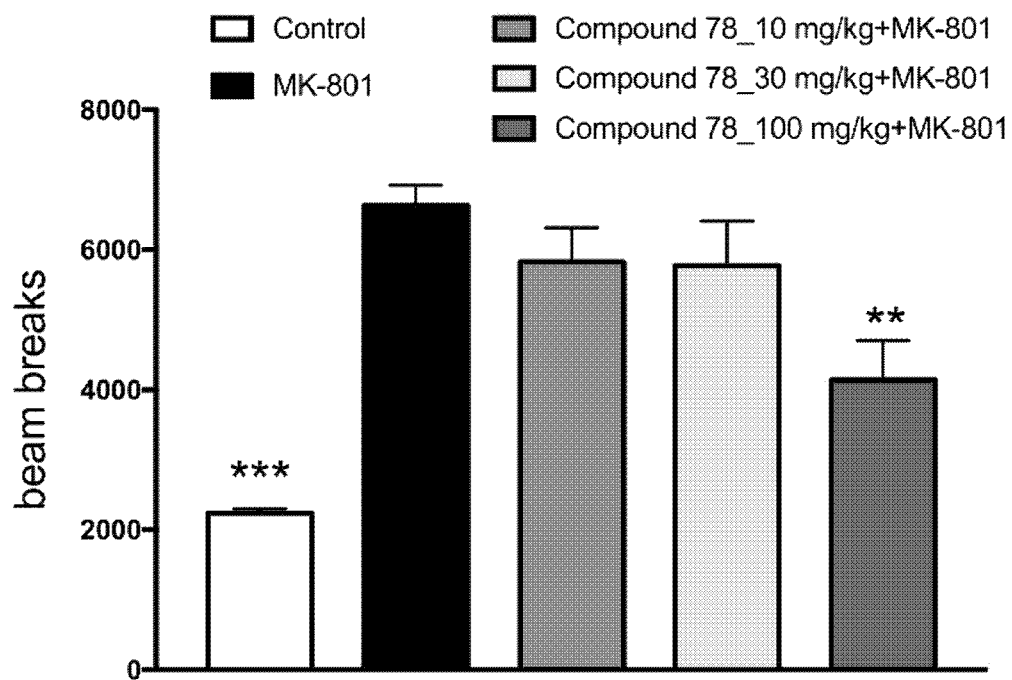
FIG. 8 is a graph showing the effects of compound 78 on locomotion in MK-801 treated mice.

FIG. 8 shows the effect of compound 78 on locomotion in MK-801 treated mice. Compared to the vehicle control group, the group treated with MK-801 alone (the MK-801 group) displayed hyper-locomotion in the open field task. In comparison to the MK-801 group, mice treated with the low and middle dose (10 mg/kg and 30 mg/kg) of compound 78 (and MK-801) displayed marginally lower locomotion activity, while mice treated with the high dose of compound 78 (and MK-801) demonstrated significantly reduced MK-801 induced hyper-locomotion.

Figure 9:
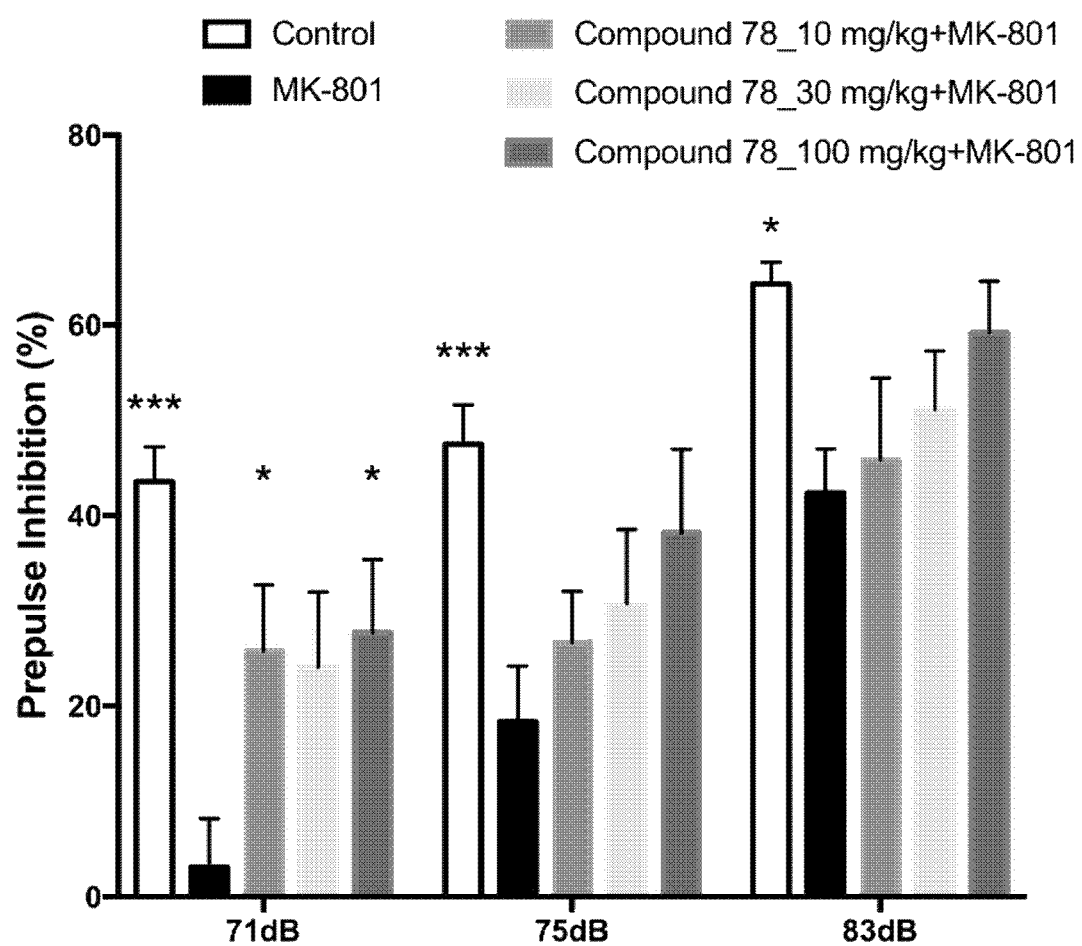
FIG. 9 is a graph showing the effects of compound 78 on pre-pulse inhibition in MK-801 treated mice.

FIG. 9 shows the effects of compound 78 (treatment with 10 mg/kg, 30 mg/kg, or 100 mg/kg of compound 78) on pre-pulse inhibition in MK-801 treated mice. Compared to the vehicle control group, the group treated with MK-801 alone (the MK-801 group) displayed pre-pulse inhibition deficits at all pre-pulse intensity levels. At 71 dB pre-pulse intensity, compound 78 showed an improvement effect on pre-pulse inhibition deficits and displayed a significantly higher percentage of pre-pulse inhibition at treatment with 10 mg/kg and 100 mg/kg compound 78. At 75 and 83 dB pre-pulse intensities, treatment with the compound 78 reduced MK-801 induced pre-pulse inhibition deficits in a dose dependent manner.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for inhibiting D-amino acid oxidase (DAAO) in a subject, the method comprising administering to a subject in need thereof an effective amount of a compound of Formula (I):

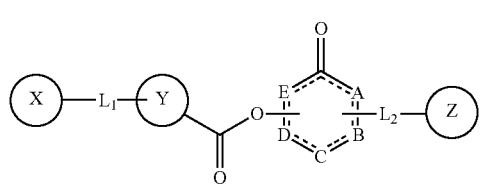

or a pharmaceutically acceptable salt thereof, wherein:

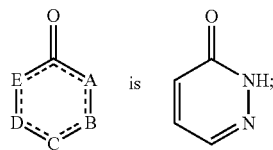

X is optionally substituted aryl or optionally substituted heteroaryl;
Y is optionally substituted heteroaryl;
Z is optionally substituted aryl or optionally substituted heteroaryl;
$L_1$ is $CH_2$ or $C_{2-10}$ alkyl;
$L_2$ is $CH_2$, $C_{2-10}$ alkyl, or —$CH_2S$,
wherein $L_2$ is bonded to C
or an effective amount of a composition comprising the compound.

2. The method of claim 1, wherein the subject is a human patient having a neuropsychiatric disorder, and wherein the neuropsychiatric disorder is selected from the group consisting of schizophrenia, dementia, mild cognitive impairment, depression, anxiety disorders, Parkinson's disorder, and amyotrophic lateral sclerosis.

3. The method of claim 1, wherein the subject is administered with the compound or the composition at a frequency of three times a day to one time every two months.

4. The method of claim 1, wherein $L_1$ and $L_2$, independently, is $CH_2$, or $C_{2-10}$ alkyl.

5. The method of claim 1, wherein X is naphthyl.

6. The method of claim 1, wherein Y is

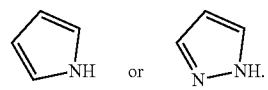

7. The method of claim 1, wherein Z is optionally substituted phenyl or optionally substituted naphthyl.

8. The method of claim 7, wherein Z is phenyl optionally substituted with halogen.

9. The method of claim 8, wherein Z is of the formula:

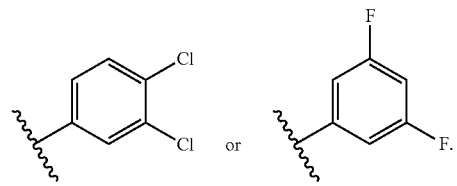 [SMILES: *c1ccc(Cl)c(Cl)c1 ; *c1cc(F)cc(F)c1]

10. The method of claim 1, wherein each of X and Z is independently selected from the group consisting of pyridyl, pyrimidyl, pyridazinyl, pyrazinyl, pyrrolyl, pyrazolyl, oxazolyl, thiazolyl, naphthyl, furopyrrolyl, thienopyrrolyl, and indolyl.

11. The method of claim 1, wherein $L_1$ is —$(CH_2)$— or —$(CH_2)_2$—.

12. The method of claim 1, wherein $L_2$ is —$(CH_2)$—, —$(CH_2)_2$—, or —$(CH_2)S$—.

13. The method of claim 1, wherein the compound is of the formula:

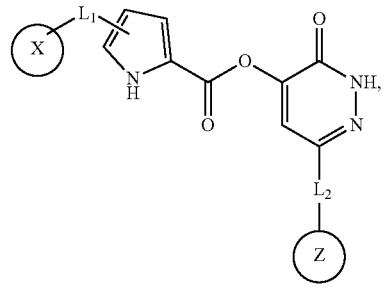

or a pharmaceutically acceptable salt thereof.

14. The method of claim 1, wherein the compound is of Formula (I-b):
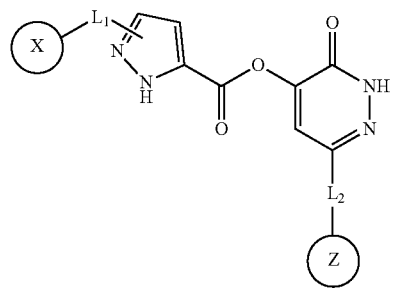
(I-b)
or a pharmaceutically acceptable salt thereof, wherein
X and Z are, each independently, optionally substituted aryl;
$L_1$ is $CH_2$ or $C_{2-10}$ alkyl; and
$L_2$ is $CH_2$, $C_{2-10}$ alkyl, or $—CH_2S$.
15. The method of claim 1, wherein the compound is selected from the group consisting of:
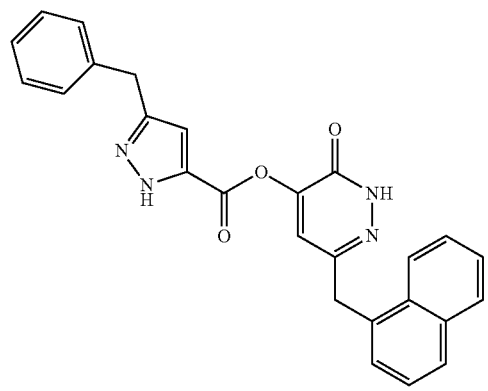
(77)
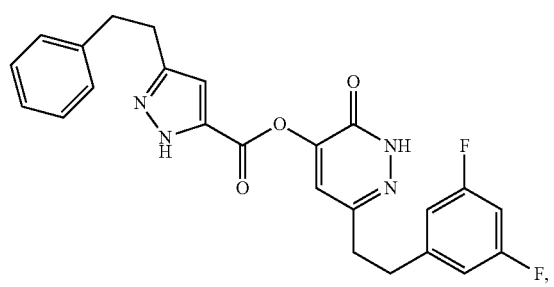
(78)
-continued
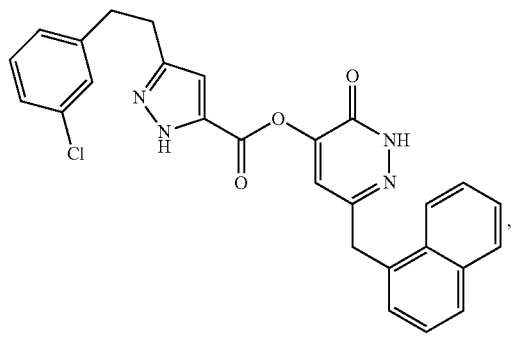
(67)
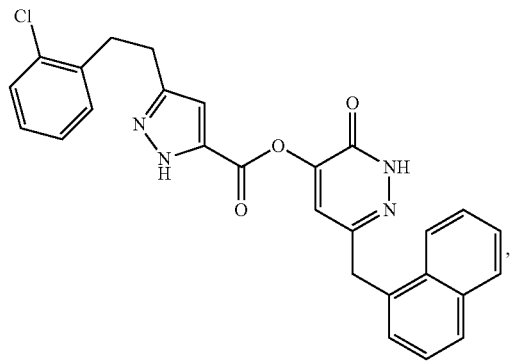
(72)
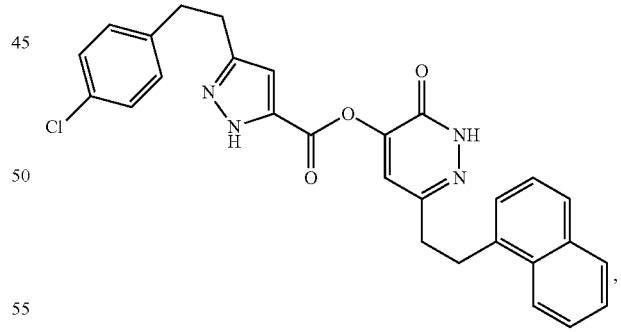
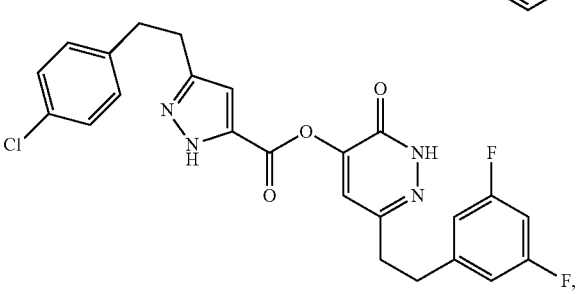

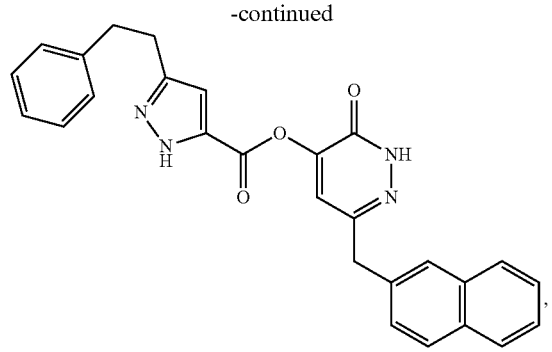
and
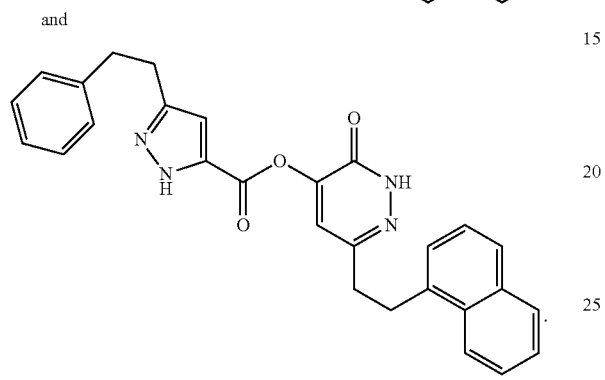
* * * * *